United States Patent
Brown et al.

(10) Patent No.: US 7,285,563 B2
(45) Date of Patent: Oct. 23, 2007

(54) HETEROAROMATIC UREA DERIVATIVES AS VR-1 RECEPTOR MODULATORS FOR TREATING PAIN

(76) Inventors: Rebecca Elizabeth Brown, Merck Sharp & Dohme, The Neuroscience Research Centre, Terlings Park, Eastwick Road, Harlow, Essex (GB) CM20 2QR; Victoria Alexandra Doughty, Merck Sharp & Dohme, The Neuroscience Research Centre, Terlings Park, Eastwick Road, Harlow, Essex (GB) CM20 2QR; Gregory John Hollingworth, Merck Sharp & Dohme, The Neuroscience Research Centre, Terlings Park, Eastwick Road, Harlow, Essex (GB) CM20 2QR; A. Brian Jones, Merck Sharp & Dohme, The Neuroscience Research Centre, Terlings Park, Eastwick Road, Harlow, Essex (GB) CM20 2QR; Matthew John Lindon, Merck Sharp & Dohme, The Neuroscience Research Centre, Terlings Park, Eastwick Road, Harlow, Essex (GB) CM20 2QR; Christopher Richard Moyes, Merck Sharp & Dohme, The Neuroscience Research Centre, Terlings Park, Eastwick Road, Harlow, Essex (GB) CM20 2QR; Lauren Rogers, Merck Sharp & Dohme, The Neuroscience Research Centre, Terlings Park, Eastwick Road, Harlow, Essex (GB) CM20 2QR ( * ) Notice: Subject to any disclaimer, the term of this patent is extended or adjusted under 35 U.S.C. 154(b) by 282 days.

(21) Appl. No.: 10/505,358

(22) PCT Filed: Mar. 21, 2003

(86) PCT No.: PCT/GB03/01302

§ 371 (c)(1),
(2), (4) Date: Aug. 19, 2004

(87) PCT Pub. No.: WO03/080578

PCT Pub. Date: Oct. 2, 2003

(65) Prior Publication Data
US 2005/0107388 A1    May 19, 2005

(30) Foreign Application Priority Data
Mar. 22, 2002    (GB) .................... 0206876.5

(51) Int. Cl.
*C07D 215/38*    (2006.01)
*A61K 31/47*    (2006.01)
(52) U.S. Cl. ..................... 514/310; 546/143
(58) Field of Classification Search .......... 546/145, 546/143; 514/307, 310
See application file for complete search history.

(56) References Cited

U.S. PATENT DOCUMENTS

| 4,045,439 A | 8/1977 | Preston et al. |
| 5,508,288 A | 4/1996 | Forbes et al. |
| 2003/0158188 A1 | 8/2003 | Chih-Hung Lee et al. |
| 2003/0158198 A1 | 8/2003 | Chih-Hung Lee et al. |

FOREIGN PATENT DOCUMENTS

| DE | 583207 C | 8/1933 |
| DE | 1157626 B | 11/1963 |
| DE | 2502588 A | 7/1976 |
| WO | WO93/18028 | * 9/1993 |
| WO | WO9324458 A | 12/1993 |
| WO | WO9414801 A | 7/1994 |
| WO | WO 0026203 A | 5/2000 |
| WO | WO 028221 A | 1/2002 |
| WO | WO 03014064 A1 | 2/2003 |
| WO | WO 03/070247 | 8/2003 |

OTHER PUBLICATIONS

Nowak et al, Studies in Organic Chemistry, vol. 35, 1988, pp. 438-440.*

(Continued)

*Primary Examiner*—Zinna N. Davis
(74) *Attorney, Agent, or Firm*—David Rubin; William Krovatin

(57) ABSTRACT

The present invention provides compounds of formula (I); pharmaceutically acceptable salts and N-oxides thereof in which A, B, D and E are C or N with the proviso that one or more are N, $R^1$, $R^2$, $R^3$, $R^4$, $R^5$ and $R^6$ are simple substituents, n is 0-3 and y is an aryl, heteroaryl, carbocyclyl or fused-carbocyclyl group; as VR-1 antagonists for treating conditions or diseases in which pain and/or inflammation predominates; the use of the same for manufacturing medicaments, pharmaceutical compositions comprising them and methods of treatment utilizing them

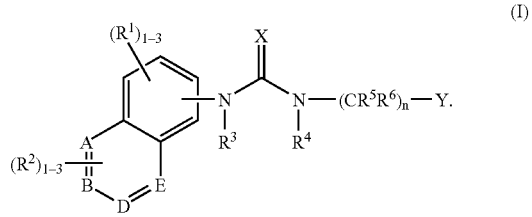

12 Claims, No Drawings

OTHER PUBLICATIONS

Enamine Product Listing, *2002:280319, Chemcats*, (Nov. 15, 2001).
Scientific Exchange Product List, *2003:2364305, Chemcats*, (Jan. 1, 2003).
Shiv K. Agarwal, et al., *Indian Journal of Chemistry*, vol. 31B, pp. 177-182, (Mar. 1992).
Teruki Honma, et al., *Journal of Medicinal Chemistry, American Chemical Society*, vol. 44, pp. 4615-4627, (2001).
Henryka Poradowska, et al., *Roczniki Chemii Annales Societatis Chimicae Polonorum*, vol. 49, pp. 1577-1580, (1975).
Henryka Poradowska, et al., *Polish Journal of Chemistry—Polish Chemical Society*, vol. 53, pp. 1895-1900, (1979).
J. H. Musser, et al., *Journal of Medicinal Chemistry, American Chemical Society*, vol. 30, No. 1, pp. 62-67, (1987).
K. C. Joshi, et al., *Journal of the Indian Chemical Society, The Indian Chemical Society*, vol. 54, pp. 1104-1105, (1977).
S. M. Sondhi, et al., *Monatshefte Fur Chemie Chemical Monthly*, vol. 131, No. 5, pp. 511-520, (2000).
Jewoo Lee, et al., *Bioorganic & Medicinal Chemistry*, vol. 9, pp. 1713-1720, (2001).
Communication pursuant to Article 96(2) EPC dated Oct. 20, 2006.
Letter from Merck & Co., Inc to European Patent Office dated Dec. 9, 2005.

\* cited by examiner

HETEROAROMATIC UREA DERIVATIVES AS VR-1 RECEPTOR MODULATORS FOR TREATING PAIN

CROSS REFERENCE TO RELATED APPLICATIONS

This application claims the benefit of Great Britain Provisional Application No. 0206876.5 filed Mar. 22, 2002, and PCT/GB03/01302, filed Mar. 21, 2003.

The present invention is concerned with heteroaromatic ureas and pharmaceutically acceptable salts and prodrugs thereof which are useful as therapeutic compounds, particularly in the treatment of pain and other conditions ameliorated by the modulation of the function of the vanilloid-1 receptor (VR1).

The pharmacologically active ingredient of chili peppers has been recognized for some time to be the phenolic amide capsaicin. The application of capsaicin to mucous membranes or when injected intradermally, causes intense burning-like pain in humans. The beneficial effects of topical administration of capsaicin as an analgesic is also well established. However, understanding of the underlying molecular pharmacology mediating these responses to capsaicin has been a more recent development.

The receptor for capsaicin, termed the vanilloid VR1 receptor, was cloned by Caterina and colleagues at UCSF in 1997 (*Nature*, 398:816, 1997). VR1 receptors are cation channels that are found on sensory nerves that innervate the skin, viscera, peripheral tissues and spinal cord. Activation of VR1 elicits action potentials in sensory fibres that ultimately generate the sensation of pain. Importantly VR1 receptor is activated not only by capsaicin by also by acidic pH and by noxious heat stimuli and thus appears to be a polymodal integrator of painful stimuli.

The prototypical VR1 antagonist is capsazepine (Walpole et al., *J. Med. Chem.*, 37:1942, 1994). This has only micromolar affinity for VR1 and is non-specific in its action. A novel series of sub-micromolar antagonists has also been reported recently (Lee et al, *Bioorg. Med. Chem.*, 9:1713, 2001), but these reports provide no evidence for in vivo efficacy. A much higher affinity antagonist has been derived from the 'ultra-potent' agonist resiniferatoxin. Iodo-resiniferatoxin (Wahl et al., *Mol. Pharmacol.*, 59:9, 2001) is a nanomolar antagonist of VR1 but does not possess properties suitable for an oral pharmaceutical. This last is also true of the micromolar peptoid antagonists described by Garcia-Martinez (*Proc. Natl. Acad. Sci., USA*, 99:2374, 2002). Most recently International (PCT) patent publication No. WO 02/08221 has described a novel series of VR1 antagonists, which are stated to show efficacy in a number of animal models. We herein describe another novel series of VR1 modulators. These comprise predominantly VR1 antagonists but encompass VR1 partial antagonists and VR1 partial agonists. Such compounds have been shown to be efficacious in animal models of pain.

Structurally related compounds are disclosed in EP-A-0418071, WO-A-9104027, WO-A-9324458, U.S. Pat. Nos. 5,596,001 and 5,362,818 all in the name of Pfizer Inc., WO-A-0064888 and WO-A-0064876 in the name of Aventis Pharmaceutical Products Inc. and WO-A-9406280 in the name of The Regents of the University of California. None of the compounds disclosed are for treating pain.

The present invention provides compounds of formula (I):

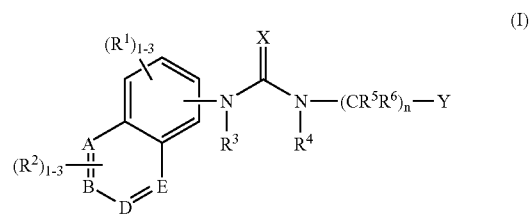

wherein
A, B, D and E are each C or N with the proviso that one or more are N;
$R^1$ and $R^2$ are each independently hydrogen, halogen, hydroxy, $C_{1-6}$alkyl, $C_{2-6}$alkenyl, $C_{2-6}$alkynyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-5}$cycloalkyl$C_{1-4}$alkyl, $NR^7R^8$, carboxy, esterified carboxy, $C_{1-6}$alkyl substituted with a group selected from $NR^7R^8$, carboxy and esterified carboxy, or $C_{1-6}$alkoxy substituted with a group selected from $NR^7R^8$, carboxy and esterified carboxy;
$R^3$ and $R^4$ are each independently hydrogen, $C_{1-6}$alkyl, $C_{2-6}$alkenyl or $C_{2-6}$alkylenyl;
$R^5$ and $R^6$ are, at each occurrence, independently hydrogen, $C_{1-6}$alkyl, $C_{2-6}$alkenyl, $C_{2-6}$alkynyl, $C_{1-6}$alkoxy, $C_{1-6}$acyloxy, carboxy, esterified carboxy, $CONR^7R^8$, $SO_2R^7$, $SO_2NR^7R^8$, aryl, heteroaryl, heterocyclyl, or $C_{1-6}$alkyl substituted with a group selected from hydroxy, $C_{1-6}$alkoxy, $C_{1-6}$acyloxy, carboxy, esterified carboxy, $NR^7R^8$, $CONR^7R^8$, $SR^7$, $SO_2R^7$, $SO_2NR^7R^8$, aryl, heteroaryl and heterocyclyl;
or $R^5$ and $R^6$ and the carbon atom to which they are attached together form a carbocyclic ring of 3 to 6 carbon atoms;
$R^7$ and $R^8$ are, at each occurrence, independently hydrogen, $C_{1-6}$alkyl, $C_{2-6}$alkenyl, $C_{2-6}$alkynyl, $C_{3-7}$cycloalkyl or fluoro$C_{1-6}$alkyl;
or $R^7$ and $R^8$ and the nitrogen atom to which they are attached together form a heteroaliphatic ring of 4 to 7 ring atoms, optionally substituted by one or two groups selected from hydroxy or $C_{1-4}$alkoxy, which ring may optionally contain as one of the said ring atoms an oxygen or a sulfur atom, a group $S(O)$ or $S(O)_2$, or a second nitrogen atom which will be part of a NH or $NR^a$ moiety where $R^a$ is $C_{1-4}$alkyl optionally substituted by hydroxy or $C_{1-4}$alkoxy;
X is an oxygen or sulfur atom or the group=NCN;
Y is an aryl, heteroaryl, carbocyclyl or fused-carbocyclyl group; and
n is either zero or an integer from 1 to 3;
or a pharmaceutically acceptable salt, N-oxide or a prodrug thereof.

$R^1$ may be absent or one or two $R^1$ groups may be present, as a preferred embodiment. $R^1$ is thus preferably chosen independently from halogen, halo$C_{1-6}$alkyl and $C_{1-6}$alkoxy, such as fluorine, chlorine, trifluoromethyl and methoxy.

A preferred class of compound of formula (I) is that wherein $R^1$ is a hydrogen or halogen atom or a group selected from $C_{1-6}$alkyl and $C_{1-6}$alkoxy.

More particularly, a preferred class of compound of formula (I) is that wherein $R^1$ is a hydrogen or a halogen atom, particularly a hydrogen or a fluorine atom, and most especially a hydrogen atom.

Where $R^1$ is other than hydrogen, preferably there is only one $R^1$ substituent.

Generally $R^2$ is absent or one or two $R^2$ groups are present. Thus $R^2$ is preferably independently chosen from $C_{1-6}$alkoxy, halogen, di($C_{1-6}$alkyl)amino, $C_{1-6}$alkyl, hydroxy, $C_{1-6}$alkoxycarbonyl, carboxy, ammo, halo$C_{1-6}$alkyl, hydroxy$C_{1-6}$alkyl and amino$C_{1-6}$alkyl. More preferably $R^2$ is independently chosen from halogen, hydroxy, carboxy, amino, $C_{1-3}$alkoxy, di($C_{1-3}$alkyl)amino, $C_{1-3}$alkyl, $C_{1-3}$alkoxycarbonyl, halo$C_{1-3}$alkyl, hydroxy$C_{1-3}$alkyl and amino$C_{1-3}$alkyl. $R^2$ is particularly chosen independently from methoxy, methyl, ethyl, chlorine, dimethylamino, hydroxy, trifluoromethyl, methoxycarbonyl, carboxy, amino, hydroxymethyl and aminoethyl.

Another preferred class of compound of formula (I) is that wherein $R^2$ is a hydrogen or halogen atom or a group selected from $C_{1-6}$alkyl, halo$C_{1-6}$alkyl, $C_{1-6}$alkoxy, $NR^7R^8$, $C_{1-6}$alkyl substituted with $NR^7R^8$, and $C_{1-6}$alkoxy substituted with $NR^7R^8$, wherein $R^7$ and $R^8$ each independently preferably represent hydrogen atoms or $C_{1-4}$alkyl groups.

A further preferred class of compound of formula (I) is that wherein $R^2$ is a hydrogen or a halogen atom, or a group selected from $C_{1-4}$alkyl, $C_{1-4}$alkoxy and $NR^7R^8$, wherein $R^7$ and $R^8$ each independently preferably represent hydrogen atoms or $C_{1-4}$alkyl groups.

More particularly, $R^2$ preferably represents a hydrogen or chlorine atom or a group selected from methyl, methoxy and dimethylamino. Most preferably, $R^2$ is a hydrogen atom.

Where $R^2$ is other than hydrogen, preferably there is only one $R^2$ substituent.

Thus quinoline, isoquinoline and cinnoline moieties included within the scope of the invention include isoquinolin-5-yl, isoquinolin-8-yl, quinolin-5-yl, 2-oxidoisoquinolin-5-yl, 3-methoxyisoquinolin-8-yl, cinnolin-5-yl, 3-methylisoquinolin-5-yl, 1-chloroisoquinolin-5-yl, 1-dimethylaminoisoquinolin-5-yl, 3-methylisoquinolin-8-yl, 3-chloroisoquinolin-5-yl, 3-methylcinnolin-5-yl, 8-fluoroisoquinolin-5-yl, 1-hydroxyisoquinolin-5-yl, 3-trifluoromethylisoquinolin-5-yl, 1-chloro-3-ethyhsoquinolin-5-yl, 1-methylisoquinolin-5-yl, 6,8-difluoro-3-methylisoquinolin-5-yl, 7-trifluoromethyl-3-methylisoquinolin-5-yl, 3-methyl-8-fluoroisoquinolin-5-yl, 3-methyl-6-fluoroisoquinolin-5-yl, 7-methoxyisoquinolin-5-yl, 1,3-dimethylisoquinolin-5-yl, 3-methyl-7-chloroisoquinolin-5-yl, 7-chloroisoquinolin-5-yl, 6-fluoroisoquinolin-5-yl, 7-fluoroisoquinolin-5-yl, 4-methylisoquinolin-5-yl, 8-trifluoromethylisoquinolin-5-yl, 6-trifluoromethylisoquinolin-5-yl, 7-trifluoromethylisoquinolin-5-yl, 1-methyl-6-fluoroisoquinolin-5-yl, 1-chloroisoquinolin-5-yl, 1-methoxycarbonylisoquinolin-5-yl, 1-carboxyisoquinolin-5-yl, 1-aminoisoquinolin-5-yl, 1-hydroxymethylisoquinolin-5-yl, 3-methoxycarbonylisoquinolin-5-yl, 3-carboxyisoquinolin-5-yl, 3-dimethylaminoisoquinolin-5-yl, 3-(2-aminoethyl)isoquinolin-5-yl and 8-methoxyisoquinolin-5-yl.

A further preferred class of compound of formula (I) is that wherein $R^3$ is a hydrogen atom or a $C_{1-4}$alkyl group, particularly a hydrogen atom or a methyl group, and most especially a hydrogen atom.

A yet further preferred class of compound of formula (I) is that wherein $R^4$ is a hydrogen atom or a $C_{1-4}$alkyl group, particularly a hydrogen atom or a methyl group, and most especially a hydrogen atom.

Another preferred class of compound of formula (I) is that wherein $R^5$ and $R^6$ each independently represent a hydrogen atom or a group selected from $C_{1-6}$alkyl, $C_{1-6}$alkyl substituted by a group selected from hydroxy, $C_{1-6}$acyloxy, carboxy, esterified carboxy, $NR^7R^8$ and heterocyclyl, or an aryl group More particularly, a preferred class of compound of formula (I) is that wherein $R^5$ and $R^6$ each independently represent a hydrogen atom or a $C_{1-4}$alkyl or phenyl group, particularly a hydrogen atom or a methyl group, and most especially a hydrogen atom.

Thus $-(CR^5R^6)_n-$ can represent a bond, $-CH_2-$, $-(CH_2)_2-$, $-(CH_2)_3-$, $-CH(C_6H_5)CH_2CH_2-$, $-CHCH_3-$ and $-CH(CH_2COOCH_2CH_3)-$.

A further preferred class of compound of formula (I) is that wherein X is an oxygen atom. X may be sulphur or oxygen.

A yet further preferred class of compound of formula (I) is that wherein Y is an aryl group selected from unsubstituted phenyl or naphthyl and phenyl or naphthyl substituted by one or two substituents selected from halogen, $C_{1-4}$alkyl, $C_{1-4}$alkoxy, halo$C_{1-4}$alkyl, halo$C_{1-4}$alkoxy, phenyl, cyano, nitro, pyrazolyl, di($C_{1-6}$alkyl)amino, phenoxy, $-OCH_2O-$ and $C_{1-6}$alkylcarbonyl; or a heteroaryl group selected from pyridyl, thiazolyl, isoxazolyl, oxadiazolyl and pyrazolyl wherein each heteroaryl group is optionally substituted with one or two substituents selected from $C_{1-4}$alkyl, $C_{1-4}$alkoxy, halo$C_{1-4}$alkyl, halo$C_{1-4}$alkoxy, unsubstituted heteroaryl or phenyl which may be substituted by $C_{1-6}$alkyl or halogen; or a carbocyclyl group which is a $C_{5-7}$cycloalkyl radical that is unsubstituted or substituted by a phenyl ring; or a fused-carbocyclyl group which is a $C_{5-7}$cycloalkyl radical that is fused to a phenyl ring.

A yet further preferred class of compound of formula (I) is that wherein Y is an aryl group selected from unsubstituted phenyl and phenyl substituted by one or two substituents selected from halogen, $C_{1-4}$alkyl, $C_{1-4}$alkoxy, halo$C_{1-4}$alkyl, halo$C_{1-4}$alkoxy, phenyl and pyrazolyl; or a heteroaryl group selected from pyridyl, thiazolyl, isoxazolyl, oxadiazolyl and pyrazolyl wherein each heteroaryl group is optionally substituted with one or two substituents selected from $C_{1-4}$alyl, $C_{1-4}$alkoxy, halo$C_{1-4}$alkyl, halo$C_{1-4}$alkoxy, phenyl; or a carbocyclyl group which is a $C_{5-7}$cycloalkyl radical that is unsubstituted or substituted by a phenyl ring; or a fused-carbocyclyl group which is a $C_{5-7}$cycloalkyl radical that is fused to a phenyl ring.

Thus Y can be phenyl, biphen-4-yl, biphen-3-yl, 1,2,3,4-tetrahydronaphthalen-2-yl, 4-chlorophenyl, 3,5-di(trifluoromethyl)phenyl, 3,4-dimethylphenyl, 4-tertbutylphenyl, 3-tertbutylphenyl, 3-trifluoromethylphenyl, 4-trifiluoromethylphenyl, 3-fluoro-4-trifluoromethylphenyl, 2,3-dihydro-1H-inden-2-yl, 4-phenylcyclohexyl, 6,7,8,9-tetrahydro-5H-benzo[a][7]annulen-6-yl, 6,7,8,9-tetrahydro-5H-benzo[a][7]annulen-7-yl, 3-trifluoromethylpyridin-6-yl, 4-tertbutylpyridin-6-yl, 2-tertbutylpyridin-5-yl, 2-tertbutylpyridin-4-yl, 2-tertbutylpyridin-6-yl, 2-trifLuoromethylpyridin-5-yl, 2-(pyrazol-1-yl)phenyl, 4-(pyrazol-1-yl)phenyl, 2-phenylthiazol-5-yl, 2-(thiophen-2-yl)thiazol-3-yl, 3-phenylthiazol-2-yl, 5-phenylisoxazol-3-yl, 3-phenylisoxazol-5-yl, 3-phenyloxadiazol-5-yl, 2-benzylthiazol-4-yl, 1-(2-methylphenyl)pyrazol-4-yl, cyclohexyl, naphthalen-2-yl, 4-cyanophenyl, 4-nitrophenyl, 4-dimethylaminophenyl, 4-phenoxyphenyl, 1,3-benzodioxol-5-yl, 4-methylcarbonylphenyl, isoquinolin-6-yl, 4-(morpholin-4-ylmethyl)phenyl and 2-(2-morpholin-4-yletoxy)phenyl.

Another preferred class of compound of formula (I) is that wherein one of A, B, D and E is a nitrogen atom and the other three are carbon atoms, or A and B are nitrogen atoms and D and E are carbon atoms.

It will be appreciated that the group $R^2$ is attached to any available carbon atom represented by A, B, D and E.

When present, $R^7$ is preferably a hydrogen atom or a $C_{1-4}$alkyl group, and $R^8$ is preferably a hydrogen atom or a $C_{1-4}$alkyl group, or the group $NR^7R^8$ represents a heteroaliphatic ring selected from azetidinyl, pyrrolidinyl, piperidinyl, morpholinyl, thiomorpholinyl, piperazinyl or a piperazinyl group substituted on the nitrogen atom by $C_{1-4}$alkyl optionally substituted by hydroxy or $C_{1-4}$alkoxy. More preferably, the group $NR^7R^8$ represents a group selected from —$NH_2$, —$NHCH_3$, —$N(CH_3)_2$, —$NHCH_2CH_3$, —$N(CHCH_2CH_3$ and —$N(CH_2CH_3)_2$, and most especially, —$N(CH_3)_2$.

One favoured class of compound of the present invention is that of formula (Ia) and pharmaceutically acceptable salts, N-oxides and prodrugs thereof:

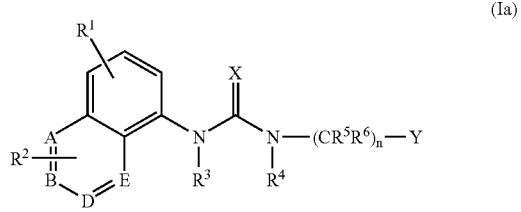

(Ia)

With reference to formula (Ia), preferably E is a carbon atom. Also preferred are those compounds of formula (Ia) where E is a carbon atom, one of A, B and D is a nitrogen atom and the others are carbon atoms, or where A and B are nitrogen atoms and D and E are carbon atoms.

Another favoured class of compound of the present invention is that of formula (Ib) and pharmaceutically acceptable salts, N-oxides and prodrugs thereof:

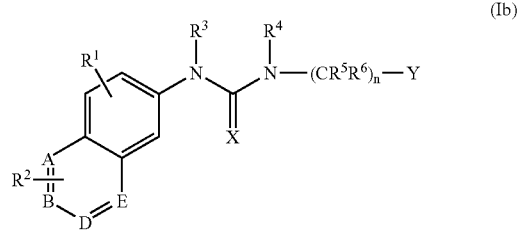

(Ib)

With reference to formula (Ib), preferably E is a carbon atom. Also preferred are those compounds of formula (Ib) where E is a carbon atom, one of A, B and D is a nitrogen atom and the others are carbon atoms, or where A and B are nitrogen atoms and D and E are carbon atoms. With reference to compounds of formula (Ib), preferably, A is a nitrogen atom and B, D and E are carbon atoms.

When any variable occurs more than one time in formula (I), formula (Ia) or formula (Ib) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

As used herein, the term "hydroxy$C_{1-6}$alkyl" means a $C_{1-6}$alkyl group in which one or more (in particular 1 to 3, and especially 1) hydrogen atoms have been replaced by hydroxy groups. Particularly preferred are hydroxy$C_{1-3}$alkyl groups, for example, $CH_2OH$, $CH_2CH_2OH$, $CH(CH_3)OH$ or $C(CH_3)_2OH$, and most especially $CH_2OH$.

As used herein, the terms "halo$C_{1-6}$alkyl" and "halo$C_{1-6}$alkoxy" means a $C_{1-6}$alkyl or $C_{1-6}$alkoxy group in which one or more (in particular, 1 to 3) hydrogen atoms have been replaced by halogen atoms, especially fluorine or chlorine atoms. Preferred are fluoro$C_{1-6}$alkyl and fluoro$C_{1-6}$alkoxy groups, in particular, fluoro$C_{1-3}$alkyl and fluoro$C_{1-3}$alkoxy groups, for example, $CF_3$, $CH_2CH_2F$, $CH_2CHF_2$, $CH_2CF_3$, $OCF_3$, $OCH_2CH_2F$, $OCH_2CHF_2$ or $OCH_2CF_3$, and most especially $CF_3$, $OCF_3$ and $OCH_2CF_3$.

The cycloalkyl groups referred to herein may represent, for example, cyclopropyl, cyclobutyl, cyclopentyl or cyclohexyl. Suitable $C_{3-7}$cycloalkyl$C_{1-4}$alkyl groups include, for example, cyclopropylmethyl and cyclohexylmethyl.

Similarly cycloalkoxy groups referred to herein may represent, for example, cyclopropoxy or cyclobutoxy.

As used herein, the terms "alkenyl" and "alkynyl" as a group or part of a group means that the group is straight or branched. Examples of suitable alkenyl groups include vinyl and allyl. A suitable alkynyl group is acetylene or propargyl.

When used herein, the term "halogen" means fluorine, chlorine, bromine and iodine. The most apt halogens are fluorine and chlorine of which fluorine is preferred, unless otherwise stated.

When used herein, the term "carboxy" as a group or part of a group denotes $CO_2H$.

When used herein, the term "esterified carboxy" denotes a $C_{1-6}$alkoxy or a halo$C_{1-6}$alkoxy radical attached via the oxygen atom thereof to a carbonyl (C=O) radical thus forming a $C_{1-6}$alkoxycarbonyl or halo$C_{1-6}$alkoxycarbonyl radical. Suitable examples of such esterified carboxy groups include, for example, methoxycarbonyl, ethoxycarbonyl, propoxycarbonyl, isopropoxycarbonyl and tert-butoxycarbonyl.

When used herein, the term "acyloxy" denotes a $C_{1-6}$alkyl or a halo$C_{1-6}$alkyl radical attached to a carbonyl (C=O) radical thus forming a $C_{1-6}$alkoyl or halo$C_{1-6}$alkanoyl radical which is attached via the carbonyl (C=O) radical to an oxygen atom. Suitable examples of such esterified carboxy groups include, for example, acetoxy, propionyloxy, isopropionyloxy and trifluoroacetoxy.

As used herein, the term "aryr" as a group or part of a group means an aromatic radical such as phenyl, biphenyl or naphthyl, wherein said phenyl, biphenyl or naphthyl group may be optionally substituted by one, two or three groups independently selected from halogen, hydroxy, $C_{1-6}$alkyl, $C_{1-6}$alkoxy, halo$C_{1-6}$alkyl, halo$C_{1-6}$alkoxy, $NR^7R^8$, benzyl, $NO_2$, cyano, $SR^b$, $SOR^b$, $SO_2R^b$, $COR^b$, $CO_2R^b$, $CONR^bR^c$, $C_{2-6}$alkenyl, $C_{2-6}$alkynyl, $C_{1-4}$alkoxy$C_{1-4}$alkyl, —$O(CH_2)_mO$— or a heteroaromatic group selected from furanyl, pyrrolyl, thienyl pyrazolyl, imidazolyl, oxazolyl, isoxazolyl, thiazolyl, isothiazolyl, oxadiazolyl, thiadiazolyl, pyridyl or pyridyl substituted by a group selected from halogen, halo$C_{1-6}$alkyl and halo$C_{1-6}$alkoxy (where $R^b$ and $R^c$ each independently represent hydrogen, $C_{1-4}$alkyl, $C_{3-5}$cycloalkyl or fluoro$C_{1-4}$alkyl or $R^b$ and $R^c$, together with the nitrogen atom to which they are attached form a piperidine, piperazine or morpholine ring and m is 1 or 2).

As used herein, the term "aryl" as a group or part of a group means an aromatic radical such as phenyl, biphenyl or naphthyl, wherein said phenyl, biphenyl or naphthyl group may be optionally substituted by one, two or three groups independently selected from halogen, hydroxy, $C_{1-6}$alkyl, $C_{1-6}$alkoxy, halo$C_{1-6}$alkyl, halo$C_{1-6}$alkoxy, $NR^7R^8$, benzyl, $NO_2$, cyano, $SR^b$, $SOR^b$, $SO_2R^b$, $COR^b$, $CO_2R^b$, $CONR^bR^c$, $C_{2-6}$alkenyl, $C_{2-6}$alkynyl, $C_{1-4}$alkoxy$C_{1-4}$alkyl, —O(CH$_2$)$_m$O— or a heteroaromatic group selected from furanyl, pyrrolyl, thienyl, pyrazolyl, imidazolyl, oxazolyl, isoxazolyl thiazolyl, isothiazolyl, oxadiazolyl, thiadiazolyl, pyridyl or pyridyl substituted by a group selected from halogen, halo$C_{1-6}$alkyl and halo$C_{1-6}$alkoxy (where $R^b$ and $R^c$ each independently represent hydrogen, $C_{1-4}$alkyl, $C_{3-5}$cycloalkyl or fluoro$C_{1-4}$alkyl and m is 1 or 2).

Preferably said phenyl, biphenyl or naphthyl group is optionally substituted by one or two substituents, especially none or one. Particularly preferred substituents include fluorine, chlorine, $C_{1-4}$alkyl (especially methyl or t-butyl), $C_{1-4}$alkoxy (especially methoxy), trifluoromethyl or trifluoromethoxy.

As used herein, the term "heteroaryl" as a group or part of a group means a 5 or 6-membered monocyclic heteroaromatic radical containing from 1 to 4 nitrogen atoms or an oxygen atom or a sulfur atom, or a combination thereof, or an 8- to 10-membered bicyclic heteroaromatic radical containing from 1 to 4 nitrogen atoms or an oxygen atom or a sulfur atom or a combination thereof. Suitable examples include pyrrolyl, furanyl, thienyl, pyridyl, pyrazolyl, imidazolyl, oxazolyl, isoxazolyl thiazolyl, isothiazolyl, pyrazinyl, pyrimidinyl, pyridazinyl triazolyl, oxadiazolyl, thiadiazolyl, triazinyl, tetrazolyl, indolyl, benzofuranyl, benzothiophenyl, benzimidazolyl, benzoxazolyl, benzthiazolyl, benzisothiazolyl, quinolinyl, isoquinolinyl and cinnolinyl, wherein said heteroaromatic radicals may be optionally substituted by one, two or three groups independently selected from halogen, hydroxy, $C_{1-6}$alkyl, $C_{1-6}$alkoxy, halo$C_{1-6}$alkyl, halo$C_{1-6}$alkoxy, $NR^7R^8$, phenyl, phenyl substituted by a group selected from halogen, halo$C_{1-6}$alkyl and halo$C_{1-6}$alkoxy, benzyl, $NO_2$, cyano, $SR^b$, $SOR^b$, $SO_2R^b$, $COR^b$, $CO_2R^b$, $CONR^bR^c$, $C_{2-6}$alkenyl, $C_{2-6}$alkynyl, $C_{1-4}$alkoxy$C_{1-4}$alkyl, —O(CH$_2$)$_m$O— or an additional heteroaromatic group selected from furanyl, pyrrolyl, thienyl, pyrazolyl, imidazolyl, oxazolyl, isoxazolyl, thiazolyl, isothiazolyl, oxadiazolyl, thiadiazolyl, pyridyl or pyridyl substituted by a group selected from halogen, halo$C_{1-6}$alkyl and halo$C_{1-6}$alkoxy (where $R^b$, $R^c$ and m are as previously defined).

Preferably said heteroaromatic radical is optionally substituted by one or two substituents, especially none or one. Particularly preferred substituents include $C_{1-4}$alkyl (especially methyl or tert-butyl), $C_{1-4}$alkoxy (especially methoxy), trifluoromethyl, trifluoromethoxy, phenyl, phenyl substituted by halogen (especially fluorine) and $C_{1-4}$alkyl (especially methyl), benzyl, or thienyl.

As used herein, the term "carbocyclyl" as a group or part of a group means a 3 to 7-membered cycloalkyl radical such as cyclobutyl, cyclopentyl or cyclohexyl, wherein said cycloalkyl radical may be optionally substituted by one, two or three groups independently selected from halogen, hydroxy, $C_{1-6}$alkyl, $C_{1-6}$alkoxy, halo$C_{1-6}$alkyl, halo$C_{1-6}$alkoxy, $NR^7R^8$, phenyl phenyl substituted by a group selected from halogen, halo$C_{1-6}$alkyl and halo$C_{1-6}$alkoxy, benzyl, $NO_2$, cyano, $NR^bR^c$, $SR^b$, $SOR^b$, $SO_2R^b$, $COR^b$, $CO_2R^b$, $CONR^bR^c$, $C_{2-6}$alkenyl, $C_{2-6}$alkynyl, $C_{1-4}$alkoxy$C_{1-4}$alkyl, —O(CH$_2$)$_m$O— or a heteroaromatic group selected from furanyl, pyrrolyl, thienyl, pyrazolyl, imidazolyl, oxazolyl, isoxazolyl, thiazolyl, isothiazolyl, oxadiazolyl, thiadiazolyl, pyridyl or pyridyl substituted by a group selected from halogen, halo$C_{1-6}$alkyl and halo$C_{1-6}$alkoxy (where $R^b$, $R^c$ and m are as previously defined).

Preferably said carbocyclyl group is optionally substituted by one or two substituents, especially none or one. A particularly preferred substituent is phenyl.

As used herein, the term "fused-carbocyclyl" as a group or part of a group means a 3 to 7-membered cycloalkyl radical such as cyclobutyl, cyclopentyl, cyclohexyl, or cycloheptyl, wherein said cycloalkyl radical is fused to an aryl or heteroaryl group as herein defined. Preferably, said fused-carbocylyl group is attached to the remainder of the molecule via a carbon atom of the cycloalkyl radical. Preferably, said cycloalkyl radical is fused to a phenyl or pyridyl ring where said phenyl ring is optionally substituted by a group selected from halogen (especially fluorine) and fluoro$C_{1-4}$alkyl (especially trifluoromethyl), furanyl, pyrrolyl, thienyl, pyrazolyl, imidazolyl, oxazolyl, isoxazolyl, thiazolyl, isothiazolyl, oxadiazolyl, thiadiazolyl, and said pyridyl ring is optionally substituted by a group selected from halogen (especially fluorine) and fluoro$C_{1-4}$alkyl (especially trifluoromethyl). Preferably said cycloalkyl radical is fused to a phenyl ring.

Particular compounds of the invention include:
N-benzyl-N'-isoquinolin-5-ylurea
N-(1,1'-biphenyl-4-ylmethyl)-N'-isoquinolin-5-ylurea
N-(1,1'-biphenyl-3-ylmethyl)-N'-isoquinolin-5-ylurea
N-isoquinolin-5-yl-N'-(3-phenylpropyl)urea;
N-isoquinolin-5-yl-N'-(1,2,3,4-tetrahydronaphthalen-2-ylmethyl)urea;
N-[2-(4-chlorophenyl)ethyl]-N'-isoquinolin-5-ylurea;
N-[3,5-bis(trifluoromethyl)benzyl]-N'-isoquinolin-5-ylurea;
N-[3-(3,4-dimethylphenyl)propyl]-N'-isoquinolin-5-ylurea;
N-(4-tert-butylbenzyl)-N'-isoquinolin-8-ylurea;
N-(4-tert-butylbenzyl)-N'-isoquinolin-5-ylurea;
N-(4-tert-butylbenzyl)-N'-quinolin-5-ylurea;
N-(3-tert-butylbenzyl)-N'-isoquinolin-5-ylurea;
N-[2-(4-tert-butylphenyl)ethyl]-N'-isoquinolin-5-ylurea;
N-isoquinolin-5-yl-N'-[4-(trifluoromethyl)benzyl]urea;
N-isoquinolin-5-yl-N'-[3-(trifluoromethyl)benzyl]urea;
N-isoquinolin-5-yl-N'-{2-[4-(trifluoromethyl)phenyl]ethyl}urea;
N-(2-oxidoisoquinolin-5-yl)-N'-[4-(trifluoromethyl)benzyl]urea;
N-isoquinolin-5-yl-N'-{2-[3-(trifluoromethyl)phenyl]ethyl}urea;
N-isoquinolin-5-yl-N'-{3-[4-(trifluoromethyl)phenyl]propyl}urea;
N-isoquinolin-8-yl-N'-[4-(trifluoromethyl)benzyl]urea;
N-[3-fluoro-4-(trifluoromethyl)benzyl]-N'-isoquinolin-5-ylurea;
N-[2-fluoro-4-(trifluoromethyl)benzyl]-N'-isoquinolin-5-ylurea;
N-isoquinolin-5-yl-N'-{3-[3-(trifluoromethyl)phenyl]propyl}urea;
N-isoquinolin-5-yl-N'-[4-(trifluoromethoxy)benzyl]urea;
N-{[6-(4-fluorophenyl)pyridin-3-yl]methyl}-N'-isoquiolin-5-ylurea;
N-isoquinolin-8-yl-N'-{3-[4-(trifluoromethyl)phenyl]propyl}urea;
N-quinolin-5-yl-N'-{3-[4-(trifluoromethyl)phenyl]propyl}urea;
N-isoquinolin-8-yl-N'-{3-[3-(trifluoromethyl)phenyl]propyl}urea;
N-quinolin-5-yl-N'-{3-[3-(trifluoromethyl)phenyl]propyl}urea;
N-isoquinolin-8-yl-N'-[4-(trifluoromethoxy)benzyl]urea;
N-quinolin-5-yl-N'-[4-(trifluoromethoxy)benzyl]urea;
N-(2,3-dihydro-1H-inden-2-ylmethyl)-N'-isoquinolin-5-ylurea;

N-isoquinolin-5-yl-N'-(4-phenylcyclohexyl)urea;
N-isoquinolin-5-yl-N'-(6,7,8,9-tetrahydro-5H-benzo[α][7]annulen-6-ylmethyl)urea;
N-isoquinolin-5-yl-N'-(6,7,8,9-tetrahydro-5H-benzo[α][7]annulen-7-ylmethyl)urea;
N-isoquinolin-5-yl-N'-{[5-(trifluoromethyl)pyridin-2-yl]methyl}urea;
N-[(4-tert-butylpyridin-2-yl)methyl]-N-isoquinolin-5-ylurea;
N-[(6-tert-butylpyridin-3-yl)methyl]-N-isoquinolin-5-ylurea;
N-[(2-tert-butylpyridin-4-yl)methyl]-N-isoquinolin-5-ylurea;
N-[(6-tert-butylpyridin-2-yl)methyl]-N-isoquinolin-5-ylurea;
N-isoquinolin-5-yl-N'-{[6-(trifluoromethyl)pyridin-3-yl]methyl}urea;
N-isoquinolin-5-yl-N-{3-[6-(trifluoromethyl)pyridin-3-yl]propyl}urea;
N-isoquinolin-5-yl-N-[3-(1H-pyrazol-1-yl)benzyl]urea;
N-isoquinolin-5-yl-N-[4-(1H-pyrazol-1-yl)benzyl]urea;
N-isoquinolin-5-yl-N-[(2-phenyl-1,3-thiazol-5-yl)methyl]urea;
N-isoquinolin-5-yl-N-[(2-thien-2-yl-1,3-thiazol-4-yl)methyl]urea;
N-isoquinolin-5-yl-N'-[(4-phenyl-1,3-thiazol-2-yl)methyl]urea;
N-isoquinolin-5-yl-N'-[(2-phenyl-1,3-thiazol-4-yl)methyl]urea;
N-isoquinolin-5-yl-N'-[2-(4-phenyl-1,3-thiazol-2-yl)ethyl]urea;
N-isoquinolin-5-yl-N'-[(5-phenylisoxazol-3-yl)methyl]urea;
N-isoquinolin-5-yl-N'-[(3-phenylisoxazol-5-yl)methyl]urea;
N-(8-fluoroisoquinolin-5-yl)-N'-[4-(trifluoromethyl)benzyl]urea;
N-isoquinolin-5-yl-N-methyl-N'-[4-(trifluoromethyl)benzyl]urea;
N'-isoquinolin-5-yl-N-methyl-N-[4-(trifluoromethyl)benzyl]urea;
N-isoquinolin-5-yl-N'-{1-[4-(trifluoromethyl)phenyl]ethyl}urea;
N-(1,3-diphenylpropyl)-N'-isoquinolin-5-ylurea;
N-isoquinolin-5-yl-N'-[(3-phenyl-1,2,4-oxadiazol-5-yl)methyl]urea;
N-[(2-benzyl-1,3-thiazol-4-yl)methyl]-N'-isoquinolin-5-ylurea;
N-isoquinolin-5-yl-N-{[1-(2-methylphenyl)-1H-pyrazol-4-yl]methyl}urea;
N-(3-methoxyisoquinolin-8-yl)-N'-[4-(trifluoromethyl)benzyl]urea;
N-cinnolin-5-yl-N'-[4-(trifluoromethyl)benzyl]urea;
N-(4-tert-butylbenzyl)-N'-cinnolin-5-ylurea;
N-(3-cyclohexylpropyl)-N'-isoquinolin-5-ylurea;
N-isoquinolin-5-yl-N'-(6,7,8,9-tetrahydro-5H-benzo[α][7]annulen-7-yl)urea;
N-isoquinolin-5-yl-N'-[4-(trifluoromethyl)benzyl]thiourea;
N-isoquinolin-6-yl-N'-[4-(trifluoromethyl)benzyl]urea;
N-isoquinolin-6-yl-N'-[4-(trifluoromethoxy)benzyl]urea;
N-(3-methylisoquinolin-5-yl)-N'-[4-(trifluoromethyl)benzyl]urea;
N-(1-chloroisoquinolin-5-yl)-N'-[4-(trifluoromethyl)benzyl]urea;
N-[1-(dimethylamino)isoquinolin-5-yl]-N'-[4-(trifluoromethyl)benzyl]urea;
N-(3-methylisoquinolin-5-yl)-N'-[4-(trifluoromethoxy)benzyl]urea;
N-(3-methylisoquinolin-8-yl)-N'-[4-(trifluoromethyl)benzyl]urea;
N-(3-chloroisoquinolin-5-yl)-N'-[4-(trifluoromethyl)benzyl]urea;
N-(3-methylcinnolin-5-yl)-N'-[4-(trifluoromethyl)benzyl]urea;
N-cinnolin-5-yl-N'-[4-(trifluoromethoxy)benzyl]urea;
N-(1-hydroxyisoquinolin-5-yl)-N'-[4-(trifluoromethyl)benzyl]urea;
N-[4-(trifluoromethyl)benzyl]-N'-[3-(trifluoromethyl)isoquinolin-5-yl]urea;
N-(1-chloro-3-ethylisoquinolin-5-yl)-N'-[4-(trifluoromethyl)benzyl]urea;
N-phenyl-N'-[quinolin-6-yl]urea;
N-(2-naphthyl)-N'-[quinolin-6-yl]urea;
N-(4-nitrophenyl)-N'-[quinolin-6-yl]urea;
N-[3,5-bis(trifluoromethyl)phenyl]-N'-[quinolin-6-yl]urea;
N-(4-phenoxyphenyl)-N'-[quinolin-6-yl]urea;
N-(4-acetylphenyl)-N'-[quinolin-6-yl]urea;
N-benzyl-N'-[quinolin-6-yl]urea;
N-[quinolin-6-yl]-N'-[4-(trifluoromethoxy)phenyl]urea;
N-(4-cyanophenyl)-N'-[quinolin-6-yl]urea;
N-(1,1'-biphenyl-4-yl)-N'-[quinolin-6-yl]urea;
N-[4-(dimethylamino)phenyl]-N'-[quinolin-6-yl]urea;
N-(1,3-benzodioxol-5-yl)-N'-[quinolin-6-yl]urea;
N-cyclohexyl-N'-[quinolin-6-yl]urea;
N-[(±)-1-phenylethyl]-N'-[quinolin-6-yl]urea;
N-(1-methylisoquinolin-5-yl)-N'-[4-(trifluoromethyl)benzyl]urea;
N-(1-methylisoquinolin-5-yl)-N'-[4-(trifluoromethoxy)benzyl]urea;
N-(6,8-difluoro-3-methylisoquinolin-5-yl)-N'-[4-(trifluoromethyl)benzyl]urea;
N-[3-methyl-7-(trifluoromethyl)isoquinolin-5-yl]-N'-[4-(trifluoromethyl)benzyl]urea;
N-(8-fluoro-3-methylisoquinolin-5-yl)-N'-[4-(trifluoromethyl)benzyl]urea;
N-(6-fluoro-3-methylisoquinolin-5-yl)-N'-[4-(trifluoromethyl)benzyl]urea;
N-(6-fluoro-3-methyhisoquinolin-5-yl)-N'-[4-(trifluoromethoxy)benzyl]urea;
N-(3-methylcinnolin-5-yl)-N'-[4-(trifluoromethoxy)benzyl]urea;
N-(7-methoxyisoquinolin-5-yl)-N'-[4-(trifluoromethyl)benzyl]urea;
N-(1,3-dimethylisoquinolin-5-yl)-N'-[4-(trifluoromethyl)benzyl]urea;
N-(7-chloro-3-methylisoquinolin-5-yl)-N'-[4-(trifluoromethyl)benzyl]urea;
N-(7-chloroisoquinolin-5-yl)-N'-[4-(trifluoromethyl)benzyl]urea;
N-(8-fluoro-3-methoxyisoquinolin-5-yl)-N'-[4-(trifluoromethyl)benzyl]urea;
N-(6-fluoroisoquinolin-5-yl)-N'-[4-(trifluoromethyl)benzyl]urea;
N-(6-fuoroisoquinolin-5-yl)-N'-[4-(trifluoromethoxy)benzyl]urea;
N-(7-fluoroisoquinolin-5-yl)-N'-[4-(trifluoromethyl)benzyl]urea;
N-(4-methylisoquinolin-5-yl)-N'-[4-(trifluoromethyl)benzyl]urea;
N-[8-(trifluoromethyl)isoquinolin-5-yl]-N'-[4-(trifuoromethyl)benzyl]urea;
N-[6-(trifluoromethylisoquinolin-5-yl]-N'-[4-(trifluoromethyl)benzyl]urea;

N-[7-(trifluoromethyl)isoquinolin-5-yl]-N'-[4-(trifluoromethyl)benzyl]urea;
N-[7-(trifuoromethyl)isoqulinolin-5-yl]-N'-[4-(trifluoromethoxy)benzyl]urea;
N-(6-fluoro-1-methylisoquinolin-5-yl)-N'-[4-(trifluoromethyl)benzyl]urea;
N-(1-cyanoisoquinolin-5-yl)-N'-[4-(trifluoromethyl)benzyl]urea;
N-[1-(methoxycarbonyl)isoquinolin-5-yl]-N'-[4-(trifluoromethyl)benzyl]urea;
N-(1-carboxyisoquinolin-5-yl)-N'-[4-(trifluoromethyl)benzyl]urea;
N-(1-aminoisoquinolin-5-yl)-N'-[4-(trifluoromethyl)benzyl]urea;
N-[1-(hydroxymethyl)isoquinolin-5-yl]-N'-[4-(trifluoromethyl)benzyl]urea;
N-[3-(methoxycarbonyl)isoquinolin-5-yl]-N'-[4-(trifluoromethyl)benzyl]urea;
N-(3-carboxyisoquinolin-5-yl)-N'-[4-(trifluoromethyl)benzyl]urea;
N-[3-(dimethylamino)isoquinolin-5-yl]-N'-[4-(trifluoromethyl)benzyl]urea;
N-[3-(2-aminoethyl)isoquinolin-5-yl]-N'-[4-(trifluoromethyl)benzyl]urea;
N-(8-methoxyisoquinolin-5-yl)-N'-[4-(trifluoromethyl)benzyl]urea;
N-isoquinolin-7-yl-N'-[4-(trifluoromethyl)benzyl]urea;
N-N'-diisoquinolin-5-ylurea;
N-isoquinolin-5-yl-N'-[4-(trifluoromethyl)phenyl]urea;
N-isoquinolin-5-yl-N'-{[2-(trifluoromethyl)pyrimidin-5-yl]methyl}urea;
ethyl 3-{[(isoquinolin-5-ylamino)carbonyl]amino}-2-[4-(trifluoromethyl)benzyl]propanoate;
3-{[(isoquinolin-5-ylamino)carbonyl]amino}-2-[4-(trifluoromethyl)benzyl]propanoic acid;
N-isoquinolin-5-yl-N'-[4-(morpholin-4-ylmethyl)benzyl]urea; and
N-isoquinolin-5-yl-N'-[2-(2-morpholin-4-ylethoxy)-4-(trifluoromethyl)benzyl]urea;

or a pharmaceutically acceptable salt or N-oxide thereof.

In a further aspect of the present invention, the compounds of formula (I) may be prepared in the form of a pharmaceutically acceptable salt, especially an acid addition salt.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulphonic acid, maleic acid, succinic acid, acetic acid, citric acid, tartaric acid, carbonic acid, phosphoric acid or sulphuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the compound of formula (I) with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention also includes within its scope N-oxides of the compounds of formula (I) above. In general, such N-oxides may be formed on any available nitrogen atom, and preferably on any one of A, B, D or E where they represent a nitrogen atom. The N-oxides may be formed by conventional means, such as reacting the compound of formula (I) with oxone in the presence of wet alumina.

The present invention includes within its scope prodrugs of the compounds of formula (I) above. In general, such prodrugs will be functional derivatives of the compounds of formula (I) which are readily convertible iin. vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The present invention includes within its scope solvates of the compounds of formula (I) and salts thereof, for example, hydrates.

The compounds according to the invention may have one or more asymmetric centres, and may accordingly exist both as enantiomers and as diastereoisomers. It is to be understood that all such isomers and mixtures thereof are encompassed within the scope of the present invention. Furthermore, the compounds of formula (I) may also exist in tautomeric forms and the invention includes within its scope both mixtures and separate individual tautomers.

It will be appreciated that the preferred definitions of the various substituents recited herein may be taken alone or in combination and, unless otherwise stated, apply to the generic formula for compounds of the present invention as well as to the preferred classes of compound represented by formula (Ia) and formula (Ib).

The present invention further provides pharmaceutical compositions comprising one or more compounds of formula (I) in association with a pharmaceutically acceptable carrier or excipient.

Preferably the compositions according to the invention are in unit dosage forms such as tablets, pills, capsules, powders, granules, sterile parenteral solutions or suspensions, metered aerosol or liquid sprays, drops, ampoules, auto-injector devices, suppositories, creams or gels; for oral, parenteral, intrathecal, intranasal, sublingual, rectal or topical administration, or for administration by inhalation or insufflation. Oral compositions such as tablets, pills, capsules or wafers are particularly preferred. For preparing solid compositions such as tablets, the principal active ingredient is mixed with a pharmaceutical carrier, e.g. conventional tabletting ingredients such as corn starch, lactose, sucrose, sorbitol, talc, stearic acid, magnesium stearate, dicalcium phosphate or gums, and other pharmaceutical diluents, e.g. water, to form a solid pre-formulation composition containing a homogeneous mixture of a compound of the present invention, or a pharmaceutically acceptable salt thereof. When referring to these pre-formulation compositions as homogeneous, it is meant that the active ingredient is dispersed evenly throughout the composition so that the composition may be readily subdivided into equally effective unit dosage forms such as tablets, pills and capsules. This solid pre-formulation composition is then subdivided into unit dosage forms of the type described above containing from 0.1 to about 500 mg of the active ingredient of the present invention. Favoured unit dosage forms contain from 1 to 500 mg, for example 1, 5, 10, 25, 50, 100, 300 or 500 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of painful conditions such as those listed below, a suitable dosage level is about 1.0 mg to 15 g per day, preferably about 5.0 mg to 5 g per day, and especially about 20 mg to 2 g day. The compounds may be administered on a regimen of 1 to 4 times per day.

It will be appreciated that the amount of a compound of formula (I) required for use in any treatment will vary not only with the particular compounds or composition selected but also with the route of administration, the nature of the condition being treated, and the age and condition of the patient, and will ultimately be at the discretion of the attendant physician.

The invention further provides a compound of formula (I) as defined above, or a pharmaceutically acceptable salt thereof, for use in treatment of the human or animal body. Preferably, said treatment is for a condition which is susceptible to treatment by modulation (preferably antagonism) of VR1 receptors.

The compounds of the present invention will be of use in the prevention or treatment of diseases and conditions in which pain and/or inflammation predominates, including chronic and acute pain conditions. Such conditions include rheumatoid arthritis; osteoarthritis; post-surgical pain; musculo-skeletal pain, particularly after trauma; spinal pain; myofascial pain syndromes; headache, including migraine, acute or chronic tension headache, cluster headache, temporomandibular pain, and maxllary sinus pain; ear pain; episiotomy pain; burns, and especially primary hyperalgesia associated therewith; deep and visceral pain, such as heart pain, muscle pain, eye pain, orofacial pain, for example, odontalgia, abdominal pain, gynaecological pain, for example, dysmenorrhoea, pain associated with cystitis and labour pain; pain associated with nerve and root damage, such as pain associated with peripheral nerve disorders, for example, nerve entrapment and brachial plexus avulsions, amputation, peripheral neuropathies, tic douloureux, atypical facial pain, nerve root damage, and arachnoiditis; itching conditions including pruritus, itch due to hemodialysis, and contact dermatitis; pain (as well as broncho-constriction and inflammation) due to exposure (e.g. via ingestion, inhalation, or eye contact) of mucous membranes to capsaicin and related irritants such as tear gas, hot peppers or pepper spray; neuropathic pain conditions such as diabetic neuropathy, chemotherapy-induced neuropathy and post-herpetic neuralgia; "non-painful" neuropathies; complex regional pain syndromes; pain associated with carcinoma, often referred to as cancer pain; central nervous system pain, such as pain due to spinal cord or brain stem damage, low back pain, sciatica and ankylosing spondylitis; gout; scar pain; irritable bowel syndrome; inflammatory bowel disease; urinary incontinence including bladder detrusor hyper-reflexia and bladder hypersensitivity; respiratory diseases including chronic obstructive pulmonary disease (COPD), chronic bronchitis, cystic fibrosis and asthma; autoimmune diseases; and immunodeficiency disorders.

Thus, according to a further aspect, the present invention provides a compound of formula (I) for use in the manufacture of a medicament for the treatment or prevention of physiological disorders that may be ameliorated by modulating VR1 activity.

The present invention also provides a method for the treatment or prevention of physiological disorders that may be ameliorated by modulating VR1 activity, which method comprises administration to a patient in need thereof of an effective amount of a compound of formula (I) or a composition comprising a compound of formula (I).

According to a further or alternative aspect, the present invention provides a compound of formula (I) for use in the manufacture of a medicament for the treatment or prevention of a disease or condition in which pain and/or inflammation predominates.

The present invention also provides a method for the treatment or prevention of a disease or condition in which pain and/or inflammation predominates, which method comprises administration to a patient in need thereof of an effective amount of a compound of formula (I) or a composition comprising a compound of formula (I).

According to a further aspect of the present invention, it may be desirable to treat any of the aforementioned conditions with a combination of a compound according to the present invention and one or more other pharmacologically active agents suitable for the treatment of the specific condition. The compound of formula (I) and the other pharmacologically active agent(s) may be administered to a patient simultaneously, sequentially or in combination. Thus, for example, for the treatment or prevention of pain and/or inflammation, a compound of the present invention may be used in conjunction with other analgesics, such as acetaminophen (paracetamol), aspirin and other NSAIDs, including selective cyclooxygenase-2 (COX-2) inhibitors, as well as opioid analgesics, especially morphine, NR2B antagonists, bradykinin antagonists, anti-migraine agents, anticonvulsants such as oxcarbazepine and carbamazepine, antidepressants (such as TCAs, SSRIs, SNRIs, substance P antagonists, etc.), spinal blocks, gabapentin, pregabalin and asthma treatments (such as $\beta_2$-adrenergic receptor agonists or leukotriene $D_4$ antagonists (e.g. montelukast).

Specific anti-inflammatory agents include diclofenac, ibuprofen, indomethacin, nabumetone, ketoprofen, naproxen, piroxicam and sulindac, etodolac, meloxicam, rofecoxib, celecoxib, etoricoxib, parecoxib, valdecoxib and tilicoxib. Suitable opioid analgesics of use in conjunction with a compound of the present invention include morphine, codeine, dihydrocodeine, diacetylmorphine, hydrocodone, hydromorphone, levorphanol oxymorphone, alfentanil, buprenorphine, butorphanol, fentanyl, sufentanyl, meperidine, methadone, nalbuphine, propoxyphene and pentazocine; or a pharmaceutically acceptable salt thereof. Suitable anti-migraine agents of use in conjunction with a compound of the present invention include CGEP-antagonists, ergotamines or 5-HT$_1$ agonists, especially sumatriptan, naratriptan, zolmatriptan or rizatriptan.

Therefore, in a further aspect of the present invention, there is provided a pharmaceutical composition comprising a compound of the present invention and an analgesic, together with at least one pharmaceutically acceptable carrier or excipient.

In a further or alternative aspect of the present invention, there is provided a product comprising a compound of the present invention and an analgesic as a combined preparation for simultaneous, separate or sequential use in the treatment or prevention of a disease or condition in which pain and/or inflammation predominates.

According to a general process (A), compounds of formula (I) may be prepared by the reaction of a compound of formula (II) with a compound of formula (III):

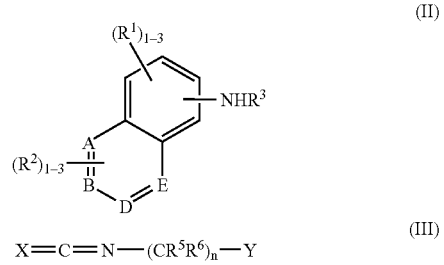

(II)

X=C=N—(CR$^5$R$^6$)$_n$—Y (III)

The reaction is conveniently effected at a temperature between 20° C. and the reflux temperature of the solvent. Suitable solvents include a halogenated hydrocarbon, for example, dichloromethane.

Similarly, according to a general process (B), compounds of formula (I) may also be prepared by the reaction of a compound of formula (IV) with a compound of formula (V):

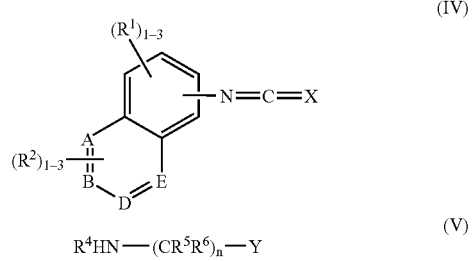

(IV)

R$^4$HN—(CR$^5$R$^6$)$_n$—Y (V)

The reaction is essentially effected in the same manner as general process (A).

According to an alternative general process (C), compounds of formula (I), in which X is an oxygen atom, may be prepared by the reaction of a compound of formula (II) with a compound of formula (VI):

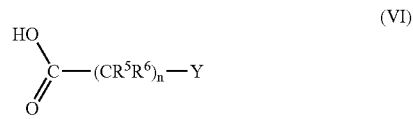

(VI)

The carboxylic acid is first reacted with diphenylphosphoryl azide and triethylamine which forms the corresponding isocyanate by a Curtius rearrangement. The isocyanate may then be reacted in situ with the amine of formula (II) by heating at reflux to give the desired compound of formula (I). The reactions are conveniently effected in a suitable solvent such as an aromatic hydrocarbon, for example, toluene.

Similarly, according to a general process (D), compounds of formula (I), in which X is an oxygen atom, may also be prepared by the reaction of a compound of formula (V) with a compound of formula (VII):

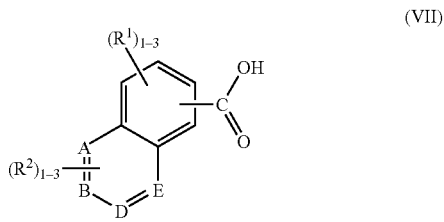

(VII)

The reaction is essentially effected in the same manner as general process (C).

Further details of suitable procedures will be found in the accompanying Examples. For instance, compounds of formula I can be converted into other compounds of formula I utilising synthetic methodology well known in the art. For example, when R$^2$ is a chlorine atom it can be converted to a cyano group using zinc chloride by heating, generally to about 80° C., in the presence of a catalyst such as triphenylphosphine palladium under an inert atmosphere for about three days. When R$^2$ is a carboxylic ester it can be hydrolysed in the presence of a basic catalyst to the carboxylic acid by known methods. This compound can be converted to an amine group utilising diphenylphosphoryl azide, generally in the presence of a base such as triethylamine, a solvent such as dioxane, under an inert atmosphere and with heating to about 100° C. for about 90 minutes, followed by the addition of water, generally with further heating, for about an hour. The carboxylic ester can be selectively reduced to a hydroxymethyl group with lithium borohydride, generally in a solvent, such as a mixture of tetrahydrofuran and toluene, at 60° C. for about 1 h.

Compounds of formulae (III) and (IV) in which X is an oxygen atom may be prepared in situ, as described in general process (C), or they may be prepared from the corresponding carboxylic acid of formulae (VI) and (VII), respectively, by first being converted into the corresponding acyl halide by reaction with, for example, oxalyl chloride. The acyl halide is then converted into the corresponding acyl azide by reaction with, for example, with sodium azide. The desired isocyanate is then obtained by a conventional Curtius rearrangement by heating the acyl azide at reflux. The reactions are conveniently effected in a suitable solvent such as a halogenated hydrocarbon, for example, dichloromethane.

Compounds of formula (II) and (IV) in which X is a sulfur atom may be prepared from the corresponding amine of formula (IV) and (II), respectively (wherein $R^3$ and $R^4$ are hydrogen), by reaction with 1,1'-thiocarbonyl-2(1H)-pyridone. The reaction is conveniently effected at room temperature in a suitable solvent such as a halogenated hydrocarbon, for example, dichloromethane.

Compounds of formulae (II) to (VII) are either known compounds or may be prepared by conventional methodology well known to one of ordinary skill in the art using, for instance, procedures described in the accompanying Examples, or by alternative procedures which will be readily apparent.

For example, compounds of formula II in which B is a nitrogen atom and A, D and E are carbon atoms, one group $R^2$ is present at the 3-position and $R^3$ is hydrogen, can be made by reacting a compound in which the amino group is absent with a mixture of concentrated sulfuric acid and fuming nitric acid at about 0° C. for about 30 minutes followed by reduction of the resultant nitro group for example using hydrogen and lindlar catalyst, in a solvent such as methanol.

This compound can be made by reacting a compound of formula VIII:

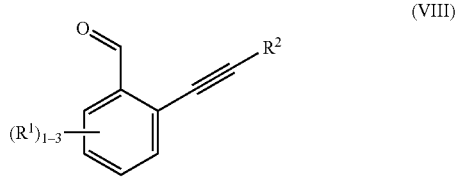

(VIII)

in which $R^1$ is as defined above with ammonia, generally at about 80° C. for about 5 hours, at a pressure of about 35 psi in a Parr apparatus.

The compound of formula VIII can be made by successively reacting a compound of formula IX:

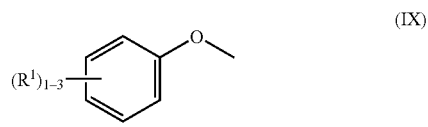

(IX)

in which $R^1$ is as defned above with a carbonylating agent such as dichloromethyl methylether in a solvent such as dichloromethane in the presence of a catalyst such as titanium tetrachloride at about room temperature for about an hour. The methoxy group is converted to a hydroxy group using a reagent such as borontribromide in a solvent such as dichloromethane at about room temperature for several hours. This compound is optionally activated, for example by forming the trifluoromethylsulfonate using trifluoromethanesulfonic anhydride generally in the presence of a base such as triethylamine and a solvent such as dichlorometlhane for about one hour at room temperature. This compound is reacted with a solution of a compound of formula X:

(X)

in which $R^2$ is as defined above, which solvent is generally DMF, in the presence of a base such as triethylamine and preferably catalysts such as dichlorodi(triphenylphosphine) palladium at about room temperature for two to four hours. An alternative activation can also occur by making the bromide in place of the trifluoromethane sulfonate.

The carbonyl moiety in the compounds of formula VIII can also be produced by selectively reducing a carboxylic acid moiety using a reagent such as borane tetrahydrofuran complex in tetrahydrofuran, at about room temperature for about 4 hours, to the alcohol followed by selective oxidation to the aldehyde using, for example, oxalyl chloride in DMSO in a solvent such as dichloromethane at about room temperature for about an hour.

Compounds of formula II in which one group $R^2$ is present at the 3-position, B is nitrogen and A, D and E are carbon can also be made by reacting a compound of formula (XI):

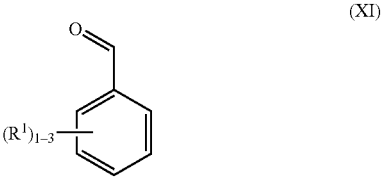

(XI)

in which $R^1$ is as defined above, with the acetal of a compound of formula $H_2NCBR^2CHO$, in which $R^2$ is as defined above, generally at reflux for about 2 hours under Dean/Stark conditions followed by the addition of an acid such as concentrated sulfuric acid at a temperature of about 140° C. for about 30 minutes.

Compounds of formula II in which an alkyl group is present at the 1-position can be made by the following sequence. A compound of formula (XII):

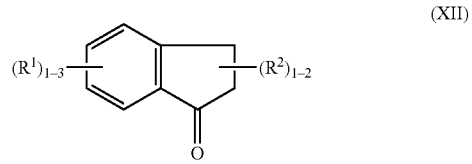

(XII)

in which $R^1$ and $R^2$ are as defined above, is reacted with an alkylating agent, such as the appropriate Grignard reagent, generally in a solvent such as tetrahydrofuran for several hours at about room temperature followed by elimination of water under acidic conditions, to produce the corresponding indene. This is converted to the corresponding epoxide, for example using ozone at a temperature of about −78° C. for about 9½ hours. This is followed by reacting with ammonium hydroxide at about room temperature for about 2 days to produce the isoquinoline which is then nitrated and reduced to produce the amine.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene and P. G. M. Wuts, *Protective Groups in Organic Synthesis*, John Wiley & Sons, 1991. The protecting groups may be removed at a convenient subsequent stage using methods known from the art.

The following non-limiting Examples serve to illustrate the preparation of compounds of the present invention:

The structures of the products of the following Descriptions and Examples were in most cases confirmed by $^1$H NMR.

DESCRIPTION 1

2-Cyano-5-(trifluoromethyl)pyridine

To an ice-cooled solution of 5-(trifluoromethyl)pyridin-2-ol (10.24 g, 62.8 mmol) in anhydrous dichloromethane (200 ml) was added triethylamine (9.63 ml, 69 mmol), followed by dropwise addition of trifluoromethanesulfonic anhydride (12.68 ml, 75.4 mmol). The resulting mixture was stirred at room temperature for 2 hours. The mixture was washed with water (500 ml) and the aqueous layer extracted with dichloromethane (2×100 ml). The combined organic layers were washed with water (2×300 ml), brine (150 ml), then dried over $Na_2SO_4$, filtered through a 1 inch plug of silica gel and evaporated. The residue was dissolved in anhydrous N,N-dimethylformamide (150 ml) and zinc cyanide (3.98 g, 33.9 mmol) was added followed by tetrakis(triphenylphosphine)palladium(0) ($Pd(PPh_3)_4$) (3.56 g, 3.09 mmol). The mixture was degassed and heated at 80° C. overnight. The cooled reaction mixture was diluted with water (600 ml) and extracted with ethyl acetate (3×150 ml). The combined organic layers were washed with water (2×250 ml), brine (150 ml), dried ($Na_2SO_4$) and evaporated. The residue was purified by column chromatography on silica eluting with a gradient rising from neat iso-hexanes to 10% $Et_2O$ in iso-hexanes to give the title compound (8 g, 75%) as a white solid.

DESCRIPTION 2

2-Aminomethyl-5-(trifluoromethyl)pyridine

To a nitrogen flushed solution of 2-cyano-5-(trifluoromethyl)pyridine (Description 1; 8.0 g, 46.5 mmol) in a mixture of ethanol (100 ml) and ammonium hydroxide (25 ml) was added a spatula end of Raney Nickel and the resulting mixture hydrogenated at 50 psi overnight. The catalyst was removed by filtration and the filtrate was evaporated to dryness. The residue was purified by column chromatography on silica eluting with a gradient rising from 2% MeOH in dichloromethane+0.5% $NH_4OH$ to 5% MeOH in dichloromethane+0.5% $NH_4OH$ to give the title compound (2.5 g, 30%) as a yellow oil.

DESCRIPTION 3

4-tert-Butylpyridine-N-Oxide

To a solution of 4-tert-butylpyridine (44.3 ml, 300 mmol) in glacial acetic acid (200 ml) was added hydrogen peroxide (37.1 ml of a 27.5% aqueous solution, 300 mmol), and the resulting mixture heated at reflux overnight. The cooled mixture was evaporated to dryness. The residue was dissolved in dichloromethane (200 ml), and washed with brine (50 ml), then dried ($Na_2SO_4$) and evaporated to give the title compound (40 g, 88%) as a white solid.

DESCRIPTION 4

2-Cyano-4-tert-butylpyridine

To trimethylsilylcyanide (25.0 ml, 187.5 mmol) was added a solution of 4-tert-butylpyridine-N-oxide (Description 3; 22.68 g, 150 mmol) in anhydrous dichloromethane (200 ml). To this mixture was added dropwise a solution of dimethyl carbamoyl chloride (17.26 ml, 187.5 mmol) in anhydrous dichloromethane (50 ml). The reaction mixture was stirred at room temperature for 24 hours. A solution of 10% aqueous $K_2CO_3$ (200 ml) was added dropwise and the resulting mixture stirred for 10 minutes. The organic layer was separated and the aqueous layer extracted with 2 further portions of dichloromethane (100 ml). The combined organic layers were dried ($Na_2SO_4$) and evaporated to give the title compound (24 g, 100%).

DESCRIPTION 5

2-Aminomethyl-4-tert-butylpyridine

A solution of 2-cyano-4-tert-butylpyridine (Description 4; 24.0 g, 150 mmol) was hydrogenated according to the method of Description 2. Following removal of the catalyst, the residue was taken up in dichloromethane (300 ml) and washed with brine, dried over $K_2CO_3$, filtered and evaporated. The residue was purified by column chromatography on silica eluting with 5% MeOH in dichloromethane+0.5% $NH_4OH$ to give the title compound (12 g, 48%) as a pale yellow oil.

DESCRIPTION 6

2-[4-(Trifluoromethyl)phenyl]ethylamine

A solution of [4-(trifluoromethyl)phenyl]acetonitrile (9.98 g, 53.9 mmol) was hydrogenated according to the method of Description 2. Following removal of the catalyst, the residue was purified by column chromatography on silica eluting with 4% MeOH in dichloromethane+0.5% $NH_4OH$ to give the title compound (6.5 g, 63%) as an orange oil.

DESCRIPTION 7

3-tert-Butylphenyl trifluoromethane sulfonate

To an ice-cooled solution of 3-tert-butylphenol (10 g, 66.6 mmol) and triethylamine (13.92 ml, 99.9 mmol) in anhydrous dichloromethane (100 ml) under an atmosphere of nitrogen was added slowly trifluoromethanesulfonic anhydride (12.30 ml, 73.26 mmol), and the resulting mixture stirred at room temperature for 2 hours. The mixture was then washed with 1N HCl (100 ml), brine (100 ml), dried ($Na_2SO_4$) and evaporated. The residue was purified by column chromatography on silica eluting with iso-hexanes to give the title compound (16.38 g, 87%) as a clear oil.

DESCRIPTION 8

3-tert-Butylbenzonitrile

To a solution of 3-tert-butylphenyl trifuoromethane sulfonate (Description 7; 16.37 g, 58 mmol) in anhydrous N,N-dimethylformamide (200 ml) was added zinc cyanide (8.17 g, 69.6 mmol), and $Pd(PPh_3)_4$ (3.35 g, 2.9 mmol) and the mixture was then degassed ($N_2$) and heated at 80° C. overnight. The cooled reaction mixture was poured into water (750 ml), and extracted with ethyl acetate (3×200 ml). The combined organic layers were washed with water (2×300 ml), brine (200 ml), dried ($Na_2SO_4$), filtered through a 1 cm plug of silica and evaporated to give the title compound (7 g, 76%).

DESCRIPTION 9

3-tert-Butylbenzylamine

A solution of 3-tert-butylbenzonitrile (Description 8; 7.0 g, 44 mmol) was hydrogenated according to the method of Description 2. Following removal of the catalyst, the residue was taken up in dichloromethane (100 ml), washed with brine, dried ($Na_2SO_4$), filtered through a short plug of silica and evaporated to give the title compound (5.2 g, 72%) as a red oil.

DESCRIPTION 10

2-tert-Butyl-5-cyanopyridine

To a mixture of 3-cyanopyridine (10 g, 96 mmol), trimethylacetic acid (9.8 g, 96 mmol) and silver nitrate (1.63 g, 9.6 mmol) in 10% aqueous sulfuric acid (100 ml) at 70° C. was added dropwise a solution of ammonium peroxodisulfate (21.9 g, 96 mmol) in water (120 ml). After complete addition the mixture was stirred at 70° C. for 2 hours. The mixture was cooled and basified by the addition of 33% aqueous $NH_4OH$, and extracted with ethyl acetate (3×100 ml). The combined organic layers were washed with brine (100 ml), dried ($Na_2SO_4$) and evaporated to give the title compound (15.6 g, 100%).

DESCRIPTION 11

3-Aminomethyl-6-tert butylpyridine

A solution of 2-tert-butyl-5-cyanopyridine (Description 10; 15.5 g, 97 mmol) was hydrogenated according to the method of Description 2. Following removal of the catalyst, the residue was purified by column chromatography on silica eluting with 5% MeOH in dichloromethane+0.5% $NH_4OH$ to give the title compound (10.5 g, 66%), as a pale yellow oil.

DESCRIPTION 12

2-tert-Butyl-4-cyanopyridine

A mixture of 4-cyanopyridine (10 g, 96 mmol), trimethylacetic acid (9.8 g, 96 mmol), and silver nitrate (1.63 g, 9.6 mmol) in 10% aqueous sulfuric acid (100 ml) at 70° C. was treated with a solution of ammonium peroxodisulfate (21.9 g, 96 mmol) in water (120 ml) according to the method of Description 10. Purification by column chromatography on silica eluting with 10% $Et_2O$ in iso-hexanes gave the title compound (6.5 g, 42%).

DESCRIPTION 13

4-Aminomethyl-2-tert-butylpyridine

A solution of 2-tert-butyl-4-cyanopyridine (Description 12; 6.50 g, 40.6 mmol) was hydrogenated according to the method of Description 2. Following removal of the catalyst, the residue was taken up in dichloromethane (100 ml), washed with brine, dried ($Na_2SO_4$), filtered through a short plug of silica and evaporated to give the title compound (6.1 g, 91%) as a brown oil.

DESCRIPTION 14

2-Bromo-6-tert-butylpyridine

To potassium tert-butoxide (1.0M in tert butanol, 100 ml, 100 mmol) was added 2,6-dibromopyridine (15.87 g, 67 mmol), and the resulting mixture heated at reflux for 3.5 hours. The mixture was evaporated and the residue quenched by the addition of water (150 ml). The mixture was extracted with ethyl acetate (3×80 ml) and the combined organic layers washed with brine (100 ml), dried ($Na_2SO_4$) and evaporated. The residue was purified by column chromatography on silica eluting with 2% $Et_2O$ in iso-hexanes to give the title compound (9.9 g, 69%) as a clear oil.

DESCRIPTION 15

2-tert-Butyl-6-cyanopyridine

To a solution of 2-bromo-6-tert-butylpyridine (Description 14; 9.9 g, 46 mmol) in anhydrous N,N-dimethylformamide (130 ml) was added zinc cyanide (6.48 g, 55.2 mmol) and $Pd(PPh_3)_4$ (2.65 g, 2.3 mmol). The mixture was degassed then heated at 80° C. overnight. The cooled reaction mixture was poured into water (500 ml), and extracted with ethyl acetate (3×150 ml). The combined organic layers were washed with water (2×300 ml), brine (100 ml), dried ($Na_2SO_4$) and evaporated. The residue was purified by column chromatography on silica eluting with 5% $Et_2O$ in iso-hexanes to give the title compound (6.6 g, 89%).

DESCRIPTION 16

2-Aminomethyl-6-tert-butylpyridine

A solution of 2-tert-butyl-6-cyanopyridine (Description 15, 6.6 g, 41.2 mmol) was hydrogenated according to the method of Description 2. Following removal of the catalyst, the residue was taken up into dichloromethane (300 ml) and washed with brine, dried over $K_2CO_3$, filtered and evaporated. The residue was purified by column chromatography on silica eluting with 5% MeOH in dichloromethane+0.5% $NH_4OH$ to give the title compound (4.5 g, 66%) as a pale orange oil.

DESCRIPTION 17

(E/Z)-3-[6-(Trifluoromethyl)pyridin-3-yl]prop-2-enenitrile

To an ice-bath cooled suspension of sodium hydride (1.26 g of a 60% dispersion, 31.46 mmol) in anhydrous THF (75 ml) was added dropwise a solution of diethyl cyanomethylphosphonate (5.09 ml, 31.46 mmol) in THF (50 ml). After the addition was complete the mixture was stirred for 10 minutes then a solution of 6-(trifluoromethyl)pyridine-3-carboxaldehyde (5.00 g, 28.6 mmol) in THF (25 ml) was added and the resulting mixture stirred at room temperature for 1 hour. Water (250 ml) was added and the mixture extracted with ethyl acetate (3×100 ml). The combined organic layers were washed with water (×2), brine, dried (Na$_2$SO$_4$) and evaporated. The residue was purified by column chromatography on silica eluting with a gradient rising from 10% EtOAc in isohexanes to 30% EtOAc in iso-hexanes to give the title compound—E and Z isomers were separated but then re-combined (5.6 g, 100%).

DESCRIPTION 18

3-[6-(Trifuoromethyl)pyridin-3-yl]propylamine

A solution of (E/Z)-3-[6-(trifluoromethyl)pyridin-3-yl]prop-2-enenitrile (Description 17; 5.60 g, 28.3 mmol) was hydrogenated according to the method of Description 2. Following removal of the catalyst, the residue was purified by column chromatography on silica eluting with 5% MeOH in dichloromethane+0.5% NH$_4$OH to give the title compound (3.5 g, 57%).

DESCRIPTION 19

1,2,3,4-Tetrahydronaphthalene-2-carboxamide

To a suspension of 1,2,3,4-tetrahydronaphthalene-2-carboxylic acid (6.08 g, 34.5 mmol) in anhydrous dichloromethane (60 ml) was added oxalyl chloride (4.52 ml, 51.8 mmol), followed by 2 drops of N,N-dimethylformamide and the resulting mixture was stirred at room temperature for 2 hours. The mixture was evaporated to dryness, toluene (50 ml) was then added and the mixture evaporated to dryness again. The residue was dissolved in anhydrous dichloromethane (100 ml) and added in one portion to dichloromethane (150 ml) which had been saturated with ammonia gas. The resulting mixture was stirred at room temperature for 48 hours. The mixture was evaporated to dryness and the residue partitioned between ethyl acetate (150 ml) and water (250 ml). The aqueous layer was further extracted with ethyl acetate (100 ml). The combined organic layers were washed with water (200 ml), brine (100 ml), then dried (Na$_2$SO$_4$) and evaporated to give the title compound (6 g, 99%) as a white solid.

DESCRIPTION 20

1,2,3,4-Tetrahydronaohthalen-2-ylmethylamine

To an ice-bath cooled solution of 1,2,3,4-tetrahydronaphthalene-2-carboxamide (Description 19; 5.99 g, 34.2 mmol) in anhydrous THF (150 ml) was added in portions lithium aluminum hydride (2.6 g, 68.4 mmol). After complete addition, the mixture was heated to reflux for 3 hours then cooled in an ice bath and quenched carefully by the sequential addition of water (2.74 ml), 4N NaOH (2.74 ml) and water (8.2 ml). The resulting suspension was stirred for 10 minutes, then filtered through Celitem and the filtrate evaporated to give the title compound (4.5 g, 81%).

DESCRIPTION 21

(2E/Z)-3-[4-(Trifluoromethyl)phenyl]prop-2-enenitrile

To a solution of 4-trifluoromethyliodobenzene (7.23 g, 26.6 mmol) in anhydrous acetonitiile (130 ml) was added triethylamine (3.74 ml, 26.6 mmol), acrylonitrile (1.77 ml, 26.6 mmol), palladium (II) acetate (60 mg, 0.26 mmol), and tri-o-tolylphosphine (324 mg, 1.06 mmol) and the resulting mixture heated at reflux overnight. The cooled reaction mixture was filtered through Celite™, and partitioned between water and ethyl acetate. The organic layer was separated and washed with brine, dried (Na$_2$SO$_4$) and evaporated. The residue was purified by column chromatography on silica eluting with 5% EtOAc in iso-hexanes to give the title compound (4.07 g, 78%).

DESCRIPTION 22

3-[4-(Trifluoromethyl)phenyl]propylamine

A solution of (2E/Z)-3-[4-(trifluoromethyl)phenyl]prop-2-enenitrile (Description 21; 4.06 g, 20.6 mmol) was hydrogenated according to the method of Description 2. Following removal of the catalyst, the residue was purified by column chromatography on silica eluting with 4% MeOH in dichloromethane+0.5% NH$_4$OH to give the title compound (3.5 g, 83%) as an oil.

DESCRIPTION 23

3-[3-(Trifluoromethyl)phenyl]propylamine

To an ice-bath cooled suspension of sodium hydride (1.32 g of a 60% dispersion in oil, 33 mmol) in anhydrous tetrahydrofuran (100 ml) under a nitrogen atmosphere was added dropwise a solution of diethyl cyanomethylphosphonate (5.34 ml, 33 mmol) in tetrahydrofuran (40 ml) and the resulting mixture stirred at 0° C. for 15 minutes. To this mixture was added a solution of 3-trifluoromethylbenzaldehyde (5.22 g, 30 mmol) in anhydrous tetrahydrofuran (40 ml) and the resulting mixture stirred at room temperature for 1.5 hours. Water (300 ml) was added and the mixture extracted with ethyl acetate (3×150 ml). The combined organic layers were washed with water (2×200 ml), brine (150 ml) then dried (Na$_2$SO$_4$) and evaporated. The residue was taken up in a mixture of ethanol (100 ml) and ammonium hydroxide (25 ml) and hydrogenated according to the method of Description 2. Purification by column chromatography on silica eluting with 5% MeOH in dichloromethane+0.5% NH$_4$OH gave the title compound (1.5 g, 25%) as a yellow oil.

DESCRIPTION 24

6-(4-Fluorophenyl)nicotinamide

A mixture of 6-chloronicotinamide (5.00 g, 31.95 mmol), 4-fluorobenzene boronic acid (4.92 g, 35.14 mmol), and Pd(PPh$_3$)$_4$(1.10 g, 0.96 mmol) in a mixture of toluene (80 ml), ethanol (12 ml) and 2M sodium carbonate (36.74 ml, 73.48 mmol) was degassed (N$_2$) and heated at 100° C. for 18 hours. The reaction mixture was cooled to room temperature and then filtered. The collected solid was washed with water and dried. The dried solid was taken up in methanol (100 ml) and heated to reflux for 20 minutes. The mixture was then cooled to room temperature, filtered and the solid dried to give the title compound (6.25 g, 90%) as a pale grey solid.

DESCRIPTION 25

[6-(4-Fluorophenyl)pyridin-3-yl]methylamine

To an ice-bath cooled solution of sodium borohydride (5.47 g, 144.5 mmol) in anhydrous 1,4-dioxane (100 ml) was added slowly a solution of glacial acetic acid (8.27 ml, 144.5 mmol) in 1,4-dioxane (50 ml). To this mixture was added 6-(4-fluorophenyl)nicotinamide (Description 24; 6.25 g, 28.9 mmol) and the resulting mixture heated at reflux for 4 hours. The cooled reaction mixture was evaporated and water (60 ml) added slowly. This mixture was extracted with dichloromethane, and the solid which appeared between the layers was removed by filtration. This solid was triturated with a mixture of dichloromethane and iso-hexanes, filtered and dried to give the title compound (510 mg, 8%) as a pale green solid.

DESCRIPTION 26

6,7,8,9-Tetrahydro-5H-benzo[α][7]annulen-6-ylm-ethylamine hydrochloride

To a nitrogen flushed solution of methyl 6,7-dihydro-5H-benzo[α][7]annulene-8-carboxylate [*J. Org. Chem.* 1991, 56, 6199-6205] (54.8 g, 271 mmol) in a mixture of ethyl acetate (250 ml) and glacial acetic acid (5 ml) was added 10% palladium on carbon (10 g) and the mixture was hydrogenated at 55 psi for 16 hours. The catalyst was removed by filtration, and the filtrate evaporated to dryness. The residue was dissolved in ethanol (55 ml) and 3M aqueous NaOH (165 ml, 495 mmol) was added, then the resulting mixture heated to reflux for 2 hours. The mixture was cooled and the ethanol removed by evaporation. The aqueous phase was washed with dichloromethane (×3) then acidified to pH=1 with 6M HCl and extracted with dichloromethane (×3). The combined organic phases from the acidic extraction were dried over $MgSO_4$, filtered and evaporated. The residue was triturated with tert-butyl methyl ether, filtered and dried to give 6,7,8,9-tetrahydro-5H-benzo[α][7]annulene-6-carboxylic acid (20.6 g, 40%). This material was dissolved in dichloromethane (100 ml) containing N,N-dimethylformamide (0.5 ml) and oxalyl chloride (9.68 ml, 111 mmol) dropwise at such a rate that the internal temperature did not rise above 10° C. The mixture was stirred at 5° C. for 30 minutes, then treated dropwise with 33% aqueous ammonium hydroxide (100 ml) whilst maintaining the temperature below 15° C. The resulting slurry was then stirred at 10° C. for 30 minutes. The mixture was evaporated and the residue diluted with water and slurried at 0° C. for 15 minutes. The resulting white solids were filtered, washed with more water, hexanes, and dried to give 6,7,8,9-tetrahydro-5H-benzo[α][7]annulene-6-carboxamide (11.6 g, 55%). This material was dissolved in anhydrous THF and added dropwise over 60 minutes to a slurry of $LiAlH_4$ (3.24 g, 85.4 mmol) in refluxing THF. The reaction was maintained at reflux for 2 hours then cooled to 10° C., diluted with tert-butyl methyl ether, and cautiously quenched by the addition of water while the temperature was maintained below 30° C. The resulting gummy solid was removed by filtration and the phases were then separated. The aqueous phase was washed with tert-butyl methyl ether and the combined organic phases were dried over $MgSO_4$, filtered and evaporated. The residue was dissolved in iso-propyl alcohol (30 ml), cooled to 0° C. and concentrated HCl was added dropwise causing a thick slurry to form. The slurry was concentrated and the residue reconstituted with tert-butyl methyl ether and stirred at 40° C. for 15 minutes. The mixture was cooled to 25° C., filtered and the resulting solids washed with tert-butyl methyl ether and dried to give the title compound.

DESCRIPTION 27

7-(Nitromethyl)-6,7,8,9-tetrahydro-5H-benzo[α][7]annulene

A solution of 8,9-dihydro-5H-benzo[α][7]annulen-5-one (323 g, 2 mol) in nitromethane (620 ml) was treated with DBU (327 g, 2.1 mol) dropwise at such a rate that the temperature was maintained between 40 and 50° C. After GC analysis showed reaction completion, 3M HCl (600 ml) was added and the resulting mixture was extracted with tert-butyl methyl ether (2×500 ml). The combined organic phases were treated with brine (500 ml), dried over $MgSO_4$, filtered and evaporated to an oil (496 g, 90%). To 347.5 g (1.58 mol) of this material dissolved in TFA (1045 ml) was added triethylsilane (583 ml, 3.65 mol) at such a rate that the temperature of the reaction mixture was maintained between 50 and 55° C. After the addition was complete, the mixture was maintained at 55° C. until GC analysis indicated reaction complete. The mixture was poured onto ice (1500 g) and water (500 ml). The resulting slurry was filtered and washed with cold hexanes (2×150 ml) then dried to give the title compound (139 g, 42%).

DESCRIPTION 28

6,7,8,9-Tetrahydro-5H-benzo[α][7]annulen-7-ylm-ethylamine hydrochloride

A mixture of 7-(nitromethyl)-6,7,8,9-tetrahydro-5H-benzo[α][7]annulene (Description 27; 48.6 g, 0.24 mol) and Ra—Ni (50 g) in ethanol (600 ml) was hydrogenated at 60 psi for 12 hours. An additional charge of Ra—Ni (50 g) was added and the mixture was hydrogenated until GC analysis indicated the reaction was complete. The resulting mixture was filtered over Celite™ and washed with ethanol (200 ml). The filtrate was treated with concentrated HCl (35 ml, 0.42 mol) and concentrated under reduced pressure. The product was then slurried in tert-butyl methyl ether (100 ml) and cooled between 0 and 5° C., filtered and washed with tert-butyl methyl ether (100 ml) and dried to give the title compound (21 g, 42%).

DESCRIPTION 29

3-(1H-Pyrazol-1-yl)benzylamine hydrochloride

To a suspension of 3-(1H-pyrazol-1-yl)-benzoic acid [see WO 00/21951] (104 g, 0.55 mol) in anhydrous benzene (500 ml) was added thionyl chloride (85 g, 0.715 mol) and DMF (0.5 ml). The mixture was heated at reflux for 3 hours, then evaporated under reduced pressure. The residue was dissolved in anhydrous THF (100 ml) and evaporated. The residue was dissolved in anhydrous acetone (600 ml), and treated with ammonium acetate (77 g, 1 mol). The mixture was heated at reflux for 12 hours, solvent was evaporated and the residue treated with cold water (2000 ml). The resulting precipitate was filtered, washed with cold water (200 ml) and recrystallised from absolute ethanol (600 ml)

to give 3-(1H-pyrazol-1-yl)benzamide (82 g, 80%). A solution of this material (82 g, 0.44 mol) in THF was added dropwise to a solution of LiAlH$_4$ (25 g, 0.66 mol) in anhydrous THF (800 ml). The mixture was heated at reflux for 4 hours, cooled and quenched by the sequential addition of water (25 ml), 15% aqueous NaOH (25 ml), and water (50 ml). The inorganic by-products were filtered off and washed several times with diethyl ether (overall volume 1000 ml). The combined filtrates were dried over Na$_2$SO$_4$, filtered and evaporated. The residue was dissolved in methanol (400 ml), the solution was treated with activated carbon (10 g), and the mixture was refluxed for 40 minutes, then filtered and evaporated. The residue was treated with 1N HCl in ether (1000 ml), and the precipitate formed was filtered, washed with ether and dried to give the title compound (53 g, 70%).

DESCRIPTION 30

4-(1H-Pyrazol-1-yl)benzylamine hydrochloride

The title compound was prepared from 4-(1H-pyrazol-1-yl)-benzoic acid in an analogous procedure to that detailed in Description 29.

DESCRIPTION 31

N-Methyl-N-[4-(trifluoromethyl)benzyl]amine

A mixture of 4-(trifluoromethyl)benzylamine (1.0 mL, 7.02 mmol) and di-tert-butyl carbonate (1.68 g, 7.72 mmol) in CH$_2$Cl$_2$ (10 mL) was stirred for 1 hour. The reaction mixture was poured into saturated aqueous ammonium chloride solution, extracted with CH$_2$Cl$_2$ and the organic layers were combined, dried over MgSO$_4$ and concentrated in vacuo to give a white crystalline solid. To a solution of the crude carbamate (1.00 g, 3.61 mmol) in THF (20 mL) in a room temperature water bath, was added LiAlH$_4$ (0.69 g, 18.1 mmol) portion-wise over 10 minutes. The reaction was then heated at reflux for 4 hours. The reaction was cooled in ice and quenched by the addition of water (1.6 mL) and NaOH (2N, 1.3 mL). The grey slurry was filtered and washed with MeOH. The MeOH was removed in vacuo and the crude product taken up in CH$_2$Cl$_2$ and dried over MgSO$_4$ and concentrated in vacuo. Purification by flash column chromatography eluting with 5-10% MeOH in CH$_2$Cl$_2$ plus 1% NH$_3$ solution (2N in MeOH) afforded the title compound.

DESCRIPTION 32

1-[4-(Trifluoromethyl)phenyl]ethylamine

To a suspension of NaCNBH$_4$ (0.48 g, 7.6 mmol) and 3 Å molecular sieves (4 g) in MeOH (15 mL) was added NH$_4$OAc (6.15 g, 80 mmol) and 4-(trifluoromethyl)acetophenone (1.5 g, 8.0 mmol). The reaction was stirred at room temperature under nitrogen for 3 days. The reaction was concentrated in vacuo and the pH adjusted to pH 12 by the addition of aqueous NaOH (2N). The reaction was extracted with ethyl acetate and the organic layers combined, dried over MgSO$_4$ and the solvent removed in vacuo. Purification by flash column chromatography, eluting with 5% MeOH in CH$_2$Cl$_2$ afforded the title compound.

DESCRIPTION 33

1,3-DiPhenylpropylamine

The title compound was prepared from 1,3-diphenylpropan-1-one in an analogous procedure to that detailed in Description 32.

DESCRIPTION 34

(3-Phenyl-1,2,4-oxadiazol-5-yl)methylamine hydrochloride

A mixture of 5-chloromethyl-3-phenyl-1,2,4-oxadiazole [*Synth. Commun.* 1992, 22, 209] (90 g, 0.5 mol) and potassium iodide (45 g) was added as one portion to a suspension of potassium phthalimide (90 g, 0.5 mol) in DMSO (400 ml) under intensive stirring. After self-heating ceased, the mixture was heated at 130° C. for 15 minutes, cooled, and poured into water (2.5 l). The precipitate was filtered, washed with water, and dried in the air. Recrystallization from 5% DMSO in ethanol (1 l) afforded 100 g of solid. A suspension of this solid (100 g, 0.33 mol) in ethanol (2 l) was treated with glyme (0.5 l), heated to 35-40° C., treated with hydrazine hydrate (18 g, 0.35 mol), and heated to reflux for 2 hours. The mixture was diluted with concentrated hydrochloric acid (100 ml), and refluxed for 4 hours. After cooling the mixture was filtered, extracted with ether, and evaporated. The residue was dissolved in the minimum volume of water, basified and taken up in ether (300 ml). The organic layer was separated, dried over anhydrous magnesium sulfate, and evaporated. The residue was dissolved in the minimum volume of water, neutralized with hydrochloric acid and evaporated. The crude product was recrystallized twice from isopropanol and dried to give the title compound (21 g, 20%).

DESCRIPTION 35

(2-Benzyl-1,3-thiazol-4-yl)methylamine

2-Benzyl-4-chloromethylthiazole [*Pharmazie* 1972, 27, 146] (223.7 g, 1 mol) was stirred with liquid ammonia (600 ml) in an autoclave for 24 hours. The ammonia was removed and the product was distilled in vacuo [bp (0.02 mmHg) 141-144° C.] to give the title compound (102 g, 50%).

DESCRIPTION 36

[1-(2-Methylphenyl)-1H-pyrazol-4-yl]methylamine

A mixture of 1-(2-tolyl)-pyrazole-4-carboxaldehyde [see U.S. Pat. No. 4,220,792] (186 g, 1 mol), hydroxylamine hydrochloride (104.2 g, 1.5 mol), and sodium acetate trihydrate (204 g) in ethanol (2 l) was refluxed for 1 hour. The mixture was cooled, diluted with water (8 l), and left overnight. The precipitate was filtered to give 1-(2-tolyl)-pyrazole oxime (186 g, 92.5%). Tolylpyrazole oxime (50.3 g, 0.25 mol) in methanol (600 ml) and ammonia (200 ml) was hydrogenated in an autoclave in the presence of Raney nickel (10 g of ethanolic suspension) at 50° C. at 70 atm. The catalyst was filtered off and washed with methanol. The filtrate was evaporated, and the residue was distilled in vacuo to give the title compound (43 g, 92%).

DESCRIPTION 37

3-Cyclohexylpronylamine hydrochloride

To a solution of 3-phenyl-1-propylamine (5.26 ml, 0.04 mol) in ethanol (100 ml) under nitrogen was added concentrated HCl (3 ml) and platinum oxide (0.5 g, 0.002 mol). This was placed on a Parr apparatus and hydrogenated at 50 psi for 5 days. Platinum oxide (0.5 g, 0.002 mol) was added and the mixture hydrogenated for a further 5 days. The mixture was filtered and evaporated to give the title compound (6.4 g, 98%).

DESCRIPTION 38

6,7,8,9-Tetrahydro-5H-benzo[α][7]annulene-7-carboxylic acid

A solution of 7-(nitromethyl)-6,7,8,9-tetrahydro-5H-benzo[α][7]annulene (Description 27; 96 g, 0.47 mol) in THF (550 ml) was cooled to −18° C. and potassium tert-butoxide (1.6M in THF, 263 ml, 0.42 mol) was added dropwise over 30 minutes while maintaining the temperature between −15 and −5° C. After stirring for 10 minutes a solution of $KMnO_4$ (111 g, 0.7 mol) in water (900 ml) was added dropwise over 75 minutes while maintaining the temperature between −3 and 3° C. The mixture was stirred at 0° C. until GC analysis indicated the reaction was complete. tert-Butyl methyl ether (500 ml) was added followed by saturated aqueous $NaHSO_3$ (1000 ml) and the resulting mixture was stirred for 30 minutes until a milky white slurry formed. This slurry was filtered, washed with a solution of 3N NaOH (50 ml) and water (100 ml) followed by tert-butyl methyl ether (100 ml). The pH of the filtrate was adjusted from 8.6 to 12.5 by the addition of 3N NaOH (100 ml) and 6N NaOH (40 ml). The phases were separated and to the aqueous phase was added tert-butyl methyl ether (500 ml). The pH of the resulting mixture was adjusted to 2 with 6N HCl (200 ml). The phases were again separated and the aqueous phase was extracted with tert-butyl methyl ether (2×300 ml). The organic phases were combined, dried over $MgSO_4$, filtered and evaporated to give the title compound (73 g, 89%), as an off white solid.

DESCRIPTION 39

2-Bromo-6-fluorobenzaldehyde

To a solution of diisopropylamine (15.7 ml 112 mmol) in anhydrous tetrahydrofuran (200 ml) cooled to 0° C. was added dropwise n-butyllithium (2.5M in hexanes, 44.8 ml, 112 mmol). After complete addition the mixture was cooled to −78° C. and 3-fluorobromobenzene (19.6 g, 112 mmol) added over 10 minutes. The mixture stirred at −78° C. for 1 hour then N,N diimethylformamide (9.72 ml, 125 mmol) was added dropwise over 5 minutes. The mixture was stirred for a further 10 minutes, then acetic acid (10 ml) and water (350 ml) were added. The mixture was allowed to warm to room temperature and was extracted with $Et_2O$ (250+150 ml). The combined extracts were washed with water (×2) 0.2N HCl, brine, dried over $Na_2SO_4$ and evaporated. The residue was purified by column chromatography on silica eluting with 5% $Et_2O$ in iso-hexanes to give the title compound (20 g, 88%) as a white solid.

DESCRIPTION 40

2-Fluoro-6-[(trimethylsilyl)ethynyl]benzaldehyde

To a solution of 2-bromo-6-fluorobenzaldehyde (Description 39; 10.0 g, 49.3 mmol) and (trimethylsilyl) acetylene (13.94 ml, 98.6 mmol) in anhydrous N,N-dimethylformamide (250 ml) under an atmosphere of nitrogen was added triethylamine (10.25 ml, 73.95 mmol), copper (I) iodide (0.94 g, 4.93 mmol) and $Pd(PPh_3)_2Cl_2$ (1.73 g, 2.47 mmol). The mixture was degassed and stirred at room temperature overnight. The mixture was poured into water (600 ml) and extracted with ethyl acetate (3×200 ml). The combined organic layers were washed with water (3×300 ml), brine (200 ml) then dried over $Na_2SO_4$ and evaporated. The residue was purified by column chromatography on silica gel eluting with 5% $Et_2O$ in iso-hexanes to give the title compound (10.38 g, 95%).

DESCRIPTION 41

8-Fluoroisoquinoline

2-Fluoro-6-[(trimethylsilyl)ethynyl]benzaldehyde Description 40; 10.38 g, 47.1 mmol) was dissolved in 2M ammonia in methanol (235 ml, 471 mmol) in a Parr flask and the resulting mixture heated at 80° C. with shaking on a Parr apparatus (ca. 35 psi achieved). The reaction was cooled and the solvents evaporated. The residue was purified by column chromatography on silica eluting with a gradient from neat dichloromethane to 2% methanol in dichloromethane to give the title compound (4.0 g, 58%).

DESCRIPTION 42

8-Fluoro-5-nitroisoquinoline

To a solution of 8-fluoroisoquinoline (Description 41; 1.24 g, 8.4 mmol) in concentrated sulfuric acid (10 ml) cooled to between −5° C. and 0° C. was added slowly, over 10 minutes, a solution of potassium nitrate (0.93 g, 9.24 mmol) in concentrated sulfuric acid (5 ml). The mixture was stirred at 0° C. for 30 minutes after which time TLC indicated that reaction was complete. The mixture was poured onto ice (100 g) and basified by the careful addition of 33% aqueous ammonium hydroxide. The mixture was extracted with dichloromethane (3×150 ml) and the combined organic layers were washed with brine, dried over $Na_2SO_4$ and filtered through a 1 inch plug of silica gel. The silica gel plug was further washed with 150 ml of a 1:1 mix of ethyl acetate and iso-hexanes. The combined organics were evaporated to give the title compound (1.33 g, 82%) as a brown solid.

DESCRIPTION 43

8-Fluoroisoquinolin-5-amine

To a nitrogen flushed solution of 8-fluoro-5-nitroisoquinoline (Description 42; 1.33 g, 6.9 mmol) in methanol (100 ml) was added 10% palladium on carbon (500 mg) and the resulting mixture stirred under a balloon of hydrogen for 3.5 hours. The catalyst was removed by filtration and the filtrate evaporated to dryness. The residue was purifted by MPLC (Biotage Flash™ 40) eluting with 2% MeOH in dichloromethane to give the title compound (450 mg, 40%) as a yellow solid.

DESCRIPTION 44

3-Methyl-5-nitroisoquinoline

3-Methylisoquinoline (2.14 g, 14.9 mmol) was added portionwise to ice-cooled concentrated $H_2SO_4$ (10 ml) keeping the internal temperature below 10° C. A nitrating mixture of concentrated $H_2SO_4$ (2 ml) and fuming nitric acid (2 ml) was then added dropwise keeping the internal temperature below 15° C. After stirring for 30 minutes, TLC indicated reaction was complete. The acid was neutralized by adding the mixture to an excess of 4N aqueous NaOH (180 ml) with ice-cooling. The mixture was extracted with dicbloromethane (2×150 ml), then dried ($Na_2SO_4$) and evaporated to give the crude product (2.69 g) as a yellow solid. Flash column chromatography using as eluant 5% methanol in dicbloromethane gave a pure sample of the title compound (660 mg) and a further sample (1.95 g) containing ca. 10% of the isomer 3-methyl-8-nitroisoquinoline.

DESCRIPTION 45

3-Methylisoquinolin-5-amine

3-Methyl-5-nitroisoquinoline (Description 44; 660 mg, 3.51 mmol) was dissolved in MeOH (30 ml) and $PtO_2$ catalyst (120 mg) was added. The mixture was stirred for 1 hour 45 minutes under a balloon of hydrogen, then the catalyst was filtered off, washing with more methanol. The filtrate was evaporated and purified by flash column chromatography using as eluant 5% methanol in dichloromethane to give the title compound (250 mg).

DESCRIPTION 46

1-Chloroisoquinoline

A solution of isoquinoline-N-oxide (5.52 g, 38 mmol) in dichloromethane (50 ml) was added over 15 minutes to a solution of phosphorus oxychloride (40 ml) in dichloromethane (50 ml) at room temperature. The mixture was stirred for 1 hour, then heated to reflux for 2 hours. After cooling to room temperature, the mixture was poured into ice water (500 ml). The mixture was then extracted with dichloromethane (2×250 ml) and the combined organic layers were washed with 10% aqueous potassium carbonate solution (200 ml), brine (200 ml) then dried ($Na_2SO_4$) and evaporated to give the title compound (5.0 g).

DESCRIPTION 47

1-Chloro-5-nitroisoquinoline

1-Chloroisoquinoline (Description 46; 4 g, 24.4 mmol) was nitrated according to the method of Description 44 to give the title compound (3.88 g).

DESCRIPTION 48

1-Chloroisoquinolin-5-amine

Copper (II) acetylacetonate (253 mg) was suspended in ethanol (10 ml) and sodium borohydride (366 mg) was added in one portion. The mixture was stirred for 5 minutes, by which time a black suspension had appeared. A suspension of 1-chloro-5-nitroisoquinoline (Description 47; 1.01 g, 4.84 mmol) in ethanol (20 ml) was then added over 15 minutes whilst cooling in a water bath; the mixture effervesced. The mixture was stirred at room temperature for 1 hour, then more sodium borohydride (160 mg) was added and stirring continued for a further 1 hour. Water (100 ml) was added then the ethanol was evaporated and the mixture extracted with ethyl acetate (3×50 ml). The combined organic layers were dried ($Na_2SO_4$) and evaporated. Purification of the residue by flash column chromatography using 5% methanol-dichloromethane as eluant gave the title compound (210 mg).

DESCRIPTION 49

3-Chloroisoquinoline

A mixture of 1,3-dichloroisoquinoline (9.94 g, 50.2 mmol) and hydrazine hydrate (12.2 ml, 251 mmol) in ethanol (150 ml) was heated at reflux for 1.5 hours. The reaction was then cooled to room temperature and the ethanol evaporated. The residue was suspended in chloroform and manganese dioxide (20 g) was added in portions over 30 minutes. Gas evolution was observed. After this had subsided, the mixture was heated to reflux for 2 hours, then filtered and evaporated. Purification of the residue by flash column chromatography using dichloromethane as eluant gave the title compound (3.5 g).

DESCRIPTION 50

3-Chloroisoquinolin-5-amine

3-Chloroisoquinoline (Description 49; 3.4 g, 20.7 mmol) was nitrated according to the method of Description 44 to give crude 3-chloro-5-nitroisoquinoline (9 g). A sample (3.08 g) was added in portions over 15 minutes to a mixture of iron powder (4.2 g, 74 mmol) in water (50 ml) and 5M HCl (4 ml) at 50° C. After the addition, the mixture was warmed to 85° C. for 2 hours, then filtered while still warm to remove the iron. The filtrate was basified (4N NaOH, ca. 50 ml), then extracted with dichloromethane (3×150 ml). The combined organic layers were dried ($Na_2SO_4$) and evaporated to give the title compound (282 mg).

DESCRIPTION 51

6-Aminoisoquinoline

Benzophenone imine (445 μL, 2.64 mmol) was added to a mixture of 6-bromoisoquinoline (500 mg, 2.4 mmol), BINAP (60 mg, 0.1 mmol), palladium acetate (12 mg, 0.05 mmol) and cesium carbonate (1.0 g, 3.07 mmol) in THF (10 ml) at room temperature. The mixture was degassed ($N_2$×3) then heated at reflux under a nitrogen atmosphere for 16 hours. The reaction was then cooled to room temperature, partitioned between ethyl acetate (20 ml) and water (20 ml) and the aqueous phase extracted with ethyl acetate (20 ml). The combined organic phases were evaporated then re-dissolved in THF (15 ml). Hydrochloric acid (2N, aqueous, 4 ml) was added, then after stirring for 1 hour the THF was evaporated. The mixture was partitioned between ethyl acetate (20 ml) and 3M HCl (50 ml) and the aqueous phase washed with ethyl acetate (20 ml). The aqueous phase was basified (12N NaOH) then extracted with dichloromethane (3×50 ml). The combined organic phases were dried ($Na_2SO_4$) and evaporated to give the title compound (360 mg).

DESCRIPTION 52

N-(2-Bromobenzyl)-2.2-diethoxyacetamide

To a solution of ethyl diethoxyacetate (20.0 g, 114 mmol) in ethanol (50 ml) was added a solution of sodium hydroxide (4.56 g, 114 mmol) in water (25 ml), and the resulting mixture heated at reflux for 5 hours. The mixture was evaporated to dryness, and the residue dried in vacuo. The resulting solid (22.75 g, 0.13 mol) was dissolved in dry ether (88 ml) and to this mixture was added thionyl chloride (13.3 g, 0.11 mol) with stirring for 10 minutes at 10° C. The reaction mixture was heated at reflux for 30 minutes and then allowed to cool. A solution of 2-bromobenzylamine (20.73 g, 0.11 mol) in toluene (57 ml) and pyridine (34 ml) was poured into this reaction mixture with vigorous stirring. This was heated at reflux for 30 minutes and then allowed to cool. The mixture was poured into ice water and extracted with toluene (×3). The organic extracts were combined and washed firstly with 2% HCl and then water. The solvent was evaporated and the residue purified by flash chromatography on silica gel (9:1 hexane:ethyl acetate) to give the title compound (15.6 g, 44%).

DESCRIPTION 53

8-Bromoisoquinolin-3-ol

N-(2-Bromobenzyl)-2,2-diethoxyacetamide (Description 52; 15.6 g, 49 mmol) was carefully added to concentrated $H_2SO_4$ (78 ml) with stirring at 10-20° C. The reaction mixture was stirred at room temperature for 16 hours, poured into ice water and filtered. The filtrate was neutralised with 33% aqueous ammonium hydroxide and the resulting precipitate was filtered and dried to give the title compound (10.1 g, 91%).

DESCRIPTION 54

8-Bromo-3-methoxyisoquinoline

To a suspension of 8-bromoisoquinolin-3-ol (Description 53; 7.3 g, 0.03 mol) and silver carbonate (13.6 g, 0.05 mol) in dry DMF (380 ml) under nitrogen was added iodomethane (2.25 ml, 0.04 mol). The mixture was stirred at 50° C. for 24 hours. Further iodomethane (1 ml, 0.015 mol) was added and the mixture heated for 64 hours at 50° C. The mixture was cooled, water (300 ml) and ethyl acetate (300 ml) were added and shaken well. The mixture was filtered through Celite™, the layers separated and the aqueous layer was extracted with ethyl acetate (3×50 ml). The organic layers were combined, evaporated to ~150 ml, washed twice with water and then brine. The organic extract was then evaporated to give the title compound (1.7 g, 22%).

DESCRIPTION 55

Methyl 3-methoxyisoquinoline-8-carboxylate

To a solution of 8-bromo-3-methoxyisoquinoline (Description 54; 1.6 g, 7.0 mmol) in anhydrous DMSO (12 ml) and methanol (8 ml) was added triethylamine (1.0 ml, 7.0 mmol), palladium acetate (30 mg, 0.1 mmol) and 1,1'-bis(diphenylphosphine)ferrocene (75 mg, 0.1 mmol). Carbon monoxide was bubbled through the mixture for 3 minutes and the reaction was then heated with stirring at 80° C. for 44 hours under a balloon of carbon monoxide. Palladium acetate (30 mg, 0.1 mmol), 1,1'-bis(diphenylphosphine)ferrocene (75 mg, 0.1 mmol), DMSO (4 ml) and methanol (6 ml) were added to the mixture and carbon monoxide was bubbled through for 3 minutes. The reaction was again heated at 80° C. under a carbon monoxide balloon for 5 hours. The mixture was allowed to cool, brine (80 ml) was added and the mixture was extracted with ethyl acetate (3×20 ml). The combined organic layers were washed with brine (50 ml), dried over $K_2CO_3$ and evaporated. The residue was chromatographed on silica gel (19:1 dichloromethane:methanol) to give the title compound (290 mg, 20%).

DESCRIPTION 56

3-Methoxyisoquinoline-8-carboxylic acid

To a solution of methyl-3-methoxyisoquinoline-8-carboxylate (Description 55; 280 mg, 1 mmol) in ethanol (10 ml) was added potassium hydroxide (145 mg, 3 mmol) in water (6 ml). This mixture was heated at reflux for 30 minutes, cooled and the ethanol removed by evaporation. The remaining aqueous mixture was acidified with 1M HCl (3 ml) to pH 5. The solid was collected by filtration and dried in a vacuum oven to give the title compound (235 mg, 90%).

DESCRIPTION 57

Isoquinoline-8-carboxylic acid

THF (140 ml) was added to n-butyllithium (1.6M hexanes, 70 ml, 112 mmol) at −78° C. A cold (−78° C.) solution of 8-bromoisoquinoline (19 g, 91.3 mmol) was then added. The reaction was stirred for 15 minutes at −78° C., then dry $CO_2$ gas was bubbled through the solution for 30 minutes. The cooling was then removed and the mixture warmed to 0° C. over 1 hour. The THF was removed in vacuo, then aqueous NaOH (2N, 300 ml) was added. The mixture was washed with tert-butyl methyl ether (300 ml, then 2×100 ml) and the combined organic layers were back extracted with aqueous NaOH (2N, 50 ml). The combined aqueous phase was adjusted to pH 4.5 by the addition of 6N HCl. And the slurry cooled to 15° C. using an ice-bath. The precipitate was collected by filtration, washed with water (2×100 ml), isopropanol (100 ml), acetone (100 ml) and tert-butyl methyl ether (100 ml) to give the title compound (8.62 g).

DESCRIPTION 58

[4-(Trifluoromethyl)benzyl]isocyanate 4-(Trifluoromethyl)phenylacetic acid (1.79 g, 8.77 mmol) was dissolved in dichloromethane (20 ml) at room temperature. Oxalyl chloride (0.92 ml, 10.5 mmol) was added followed by DMF (2 drops). The reaction was stirred for 4 hours, after which time effervescence had ceased. The dichloromethane and excess oxalyl chloride were then evaporated. The acid chloride was redissolved in DCM (20 ml) and poured in one go into a solution of sodium azide (0.63 g, 9.65 mmol) and tetrabutylammonium bromide (300 mg, 0.88 mmol) in water (15 ml). The mixture was stirred for 15 minutes, then the layers separated and the aqueous layer extracted with more dichloromethane (30 ml). The combined organic layers were dried ($Na_2SO_4$) and evaporated to give an oil which was purified by flash column (50% dichloromethane-hexane). The acyl azide (1.54 g) so produced was dissolved in dichloromethane (20 ml) and heated at reflux to quantitatively afford the title compound. The volume was adjusted to give a 0.33 M solution in dichloromethane for use in subsequent preparations.

DESCRIPTION 59

[4-(Trifluoromethoxy)benzyl]isocyanate

Prepared from 4-(trifluoromethoxy)phenylacetic acid according to the method of Description 58.

Synthesis of Ureas

Ureas were synthesized, unless otherwise stated, using one of 2 methods. A convenient procedure starts with a carboxylic acid which, on treatment with diphenylphosphoryl azide and triethylamine, undergoes a Curtius reaction. The isocyanate formed in situ is then trapped by addition of an amine all in one-pot. Alternatively ureas are synthesized by reacting an amine with a preformed isocyanate. Urea precursors not mentioned in Descriptions 1 to 58 are known compounds.

DESCRIPTION 60

Representative One-Pot Procedure for the Synthesis of Ureas from a Carboxylic Acid and an Amine A mixture of carboxylic acid (0.30 mmol), diphenylphosphoryl azide (65 μl, 0.30 mmol) and triethylamine (42 μl, 0.30 mmol) in toluene (5 ml) was heated at reflux for 1 hour. To this mixture, the appropriate amine (0.30 mmol) was added and the reaction heated at reflux for 18 hours. The cooled reaction mixture was evaporated to dryness, then purified either by flash column chromatography, preparative thin layer chromatography or by mass-directed HPLC. For amine hydrochloride salts, an extra equivalent of triethylamine was added.

DESCRIPTION 61

Representative One-Pot Procedure for the Synthesis of Ureas from an Isocyanate and an Amine An amine (0.30 mmol) and an isocyanate (0.35 mmol) were dissolved in dichloromethane (10 ml), then stirred at room temperature or at reflux if required until the starting amine had been consumed. The product was collected by filtration, washing with a little dichloromethane. In cases where the product did not crystalise out, the solvent was evaporated and purification was effected either by flash column chromatography, preparative thin layer chromatography or by mass-directed HIPLC.

DESCRIPTION 62

3-(trifluoromethyl)isoquinoline

1-Chloro-3-(trifluoromethyl)isoquinoline [see WO 01/92233] (2.0 g, 8.64 mmol) was dechlorinated according to the method of Description 49 to give the title compound (142 g).

DESCRIPTION 63

5-nitro-3-(trifluoromethyl)isoquinoline 3-(trifluoromethyl)isoquinoline (Description 62; 1 g, 5.0 mmol) was nitrated according to the method of Description 44 to give the title compound (1.1 g).

DESCRIPTION 64

3-(trifluoromethyl)isoquinolin-5-amine 5-nitro-3-(trifluoromethyl)isoquinoline (Description 63; 1 g, 4.13 mmol) was hydrogenated according to the method of Description 43 to give the title compound (0.48 g).

DESCRIPTION 65

1-chloro-3-ethyl-5-nitroisoquinoline 1-chloro-3-ethylisoquinoline [see WO 01/92233] (2.0 g, 10.4 mmol) was nitrated according to the method of Description 42 to give the title compound (2.37 g, 96%).

DESCRIPTION 66

1-chloro-3-ethylisoquinolin-5-amine 1-chloro-3-ethyl-5-nitroisoquinoline (Description 65; 2.0 g, 8.4 mmol) was reduced according to the method of Description 50 to give the title compound (1.2 g, 69%).

DESCRIPTION 67

1-Methyl-5-nitroisoquinoline

Prepared by nitration of 1-methylisoquinoline according to the procedure of Description 44.

DESCRIPTION 68

1-Methylisoquinolin-5-amine

Prepared by reduction of 1-methyl-5-nitroisoquinoline (Description 67) according to the procedure of Description 45.

DESCRIPTION 69

2,4-Difluoro-6-methoxybenzaldehyde

To a solution of 3.5-difluoroanisole (25 g; 175 mmol) in dichloromethane (150 ml) cooled at 0° C. was added titanium tetrachloride (30.7 ml; 280 mmol). To this mixture was added dropwise over 10 minutes dichloromethyl methylether (15.8 ml; 175 mmol), and after complete addition the mixture was stirred at room temperature for 1 hour. The reaction was poured onto ice/water (500 ml) and extracted with DCM (3×300 ml). The combined DCM layers were washed with water (500 ml), saturated NaCl (200 ml), dried over $Na_2SO_4$, filtered and evaporated. The residue was purified by column chromatography on silica-eluting with a gradient rising from 15% $Et_2O$ in isohexanes rising to 30% $Et_2O$ in isohexanes to give the title compound (11.2 g, 37%) as a white solid.

DESCRIPTION 70

2,4-Difluoro-6-hydroxybenzaldehyde

To a solution of 2,4-difluoro-6-methoxybenzaldehyde (Description 69, 11.2 g; 77.8 mmol) in anhydrous dichloromethane (500 ml) cooled at −78° C. was added boron tribromide (9.47 ml; 85.58 mmol) dropwise over 10 minutes. After complete addition the mixture was allowed to warm to room temperature and stirred overnight. The mixture was poured onto ice/water (1 litre) and extracted with DCM (3×400 ml). The combined organic layers were washed with water (1 litre), saturated NaCl (500 ml), dried over $Na_2SO_4$, filtered and evaporated. The residue was purified by column chromatography on silica elution with 10% diethyl ether/isohexanes to give the title compound (9.2 g, 75%) as an orange oil.

DESCRIPTION 71

2,4-Difluoro-6-prop-1-ynylbenzaldehyde

To an ice-bath cooled mixture of 2,4-difluoro-6-hydroxybenzaldehyde (Description 70, 9.20 g; 58.2 mmol) and triethylamine (8.92 ml; 64.02 mmol) in anhydrous dichloromethane (100 ml) was added dropwise over 10 minutes trifluoromethanesulfonic anhydride (11.75 ml; 69.84 mmol) and the resulting mixture stirred at room temperature for 1 hour. The mixture was washed with water (300 ml), and the aqueous phase extracted with DCM (100 ml). The combined organic layers were washed with saturated NaCl (100 ml), dried over $Na_2SO_4$, filtered through a 1 inch plug of silica and evaporated. The residue (14.4 g; 49.6 mmol) and triethylamine (10.37 ml; 74.4 mmol) in anhydrous N,N-dimethylformamide (80 ml) contained within a large (200 ml capacity) sealed tube was cooled to −78° C. and propyne gas bubbled through until the volume had increased by approx 10 ml. To this mixture was added $Pd(PPh_3)_2Cl_2$ (1.74 g; 2.48 mmol) and CuI (449 mg; 4.96 mmol), the lid was put in place and the tube allowed to reach room temperature. The reaction was stirred for 2 hours after which TLC showed reaction was complete. The mixture was poured onto water (500 ml) and extracted with EtOAc (3×150 ml); the combined EtOAc layers were washed with water (3×400 ml), saturated NaCl (150 ml), dried over Na2SO4, filtered through a 1 inch plug of silica and evaporated to give the title compound (8.7 g, 97%).

DESCRIPTION 72

6,8-Difluoro-3-methylisoquinoline

A mixture of 2,4-difluoro-6-prop-1-ynylbenzaldehyde (Description 71, 8.7 g; 48.8 mmol) and 2.0M ammonia in methanol (244 ml; 488 mmol) were heated together at 80° C. in a Parr apparatus (approx 35 psi achieved) for 5 hours. The cooled mixture was evaporated and the residue purified by column chromatography on silica-elution with 100% dichloromethane to give the title compound (5.2 g, 59%) as a brown solid.

DESCRIPTION 73

6,8-Difluoro-3-methylisoquiolin-5-amine

To an ice-bath cooled solution of 6,8-difluoro-3-methylisoquinoline (Description 72, 1.2 g; 5.35 mmol) in conc. sulfuric acid (7.5 ml) was added dropwise a mixture of fuming nitric acid (1 ml) and conc. sulfuric acid (1 ml) and the resulting mixture stirred at 0° C. for 30 minutes. Poured onto ice/water (100 ml) and basified by the portionwise addition of $NaHCO_3$, then extracted with EtOAc (3×100 ml). The combined EtOAc layers were flushed with nitrogen and a spatula end of 5% palladium on carbon added and the reaction was stirred under a balloon of hydrogen for 3 hours. The catalyst was removed by filtration and the filtrate evaporated. The residue was purified by column chromatography on silica elution with 1% MeOH in DCM+0.5% $NH_4OH$ to give the title compound (930 mg, 89%).

DESCRIPTION 74

3-Methyl-7-(trifluoromethyl)isoquinolin-5-amine

Prepared using 2-hydroxy-5-trifluoromethylbenzaldehyde [see WO-A-9962902] in place of 2,4-difluoro-6-hydroxybenzaldehyde according to the procedures of Descriptions 71, 72, and 73 respectively.

DESCRIPTION 75

2-Fluoro-6-prop-1-ynylbenzaldehyde

A mixture of 2-bromo-6-fluorobenzaldehyde [see *Tetrahedron Letters* (1992), 33(49), 7499-7502] (4.0 g; 19.7 mmol) and triethylamine (4.12 ml; 29.5 mmol) in anhydrous N,N-dimethylformamide (75 ml) contained within a large (200 ml capacity) sealed tube was cooled to −78° C. and propyne gas bubbled through until the volume had increased by approx 10 ml. To this mixture was added $Pd(PPh_3)_2Cl_2$ (0.69 g; 0.99 mmol) and CuI (180 mg; 1.97 mmol), the lid was put in place and the tube allowed to reach room temperature and stir for 4 hours after which TLC showed the reaction was complete. The mixture was poured onto water (500 ml) and extracted with EtOAc (3×150 ml). The combined EtOAc layers were washed with water (3×400 ml), saturated NaCl (150 ml), dried over $Na_2SO_4$, filtered through a 1 inch plug of silica and evaporated to give the title compound (3.2 g, 100%).

DESCRIPTION 76

8-Fluoro-3-methylisoquinolin-5-amine

Prepared using 2-fluoro-6-prop-1-ynylbenzaldehyde (Description 75) in place of 2,4-difluoro-6-prop-1-ynylbenzaldehyde according to the procedures of Descriptions 72 and 73 respectively.

DESCRIPTION 77

(2-Bromo-4-fluorophenyl)methanol

To a solution of 2-bromo-4-fluorobenzoic acid (20 g; 91 mmol) in anhydrous THF (300 ml) at −10° C. was added dropwise borane tetrahydrofuran complex (1.0M soln in THF) (136.5 ml; 136.5 mmol). After complete addition the reaction was allowed to stir at room temperature for 4 hours. The reaction was quenched by the dropwise addition of water (20 ml). To the mixture was added saturated $K_2CO_3$ (200 ml) and water (300 ml). The organic layer was separated and the aqueous extracted with $Et_2O$ (2×300 ml). The combined organics were washed with water (2×500 ml), saturated NaCl (200 ml), dried over $Na_2SO_4$, filtered and evaporated to give the title compound (18 g, 96%) as a white solid.

DESCRIPTION 78

2-Bromo-4-fluorobenzaldehyde

To a −78° C. cooled solution of oxalyl chloride (8.43 ml; 96.58 mmol) in anhydrous dichloromethane (300 ml) was added dropwise dimethyl sulfoxide (13.71 ml; 193.16 mmol). The mixture was stirred at −78° C. for 5 minutes then a solution of (2-bromo-4-fluorophenyl)methanol (Description 77, 18 g; 87.8 mmol) in anhydrous dichloromethane (150 ml) was added slowly. The resulting mixture was stirred at −78° C. for 15 minutes then triethylamine (36.71 ml; 263.4 mmol) was added and the mixture allowed to warm to room temperature over 1 hour. The mixture was washed with water (2×500 ml), saturated NaCl (200 ml), dried over $Na_2SO_4$, filtered through a 2 inch plug of silica gel and evaporated to give the title compound (16 g, 89%) as a white solid.

DESCRIPTION 79

6-Fluoro-3-methylisoquinolin-5-amine

Prepared using 2-bromo-4-fluorobenzaldehyde (Description 78) in place of 2-bromo-6-fluorobenzaldehyde according to the procedures of Descriptions 75, 72, and 73 respectively.

DESCRIPTION 80

2-Hydroxy-5-methoxy-3-nitrobenzaldehyde

To a solution of 5-methoxysalicylaldehyde (22.52 g; 148 mmol) in acetic acid (120 ml) was added dropwise over 1 hour a mixture of fuming nitric acid (7.1 ml) in acetic acid (25 ml). After complete addition the mixture was stirred at room temperature for 5 hours. The precipitate was removed by filtration, washed with ethanol and dried to give the title compound (20.3 g, 69%) as a bright yellow solid.

DESCRIPTION 81

2-Formyl-4-methoxy-6-nitrophenyl trifluoromethanesulfonate

To an ice-bath cooled solution of 2-hydroxy-5-methoxy-3-nitrobenzaldehyde (Description 80, 11.00 g; 55.8 mmol) and triethylamine (10.11 ml; 72.54 mmol) in anhydrous dichloromethane (150 ml) was added slowly trifluoromethane sulfonic anhydride (11.73 ml; 69.75 mmol) and the resulting mixture stirred at room temperature for 1.5 hours. The mixture was washed with water (250 ml), dried over $Na_2SO_4$, filtered through a 1.5 inch plug of silica and evaporated to give the title compound (17 g, 92%) as a yellow oil.

DESCRIPTION 82

7-Methoxyisoquinolin-5-amine

Prepared using 2-formyl-4-methoxy-6-nitrophenyl trifluoromethanesulfonate (Description 81) in place of 2-bromo-6-fluorobenzaldehyde according to the procedures of Descriptions 40, 41, and 43 respectively.

DESCRIPTION 83

1,3-Dimethylisoquinolin-5-amine

Prepared using 1,3-dimethylisoquinoline (*Chem Lett.* 1983, 5, 791) in place of 3-methylisoquinoline according to the procedures of Descriptions 44 and 43 respectively.

DESCRIPTION 84

4-Chloro-2-formyl-6-nitrophenyl trifluoromethanesulfonate

Prepared using 5-chlorosalicylaldehyde in place of 5-methoxysalicylaldehyde according to the procedures of Descriptions 80 and 81 respectively.

DESCRIPTION 85

7-Chloro-3-methyl-5-nitroisoquinoline

Prepared using 4-chloro-2-formyl-6-nitrophenyl trifluoromethanesulfonate (Description 84) in place of 2-bromo-6-fluorobenzaldehyde according to the procedures of Descriptions 75 and 72 respectively.

DESCRIPTION 86

7-Chloro-3-methylisoquinolin-5-amine

To a nitrogen flushed solution of 7-chloro-3-methyl-5-nitroisoquinoline (Description 85; 300 mg, 1.35 mmol) in methanol (30 ml) was added a spatula end of Palladium 5% on calcium carbonate poisoned with lead (lindlar catalyst), and the resulting mixture stirred under a balloon of hydrogen overnight. The catalyst was removed by filtration and the filtrate evaporated. The residue was dissolved in methanol (20 ml) and silica gel (2 g) added and evaporated to dryness. Loaded onto a silica gel column and eluted with 1% MeOH in DCM+0.5% $NH_4OH$ to give the title compound (190 mg, 73%) as an orange solid.

DESCRIPTION 87

7-Chloroisoquinolin-5-amine

Prepared using 4-chloro-2-formyl-6-nitrophenyl trifluoromethanesulfonate (Description 84) in place of 2-bromo-6-fluorobenzaldehyde according to the procedures of Descriptions 40, 41 and 86 respectively.

DESCRIPTION 88

8-Fluoro-3-methoxyisoquinoline-5-carboxlic acid

Prepared using 5-bromo-2-fluorobenzylamine in place of 2-bromobenzylamine according to the procedures of Descriptions 52, 53, 54, 55, and 56 respectively.

DESCRIPTION 89

6-Fluoroisoquinolin-5-amine

Prepared using 2-bromo-4-fluorobenzaldehyde (Description 78) in place of 2-bromo-6-fluorobenzaldehyde according to the procedures of Descriptions 40, 41, 44 and 43 respectively.

DESCRIPTION 90

7-Fluoroisoquinolin-5-amine

Prepared using 2-bromo-5-fluorobenzoic acid in place of 2-bromo-4-fluorobenzoic acid according to the procedures of Descriptions 77, 78, 40, 41, 44 and 43 respectively.

DESCRIPTION 91

4-Methylisoquinolin-5-amine

Prepared using 4-methylisoquinoline (*Tet. Lett.* 1987, 28(44), 5291) in place of 3-methylisoquinoline according to the procedures of Descriptions 44 and 43 respectively.

DESCRIPTION 92

8-(Trifluoromethyl)isoquinoline

A mixture of 2-trifluoromethylbenzaldehyde (15 g; 86 mmol) and aminoacetaldehyde dimethylacetal (9.37 ml; 86 mmol) in toluene (75 ml) was heated at reflux under Dean/Stark conditions for 2 hours. The cooled reaction mixture was evaporated to dryness and the residue added dropwise to conc. sulfuric acid (200 ml) at 140° C.; after complete addition the heating was continued for 30 mins then the warm mixture was poured over ice. The mixture was filtered and the filtrate basified by the addition of 4N NaOH with cooling. The basic solution was extracted with $Et_2O$ (×3), the combined $Et_2O$ layers were dried over $Na_2SO_4$, filtered and evaporated. The residue was dissolved in DCM and filtered through a short plug of silica and evaporated to give 1.2 g (Yield 7%).

DESCRIPTION 93

8-(Trifuoromethyl)isoquinolin-5-amine

Prepared using 8-(trifluoromethyl)isoquinoline (Description 92) in place of 3-methylisoquinoline according to the procedures of Descriptions 44 and 43 respectively.

DESCRIPTION 94

2-Methoxy-4-(trifluoromethyl)benzonitrile

To a solution of 2-nitro-4-(trifluoromethyl)benzonitrile (22.48 g, 104 mmol) in anhydrous methanol (110 ml) was added dropwise 25% sodium methoxide in methanol (24.72 ml, 114.4 mmol), and the resulting mixture stirred at room temperature for 1 hour. Water (110 ml) was added and the resulting solids collected by filtration. The solids were dissolved in DCM (150 ml), washed with sat NaCl (75 ml), dried over $Na_2SO_4$, filtered and evaporated to give the title compound (19 g, 91%) as a white solid.

DESCRIPTION 95

2-Methoxy-4-(trifluoromethyl)benzoic acid

To a solution of 2-methoxy-4-(trifluoromethyl)benzonitrile (Description 94; 19 g, 94.4 mmol) in ethanol (150 ml) was added a solution of potassium hydroxide (26.43 g; 472 mmol) in water (100 ml) and the resulting mixture heated at reflux overnight. The mixture was cooled and the ethanol removed by evaporation, the remaining aqueous phase was extracted with diethyl ether then acidified with 5N HCl. The acidic aqueous phase was then extracted with EtOAc (3×200 ml) and the combined organic layers washed with water, sat NaCl, dried over $Na_2SO_4$, filtered and evaporated to give the title compound (19.91 g, 95%).

DESCRIPTION 96

2-Methoxy-4-(trifluoromethyl)benzaldehyde

Prepared using 2-methoxy-4-(trifluoromethyl)benzoic acid (Description 95) in place of 2-bromo-4-fluorobenzoic acid according to the procedures of Descriptions 77 and 78 respectively.

DESCRIPTION 97

2-hydroxy-4-(trifluoromethyl)benzaldehyde

A mixture of 2-methoxy-4-trifluoromethyl benzaldehyde (Description 96; 18 g, 88 mmol) and lithium chloride (11.19 g; 264 mmol) in anhydrous N,N-dimethylformamide (100 ml) was heated at reflux for 3 hours. The mixture was cooled and poured into water (200 ml), then acidified by the addition of 1N HCl. The mixture was extracted with ether (3×200 ml) then the combined ether layers washed with water (2×500 ml), sat NaCl (100 ml), dried over $Na_2SO_4$, filtered and evaporated to give the title compound (16.25 g, 97%).

DESCRIPTION 98

6-(Trifluoromethyl)isoquinolin-5-amine

Prepared using 2-hydroxy-4-(trifluoromethyl)benzaldehyde (Description 97) in place of 2-hydroxy-5-methoxy-3-nitrobenzaldehyde according to the procedures of Descriptions 81, 40, 41, 44, and 43 respectively.

DESCRIPTION 99

7-(Trifuoromethyl)isoquinolin-5-amine

Prepared using 2-hydroxy-5-(trifluoromethyl)benzaldehyde [see WO-A-9962902] in place of 2-hydroxy-5-methoxy-3-nitrobenzaldehyde according to the procedures of Descriptions 81, 40, 41, 44, and 43 respectively.

DESCRIPTION 100

5-Fluoro-1-methylindene

A solution of 5-fluoro-1-indanone (25 g, 0.17 mol) in dry THF (100 ml) was added dropwise to a solution of methyl magnesium bromide (70 ml of 3N in diethyl ether, 0.21 mol) in dry THF (50 ml) at 0° C. The mixture was stirred at RT overnight. The reaction mixture was quenched with aq. HCl to pH 1 and extracted with ethyl acetate (3×100 ml). The combined organic layers were washed with brine, dried over $MgSO_4$ and evaporated to give the title compound as an oil (22.3 g, 91%).

DESCRIPTION 101

6-Fluoro-1-methylisoquinoline

A solution of 5-fluoro-1-methylindene (Description 100, 22.3 g, 0.15 mol) in methanol (350 ml) was cooled to −78° C. and ozonised for 9.5 h. The reaction mixture was purged with nitrogen and removed from the cooling bath. Sodium bicarbonate (20 g) and dimethyl sulfide (30 ml) were added and the reaction mixture stirred at RT for 6 hr. Ammonium hydroxide (200 ml) was then added and the reaction mixture stirred at RT for 48 hr. The resulting mixture was poured into water (1 litre) and extracted with dichloromethane (3×400 ml). The organic extracts were combined, washed with water and brine, dried over $MgSO_4$ and evaporated. The residue was purified by flash column chromatography using an eluant system of 1% MeOH/99% DCM to give the title compound (1.4 g, 5.8%).

DESCRIPTION 102

6-Fluoro-1-methyl-5-nitroisoquinoline

Prepared by nitration of 6-fluoro-1-methylisoquinoline (Description 101) according to the procedure of Description 44 to give the title compound (530 mg, 30%).

DESCRIPTION 103

6-Fluoro-1-methylisoquinolin-5-amine

Prepared by reduction of 6-fluoro-1-methyl-5-nitroisoquinoline (Description 102) according to the procedure of Description 43 to give the title compound (435 mg, 96%).

DESCRIPTION 104

5-Nitroisoquinoline-1-carboxylic acid

Isoquinoline-1-carboxylic acid (3.98 g, 23.0 mmol) was dissolved in conc. sulfuric acid (16 ml) at 0° C. A mixture of conc. sulfuric acid (5 ml) and fuming nitric acid (5 ml) was added over 10 min. and the reaction stirred for a further 1 h at 0° C., then poured into ice-water (400 ml). The solid was collected by filtration, then washed with water (100 ml), ethanol (100 ml) and ether (100 ml), then dried under vacuum to give the title compound (4.1 g, 82%).

DESCRIPTION 105

Methyl 5-nitroisoquinoline-1-carboxylate

Potassium carbonate (23 g, 167 mmol) was added to a solution of 5-nitro-isoquinoline-1-carboxylic acid (Description 104, 2.7 g, 12.4 mmol) in N,N-dimethylformamide (50 ml) at room temperature. Iodomethane (1.0 ml, 16.1 mmol) was then added and the reaction stirred at room temperature for 20 h. Water (300 ml) was added and the mixture was extracted with ethyl acetate (2×200 ml). The combined organic phases were washed with water (2×100 ml), brine (100 ml) then dried ($Na_2SO_4$) and evaporated. Purification of the residue by column chromatography eluting with ethyl acetate-isohexane (7:13 increasing to 1:1) gave the title compound (558 mg, 19%).

DESCRIPTION 106

Methyl 5-aminoisoquinoline-1-carboxylate

Prepared by reduction of methyl 5-nitroisoquinoline-1-carboxylate (Description 105) according to the procedure of Description 45.

DESCRIPTION 107

Methyl-5-aminoisoquinoline-3-carboxylate

Prepared using isoquinoline-3-carboxylic acid in place of isoquinoline-1-carboxylic acid according to the procedures of Descriptions 104, 105 and 106 respectively.

DESCRIPTION 108

3-Chloro-5-nitroisoquinoline

3-Chloroisoquinolne (Description 49; 3.4 g, 20.7 mmol) was nitrated according to the method of Description 44. After addition of the base, the solid was filtered off to give crude 3-chloro-5-nitroisoquinoline (9 g). A sample (6.8 g) was partitioned between ethyl acetate and 10% aqueous $K_2CO_3$ solution (200 ml). The organic layer was extracted with more ethyl acetate (100 ml) and the combined organic phases dried ($Na_2SO_4$) and evaporated to give the title compound (2.10 g, 64%).

DESCRIPTION 109

3-(Dimethylamino)isoquinolin-5-amine

3-Chloro-5-nitroisoquinoline (Description 108, 160 mg, 0.767 mmol) was dissolved in 33% ethanolic dimethylamine (6 ml) and the mixture then heated in a sealed tube at 100° C. for 2.5 h. After cooling to room temperature the solvent and excess dimethylamine was evaporated and the residue reduced according to the procedure of Description 45 to give the title compound (85 mg, 59%).

DESCRIPTION 110

2-(4-Hydroxybut-1-ynyl)benzaldehyde

To a solution of 2-bromobenzaldehyde (10 g, 54 mmol) in anhydrous N,N-dimethylformamide (150 ml) was added 3-butyn-1-ol (6.13 ml, 81 mmol) and triethylamine (11.3 ml, 81 mmol), followed by copper (I) iodide (490 mg, 5.4 mmol) and $Pd(PPh_3)_2Cl_2$ (1.9 g, 2.7 mmol), and the mixture degassed three times and stirred at room temperature overnight. The mixture was poured into water (600 ml) and extracted with EtOAc (3×150 ml); the combined EtOAc layers were washed with water (2×250 ml), sat NaCl (100 ml), then dried over $Na_2SO_4$, filtered and evaporated. The residue was purified by column chromatography on silica eluting with 50% $Et_2O$ in isohexanes to give the title compound (8.5 g, 90%) as an orange oil.

DESCRIPTION 111

3-(2-Hydroxyethyl)isoquinoline

A solution of 2-(4-hydroxybut-1-ynyl)benzaldehyde (Description 110; 8.50 g, 48.8 mmol) in 2M methanolic ammonia (122 ml, 244 mmol) contained in a Parr flask was heated at 80° C. for 2 hours (approx 35 psi achieved). The cooled mixture was evaporated and the residue purified by column chromatography on silica elution with a gradient rising from 1% MeOH in DCM+0.5% $NH_4OH$ to 5% MeOH in DCM+ 0.5% $NH_4OH$ to give the title compound (6.2 g, 73%) as a beige solid.

DESCRIPTION 112

3-(2-Azidoethyl)isoquinoline

To a ice-bath cooled solution of 3-(2-hydroxyethyl)isoquinoline (Description 111; 4.85 g, 28 mmol) and triethylamine (5.07 ml, 36.4 mmol) in anhydrous dichloromethane (100 ml) was added slowly methanesulfonyl chloride (2.49 ml, 32.2 mmol), and the resulting mixture stirred at room temperature for 1 hour. The mixture was washed with water (200 ml), sat NaCl (100 ml), dried over $Na_2SO_4$, filtered and evaporated. The residue was dissolved in anhydrous N,N-dimethylformamide (100 ml) and sodium azide (2.00 g, 30.8 mmol) added and the resulting mixture stirred at room temperature for 4 days. The mixture was poured into water (400 ml), and extracted with EtOAc (3×100 ml). The combined EtOAc layers were washed with water (3×200 ml), saturated aqueous NaCl (100 ml), dried over $Na_2SO_4$, filtered and evaporated to give the title compound (5.6 g, 100%).

DESCRIPTION 113

3-(2-Aminoethyl)isoquinoline

To a solution of 3-(2-azidoethyl)isoquinoline (Description 112; 5.6 g, 28.3 mmol) in anhydrous tetrahydrofuran (50 ml) was added triphenylphosphine (14.85 g, 56.6 mmol) and water (0.509 ml, 28.3 mmol), and the resulting mixture stirred at room temperature overnight. The mixture was loaded directly onto a Bond-elut SCX cartridge and eluted with methanol until TLC indicated complete elution of triphenylphosphine. The product was then eluted with 2.0M ammonia in methanol. The basic fractions were collected and evaporated to give the title compound (2.7 g, 55%).

DESCRIPTION 114

Ethyl 2-isoquinolin-3-ylethylcarbamate

To an ice-bath cooled solution of 3-(2-aminoethyl)isoquinoline (Description 113; 2.70 g, 15.7 mmol) and triethylarnine (2.84 ml, 20.41 mmol) in anhydrous dichloromethane (75 ml) was added slowly ethyl chloroformate (1.65 ml, 17.27 mmol) and the resulting mixture stirred at room temperature for 1 hour. The mixture was washed with water, sat NaCl, dried over $Na_2SO_4$, filtered and evaporated. The residue was purified by column chromatography on silica elution with a gradient rising from DCM to 2% MeOH in DCM+0.5% $NH_4OH$ to give the title compound (2.27 g, 59%).

DESCRIPTION 115

Ethyl 2-(5-aminoisoquinolin-3-yl)ethylcarbamate

Prepared using ethyl 2-isoquinolin-3-ylethylcarbamate (Description 114) in place of 3-methylisoquinoline according to the procedures of Descriptions 44 and 43 respectively.

DESCRIPTION 116 tert-Butyl 2-(5-aminoisoquinolin-3-yl)ethylcarbamate

To a solution of potassium hydroxide (450 mg; 8.02 mmol) in ethanol was added ethyl 2-(5-aminoisoquinolin-3-yl)ethylcarbamate (Description 115; 1.04 g, 2.6 mmol), and the resulting mixture heated at reflux until HPLC indicated the reaction was complete (approx 5 days). The mixture was cooled and loaded directly onto a Bond-elut SCX cartridge. The cartridge was washed with methanol, and the product then eluted with 2M ammonia in methanol. The basic fractions were evaporated and the residue dissolved in dichloromethane (15 ml). Di-tert butyl dicarbonate (830 mg, 3.8 mmol) was added and the resulting mixture stirred at room temperature for 1 hour, then evaporated to dryness to give the title compound (1.1 g, 100%).

DESCRIPTION 117

Isoquinolin-7-yl trifluoromethanesulfonate

7-Hydroxyisoquinoline (1.4 g, 9.6 mmol) and triethylamine (1.5 ml, 10.6 mmol) were added to ether (50 ml) under a nitrogen atmosphere at 0° C. Trifluoromethylsulfonic anhydride (1.8 ml, 10.6 mmol) was added dropwise and the mixture then warmed to room temperature for 3 h. The layers were separated and the lower layer extracted with ether (2×100 ml). The combined organics were then dried ($Na_2SO_4$) and evaporated to give the title compound as a brown oil (1.04 g).

DESCRIPTION 118

2-(Trifluoromethyl)pyrimidine-5-carboxylic acid

To a solution of methyl 2-trifluoromethyl pyrimidine-5-carboxylate [see WO-A-0066567] (5 g, 22.7 mmol) in methanol (100 ml) was added a solution of lithium hydroxide (1.09 g, 45.4 mmol) and the resulting mixture stirred at room temperature overnight. The methanol was removed by evaporation and the residue further diluted with water (50 ml). Extracted with EtOAc (×3) and the aqueous phase was then acidified by the addition of c.HCl. The precipitate was extracted into EtOAc (×3) and the combined organic layers washed with sat NaCl, dried over $Na_2SO_4$, filtered and evaporated to give the title compound (2.0 g, 46%).

DESCRIPTION 119

5-(Hydroxymethyl)-2-(trifluoromethyl)pyrimidine

To an ice-bath cooled solution of 2-(trifluoromethyl)pyrimidine-5-carboxylic acid (Description 118; 2 g, 10.4 mmol) in anhydrous tetrahydrofuran (100 ml) was added dropwise borane tetrahydrofuran complex [1.0M solution in THF] (15.6 ml, 15.6 mmol), after complete addition the mixture was stirred at room temperature for 90 mins. The reaction was quenched by the careful addition of water (2 ml), followed by saturated aqueous $K_2CO_3$. The organic layer was separated, and the aqueous phase extracted with $Et_2O$. The combined organics were then washed with water, saturated NaCl, dried over $Na_2SO_4$, filtered and evaporated to give the title compound (580 mg, 31%).

DESCRIPTION 120

5-Azidomethyl-2-(trifluoromethyl)pyrimidine

To a solution of 5-(hydroxymethyl)-2-(trifluoromethyl) pyrimidine (Description 119; 580 mg, 3.26 mmol) and triethylamine (0.55 ml, 3.91 mmol) in anhydrous dichioromethane (15 ml) cooled in an ice-bath was added dropwise methanesulfonyl chloride (0.28 ml, 3.59 mmol), and the resulting mixture stirred at room temperature for 1 hour. The mixture was washed with water and sat NaCl, dried over Na$_2$SO$_4$, filtered and evaporated. The residue was dissolved in anhydrous N,N-dimethylformamide (15 ml), sodium azide (233 mg, 3.59 mmol) was added and the resulting mixture stirred at room temperature overnight. The mixture was poured into water (100 ml) and extracted with EtOAc (3×15 ml). The combined EtOAc layers were washed with water (2×50 ml), saturated NaCl (25 ml), dried over Na$_2$SO$_4$, filtered and evaporated to give the title compound (660 mg, 100%).

DESCRIPTION 121

5-(Aminomethyl)-2-(trifluoromethyl)pyrimidine

To a solution of 5-(azidomethyl)-2-(trifluoromethyl)pyrimidine (Description 120; 660 mg, 3.26 mmol) in anhydrous THF (10 ml) was added triphenylphosphine (1.71 g, 6.52 mmol) and water (0.059 ml, 3.26 mmol) and the resulting mixture stirred at room temperature overnight. The mixture was evaporated and the residue purified by column chromatography on silica elution with 5% MeOH in DCM+0.5% NH$_4$OH to give the title compound (320 mg, 55%) as a pale yellow solid.

DESCRIPTION 122

4-(Morpholin-4-ylmethyl)benzonitrile

To a solution of 4-cyanobenzylbromide (1.0 g, 5.1 mmol) in MeCN (10 ml) was added morpholine (0.44 g, 0.44 ml, 5.1 mmol) and the reaction was stirred at room temperature for 1 h. The precipitate was filtered off and partioned between CH$_2$Cl$_2$ and NaOH (2M). The organic layer was separated, dried over MgSO$_4$ and dried to give the desired nitrile (0.70 g, 68%).

DESCRIPTION 123

4-(Morpholin-4-ylmethyl)benzylamine

To a suspension of 4-(morpholin-4-ylmethyl)benzonitrile (Description 122, 0.5 g, 2.5 mmol) in THF (7 mL) at 0° C. was added dropwise a solution of LiAlH$_4$ (1.0 M in THF, 2.5 ml, 2.5 mmol). The reaction was stirred at 0° C. for 1 h. Additional LiAlH$_4$ (1.0 M in THF, 1.0 ml, 1.0 mmol) was added and the reaction stirred for an additional 30 min. The reaction was quenched by the addition of water (0.13 mL) followed by 15% NaOH solution (0.13 ml) and stirred vigorously for 1 h. The reaction was filtered through celite, evaporated and azeotroped twice with toluene. The amine was used crude.

DESCRIPTION 124

2-(2-Morpholin-4-ylethoxy)-4-(trifluoromethyl)benzonitrile

To a solution of 2-nitro-4-trifluoromethyl benzonitrile (0.5 g, 2.3 mmol) and 2-morpholin-4-yl-ethanol (0.37 g, 0.34 ml, 2.8 mmol) in DMF (4 ml) was added dropwise a solution of KOH (0.23 g, 4.1 mmol) in water (1.5 ml). After 10 min the reaction was poured into ice water and the white crystalline product collected by filtration, washed with water and dried (0.5 g, 72%).

DESCRIPTION 125

2-(2-Morpholin-4-ylethoxy)-4-(trifluoromethyl)benzylamine

To a solution of 2-(2-morpholin-4-ylethoxy)-4-(trifluoromethyl)benzonitrile (Description 124, 0.5 g, 1.67 mmol) in ethanol (30 ml) was added aqueous ammonia (33% aq soln, 5 ml) and a slurry of 10% Pd/C catalyst in water. The reaction was hydrogenated at 43 psi. After 45 min the reaction was complete. The catalyst was filtered off, the reaction condensed and the product azeotroped with toluene to give the desired amine (0.49 g, 96%).

DESCRIPTION 126

Isoquinoline-5-carbonyl azide

Isoquinoline-5-carboxylic acid monohydrate (5.00 g, 26.2 mmol) was suspended in dichloromethane (200 ml) and N,N-dimethylformamide (5 drops) added. Oxalyl chloride (4.57 ml, 52 mmol) was then added and the reaction stirred for 7 h. The solvent and excess oxalyl chloride was then evaporated and the residue taken up in dichloromethane (200 ml). A solution of sodium azide (2.1 g, 32.3 mmol) and tetra-n-butylammonium bromide (850 mg) in water (50 ml) was then added in one portion and the mixture stirred for 20 min. The layers were separated and the aqueous phase extracted with more dichloromethane (100 ml). The combined organic phases were evaporated and the residue purified by flash column chromatography (eluant ethyl acetate-dichloromethane (1:4)) to give the title compound as a yellow solid (2.27 g, 44%).

EXAMPLE 1

N-Benzyl-N'-isoquinolin-5-ylurea

Prepared from 5-aminoisoquinoline and benzyl isocyanate according to the procedure of Description 61. m/z (ES$^+$) 278 (M+H)$^+$.

Examples 2 to 16 were prepared according to the procedure of Description 60.

EXAMPLE 2

N-(1,1'-Biphenyl-4-ylmethyl)-N'-isoquinolin-5-ylurea

Prepared from isoquinoline-5-carboxylic acid [see WO 95/09843] and 4-phenylbenzylamine. m/z (ES$^+$) 354 (M+H)$^+$.

EXAMPLE 3

N-(1,1'-Bi-phenyl-3-ylmethyl)-N'-isoquinolin-5-ylurea

Prepared from isoquinoline-5-carboxylic acid and 3-phenylbenzylamine. m/z (ES$^+$) 354 (M+H)$^+$.

EXAMPLE 4

N-Isoquinolin-5-yl-N'-(3-phenylpropyl)urea

Prepared from isoquinoline-5-carboxylic acid and 3-phenylpropylamine. m/z (ES$^+$) 306 (M+H)$^+$.

EXAMPLE 5

N-Isoquinolin-5-yl-N'-(1,2,3,4-tetrahydronaphthalen-2-ylmethyl)urea

Prepared from isoquinoline-5-carboxylic acid and 1,2,3,4-tetrahydronaphthalen-2-ylmethylamine (Description 20). m/z (ES$^+$) 332 (M+H)$^+$.

EXAMPLE 6

N-[2-(4-Chlorophenyl)ethyl]-N'-isoquinolin-5-ylurea

Prepared from isoquinoline-5-carboxylic acid and 2-(4-chlorophenyl)ethylamine. m/z (ES$^+$) 326 (M+H)$^+$.

EXAMPLE 7

N-[3,5-bis(Trifluoromethyl)benzyl]-N'-isoquinolin-5-ylurea

Prepared from isoquinoline-5-carboxylic acid and 3,5-bis(trifluoromethyl)benzylamine. m/z (ES$^+$) 414 (M+H)$^+$.

EXAMPLE 8

N-[3-(3,4-dimethylphenyl)propyl]-N'-isoquiolin-5-ylurea

Prepared from isoquinoline-5-carboxylic acid and 3-(3,4-dimethylphenyl)-propylamine. m/z (ES$^+$) 334 (M+H)$^+$.

EXAMPLE 9

N-(4-tert-Butylbenzyl)-N'-isoquinolin-8-ylurea

Prepared from isoquinoline-8-carboxylic acid and 4-tert-butylbenzylamine. m/z (ES$^+$) 334 (M+H)$^+$.

EXAMPLE 10

N-(4-tert-Butylbenzyl)-N'-isoquinolin-5-ylurea

Prepared from isoquinoline-5-carboxylic acid and 4-tert-butylbenzylamine. m/z (ES$^+$) 334 (M+H)$^+$.

EXAMPLE 11

N-(4-tert-Butylbenzyl)-N'-quinolin-5-ylurea

Prepared from quinoline-5-carboxylic acid [see WO 95/09843] and 4-tert-butylbenzylamine. m/z (ES$^+$) 334 (M+H)$^+$.

EXAMPLE 12

N-(3-tert-Butylbenzyl)-N'-isoquinolin-5-ylurea

Prepared from isoquinoline-5-carboxylic acid and 3-tert-butylbenzylamine (Description 9). m/z (ES$^+$) 334 (M+H)$^+$.

EXAMPLE 13

N-[2-(4-tert-Butylphenyl)ethyl]-N'-isoquinolin-5-ylurea

Prepared from isoquinoline-5-carboxylic acid and 2-(4-tert-butylphenyl)ethylamine. m/z (ES$^+$) 348 (M+H)$^+$.

EXAMPLE 14

N-Isoquinolin-5-yl-N'-[4-(trifluoromethyl)benzyl]urea

Prepared from isoquinoline-5-carboxylic acid and 4-trifluoromethylbenzylamine. m/z (ES$^+$) 346 (M+H)$^+$.

EXAMPLE 15

N-Isoquinolin-5-yl-N'-[3-(trifluoromethyl)benzyl]urea

Prepared from isoquinoline-5-carboxylic acid and 3-trifluoromethylbenzylamine. m/z (ES$^+$) 346 (M+H)$^+$.

EXAMPLE 16

N-Isoquinolin-5-yl-N'-{2-[4-(trifluoromethyl)phenyl]ethyl}urea.

Prepared from isoquinoline-5-carboxylic acid and 2-[4-(trifluoromethyl)phenyl]ethylamine (Description 6). m/z (ES$^+$) 360 (M+H)$^+$.

EXAMPLE 17

N-(2-Oxidoisoquinolin-5-yl)-N'-[4-(trifluoromethyl)benzyl]urea

To a suspension of N-isoquinolin-5-yl-N'-[4-(trifluoromethyl)benzyl]urea (Example 14; 100 mg, 0.29 mmol) in chloroform (25 ml) was added Oxone (541 mg, 0.87 mmol), followed by wet alumina Grade III (1 g), and the resulting suspension heated at reflux for 60 minutes. Whilst the mixture was still hot it was filtered to remove alumina and Oxone, the solids were washed with more chloroform, then methanol, and the filtrate evaporated to dryness. The residue was purified by preparative TLC eluting with 10% MeOH in dichloromethane+0.5% NH$_4$OH, and the product triturated with a mixture of dichloromethane/iso-hexanes, filtered and dried to give the title compound (11 mg, 10%) as a white solid. m/z (ES$^+$) 362 (M+H)$^+$.

Examples 18 to 51 were prepared according to the procedure of Description 60.

EXAMPLE 18

N-Isoquinolin-5-yl-N'-{2-[3-(trifluoromethyl)phenyl]ethyl}urea

Prepared from isoquinoline-5-carboxylic acid and 2-[3-(trifluoromethyl)phenyl]ethylamine. m/z (ES$^+$) 360 (M+H)$^+$.

EXAMPLE 19

N-Isoquinolin-5-yl-N'-{3-[4-(trifluoromethyl)phenyl]propyl}urea

Prepared from isoquinoline-5-carboxylic acid and 3-[4-(trifluoromethyl)phenyl]propylamine (Description 22). m/z (ES$^+$) 374 (M+H)$^+$.

EXAMPLE 20

N-Isoquinolin-8-yl-N'-[4-(trifluoromethyl)benzyl]urea

Prepared from isoquinoline-8-carboxylic acid and 4-(trifluoromethyl)benzylamine. m/z (ES$^+$) 346 M+H)$^+$.

EXAMPLE 21

N-[3-Fluoro-4-(trifluoromethyl)benzyl]-N'-isoquinolin-5-ylurea

Prepared from isoquinoline-5-carboxylic acid and 3-fluoro-4-(trifluoromethyl)benzylamine. m/z (ES$^+$) 364 (M+H)$^+$.

EXAMPLE 22

N-[2-Fluoro-4-(trifluoromethyl)benzyl]-N'-isoquinolin-5-ylurea

Prepared from isoquinoline-5-carboxylic acid and 2-fluoro-4-(trifluoromethyl)benzylamine. m/z (ES$^+$) 364 (M+H)$^+$.

EXAMPLE 23

N-Isoquinolin-5-yl-N'-{3-[3-(trifluoromethyl)phenyl]propyl}urea

Prepared from isoquinoline-5-carboxylic acid and 3-[3-(trifluoromethyl)phenyl]propylamine (Description 23). mn/z (ES$^+$) 374 (M+H)$^+$.

EXAMPLE 24

N-Isoquinolin-5-yl-N'-[4-(trifluoromethoxy)benzyl]urea

Prepared from isoquinoline-5-carboxylic acid and 4-(trifluoromethoxy)benzylamine. m/z (ES$^+$) 362 (M+H)$^+$.

EXAMPLE 25

N-{[6-(4-Fluorophenyl)pyridin-3-yl]methyl}-N'-isoquinolin-5-ylurea

Prepared from isoquinoline-5-carboxylic acid and [6-(4-fluorophenyl)pyridin-3-yl]methylamine (Description 25). m/z (ES$^+$) 373 (M+H)$^+$.

EXAMPLE 26

N-Isoquinolin-8-yl-N'-{3-[4-(trifluoromethyl)phenyl]propyl}urea

Prepared from isoquinoline-8-carboxylic acid and 3-[4-(trifluoromethyl)phenyl]propylamine (Description 22). m/z (ES$^+$) 374 (M+H)$^+$.

EXAMPLE 27

N-Quinolin-5-yl-N'-{3-[4-(trifluoromethyl)phenyl]propyl}urea

Prepared from quinoline-5-carboxylic acid and 3-[4-(trifluoromethyl)phenyl]propylamine (Description 22). m/z (ES$^+$) 374 (M+H)$^+$.

EXAMPLE 28

N-Isoquinolin-8-yl-N'-{3-[3-(trifluoromethyl)phenyl]propyl}urea

Prepared from isoquinoline-8-carboxylic acid and 3-[3-(trifluoromethyl)phenyl]propylamine (Description 23). m/z (ES$^+$) 374 (M+H)$^+$.

EXAMPLE 29

N-Quinolin-5-yl-N'-{3-[3-(trifluoromethyl)phenyl]propyl}urea

Prepared from quinoline-5-carboxylic acid and 3-[3-(trifluoromethyl)phenyl]propylamine (Description 23). m/z (ES$^+$) 374 (M+H)$^+$.

EXAMPLE 30

N-Isoquinolin-8-yl-N'-[4-(trifluoromethoxy)benzyl]urea

Prepared from isoquinoline-8-carboxylic acid and 4-(trifluoromethoxy)benzylamine. m/z (ES$^+$) 362 (M+H)$^+$.

EXAMPLE 31

N-Quinolin-5-yl-N'-[4-(trifluoromethoxy)benzyl]urea

Prepared from quinoline-5-carboxylic acid and 4-(trifluoromethoxy)benzylamine. m/z (ES$^+$) 362 (M+H)$^+$.

EXAMPLE 32

N-(2,3-Dihydro-1H-inden-2-ylmethyl)-N'-isoquinolin-5-ylurea

Prepared from isoquinoline-5-carboxylic acid and 2,3-dihydro-1H-inden-2-ylmethylamine. m/z (ES$^+$) 318 (M+H)$^+$.

EXAMPLE 33

N-Isoquinolin-5-yl-N'-(4-phenylcyclohexyl)urea

Prepared from isoquinoline-5-carboxylic acid and 4-phenylcyclohexylamine. m/z (ES$^+$) 346 (M+H)$^+$.

EXAMPLE 34

N-Isoquinolin-5-yl-N'-(6,7,8,9-tetrahydro-5H-benzo[α][7]annulen-6-ylmethyl)urea

Prepared from isoquinoline-5-carboxylic acid and 6,7,8,9-tetrahydro-5H-benzo[α][7]annulen-6-ylmethylamine hydrochloride (Description 26). m/z (ES$^+$) 346 (M+H)$^+$.

EXAMPLE 35

N-Isoquinolin-5-yl-N'-(6,7,8,9-tetrahydro-5H-benzo[α][7]annulen-7-ylmethyl)urea

Prepared from isoquinoline-5-carboxylic acid and 6,7,8,9-tetrahydro-5H-benzo[α][7]annulen-7-ylmethylamine hydrochloride (Description 28). m/z (ES$^+$) 346 (M+H)$^+$.

EXAMPLE 36

N-isoquiuolin-5-yl-N'-{[5-(trifluoromethyl)pyridin-2-yl]methyl}urea

Prepared from isoquinoline-5-carboxylic acid and 2-aminomethyl-5-(trifluoromethyl)pyridine (Description 2). m/z (ES$^+$) 347 (M+H)$^+$.

EXAMPLE 37

N-[(4-tert-Butylpyridin-2-yl)methyl]-N'-isoquinolin-5-ylurea

Prepared from isoquinoline-5-carboxylic acid and 2-aminomethyl-4-tert-butylpyridine (Description 5). m/z (ES$^+$) 335 (M+H)$^+$.

EXAMPLE 38

N-[(6-tert-Butylpyridin-3-yl)methyl]-N'-isoquinolin-5-ylurea

Prepared from isoquinoline-5-carboxylic acid and 3-aminomethyl-6-tert-butylpyridine (Description 11). m/z (ES$^+$) 335 M+H)$^+$.

EXAMPLE 39

N-[(2-tert-Butylpyridin-4-yl)methyl]-N'-isoquinolin-5-ylurea

Prepared from isoquinoline-5-carboxylic acid and 4-aminomethyl-2-tert-butylpyridine (Description 13). m/z (ES$^+$) 335 (M+H)$^+$.

EXAMPLE 40

N-[(6-tert-Butylpyridin-2-yl)methyl]-N'-isoquinolin-5-ylurea

Prepared from isoquinoline-5-carboxylic acid and 2-aminomethyl-6-tert-butylpyridine (Description 16). m/z (ES$^+$) 335 (M+H)$^+$.

EXAMPLE 41

N-Isoquinolin-5-yl-N'-{[6-(trifluoromethyl)pyridin-3-yl]methyl}urea

Prepared from isoquinoline-5-carboxylic acid and 3-aminomethyl-6-(trifluoromethyl)pyridine. m/z (ES$^+$) 347 (M+H)$^+$.

EXAMPLE 42

N-Isoquinolin-5-yl-N'-{3-[6-(trifluoromethyl)pyridin-3-yl]propyl}urea

Prepared from isoquinoline-5-carboxylic acid and 3-[6-(trifluoromethyl)pyridin-3-yl]propylamine (Description 18). m/z (ES$^+$) 375 (M+H)$^+$.

EXAMPLE 43

N-Isoquinolin-5-yl-N'-[3-(1H-pyrazol-1-yl)benzyl]urea

Prepared from isoquinoline-5-carboxylic acid and 3-(1H-pyrazol-1-yl)benzylamine hydrochloride (Description 29). m/z (ES$^+$) 344 (M+H)$^+$.

EXAMPLE 44

N-Isoquinolin-5-yl-N'-[4-(1H-pyrazol-1-yl)benzyl]urea

Prepared from isoquinoline-5-carboxylic acid and 4-(1H-pyrazol-1-yl)benzylamine hydrochloride (Description 30). m/z (ES$^+$) 344 (M+H)$^+$.

EXAMPLE 45

N-Isoquinolin-5-yl-N'-[(2-phenyl-1,3-thiazol-5-yl)methyl]urea

Prepared from isoquinoline-5-carboxylic acid and (2-phenyl-1,3-thiazol-5-yl)methylamine. m/z (ES$^+$) 361 (M+H)$^+$.

EXAMPLE 46

N-Isoquinolin-5-yl-N'-[(2-thien-2-yl-1,3-thiazol-4-yl)methyl]urea

Prepared from isoquinoline-5-carboxylic acid and (2-thien-2-yl-1,3-thiazol-4-yl)methylamine. m/z (ES$^+$) 367 (M+H)$^+$.

EXAMPLE 47

N-Isoquinolin-5-yl-N'-[(4-phenyl-1,3-thiazol-2-yl)methyl]urea

Prepared from isoquinoline-5-carboxylic acid and (4-phenyl-1,3-thiazol-2-yl)methylamine. m/z (ES$^+$) 361 (M+H)$^+$.

EXAMPLE 48

N-Isoquinolin-5-yl-N'-[(2-phenyl-1,3-thiazol-4-yl)methyl]urea

Prepared from isoquinoline-5-carboxylic acid and (2-phenyl-1,3-thiazol-4-yl)methylamine. m/z (ES$^+$) 361 (M+H)$^+$.

EXAMPLE 49

N-Isoquinolin-5-yl-N'-[2-(4-phenyl-1,3-thiazol-2-yl)ethyl]urea

Prepared from isoquinoline-5-carboxylic acid and 2-(4-phenyl-1,3-thiazol-2-yl)ethylamine. m/z (ES$^+$) 375 (M+H)$^+$.

EXAMPLE 50

N-Isoquinolin-5-yl-N'-[(5-phenylisoxazol-3-yl)methyl]urea

Prepared from isoquinoline-5-carboxylic acid and (5-phenylisoxazol-3-yl)methylamine. m/z (ES$^+$) 345 (M+H)$^+$.

EXAMPLE 51

N-Isoquinolin-5-yl-N'-[(3-nhenrlisoxazol-5-yl)methyl]urea

Prepared from isoquinoline-5-carboxylic acid and (3-phenylisoxazol-5-yl)methylamine. m/z (ES$^+$) 345 (M+H)$^+$.

EXAMPLE 52

N-(8-Fluoroisoquiolin-5-yl)-N'-[4-(trifluoromethyl)benzyl]urea

Prepared from 8-fluoroisoquinolin-5-amine (Description 43) and [4-(trifluoromethyl)benzyl]isocyanate (Description 58) according to the procedure of Description 61. m/z (ES$^+$) 364 (M+H)$^+$.

EXAMPLE 53

N-Isoquinolin-5-yl-N-methyl-N'-[4-(trifluoromethyl)benzyl]urea

Sodium hydride (60% dispersion in oil, 7 mg, 0.17 mmol) was added to a suspension N-isoquinolin-5-yl-N'-[4-(trifluoromethyl)benzyl]urea (Example 14; 48 mg, 0.14 mmol) in THF (3 mL) at room temperature and the reaction was stirred until effervescence ceased (20 minutes). Methyl iodide (11 μL, 0.17 mmol) was added and the reaction stirred at room temperature for 3 hours. TLC analysis (10% MeOH in CH$_2$Cl$_2$) indicated only one major product. The reaction was evaporated in vacuo and the product isolated by preparative TLC (4% MeOH in CH$_2$Cl$_2$) to give the title compound. m/z (ES$^+$) 360 (M+H)$^+$.

Examples 54 to 60 were prepared according to the procedure of Description 60.

EXAMPLE 54

N'-Isoquinolin-5-yl-N-methyl-N-[4-(trifluoromethyl)benzyl]urea

Prepared from isoquinoline-5-carboxylic acid and N-methyl-N-[4-(trifluoromethyl)benzyl]amine (Description 31). m/z (ES$^+$) 190 (M+H)$^+$.

EXAMPLE 55

N-Isoquinolin-5-yl-N'-{1-[4-(trifluoromethyl)phenyl]ethyl}urea

Prepared from isoquinoline-5-carboxylic acid and 1-[4-(trifluoromethyl)phenyl]ethylamine (Description 32). m/z (ES$^+$) 360 (M+H)$^+$.

EXAMPLE 56

N-(1,3-Diphenylpropyl)-N'-isoquinolin-5-ylurea

Prepared from isoquinoline-5-carboxylic acid and 1,3-diphenylpropylamine (Description 33). m/z (ES$^+$) 382 (M+H)$^+$.

EXAMPLE 57

N-Isoquiolin-5-yl-N'-[(3-phenyl-1,2,4-oxadiazol-5-yl)methyl]urea

Prepared from isoquinoline-5-carboxylic acid and (3-phenyl-1,2,4-oxadiazol-5-yl)methylamine hydrochloride (Description 34). m/z (ES$^+$) 346 (M+H)$^+$.

EXAMPLE 58

N-[(2-Benzyl-1,3-thiazol-4-yl)methyl]-N'-isoquinolin-5-ylurea

Prepared from isoquinoline-5-carboxylic acid and 2-benzyl-1,3-thiazol-4-yl)methylamine (Description 35). m/z (ES$^+$) 375 (M+H)$^+$.

EXAMPLE 59

N-Isoquinolin-5-yl-N'-{[1-(2-methylphenyl)-1H-pyrazol-4-yl]methyl}urea

Prepared from isoquinoline-5-carboxylic acid and [1-(2-methylphenyl)-1H-pyrazol-4-yl]methylamine (Description 36). m/z (ES$^+$) 358 (M+H)$^+$.

EXAMPLE 60

N-(3-Methoxyisoquinolin-8-yl)-N'-[4-(trifluoromethyl)benzyl]urea

Prepared from 3-methoxyisoquinoline-8-carboxylic acid (Description 56) and 4-(trifluoromethyl)benzylamine. m/z (ES$^+$) 376 (M+H)$^+$.

EXAMPLE 61

N-Cinnolin-5-yl-N'-[4-(trifluoromethyl)benzyl]urea

Prepared from cinnolin-5-amine (*Sci Pharm.* 1982, 50, 246) and [4-(trifluoromethyl)benzyl]isocyanate (Description 58) according to the procedure of Description 61. m/z (ES$^+$) 347 (M+H)$^+$.

Examples 62 to 64 were prepared according to the procedure of Description 60.

EXAMPLE 62

N-(4-tert-Butylbenzyl)-N'-cinnolin-5-ylurea

Prepared from cinnolin-5-amine (*Sci Pharm.* 1982, 50, 246) and (4-tert-butylbenzyl)acetic acid. m/z (ES$^+$) 335 (M+H)$^+$.

EXAMPLE 63

N-(3-Cyclohexylpropyl)-N'-isoquinolin-5-ylurea

Prepared from isoquinoline-5-carboxylic acid and 3-cyclohexylpropylamine hydrochloride (Description 37). m/z (ES$^+$) 312 (M+H)$^+$.

EXAMPLE 64

N-Isoquinolin-5-yl-N'-(6,7,8,9-tetrahydro-5H-benzo[α][7]annulen-7-yl)urea

Prepared from isoquinohn-5-amine and 6,7,8,9-tetrahydro-5H-benzo[α][7]annulene-7-carboxylic acid Description 38). m/z (ES$^+$) 332 (M+H)$^+$.

EXAMPLE 65

N-Isoquinolin-5-yl-N'-[4-(trifluoromethyl)benzyl]thiourea

To a solution of 1,1'-thiocarbonyldi-2(1H)-pyridone (330 mg, 1.4 mmol) in dichloromethane (13 ml) under nitrogen was added, dropwise, a solution of 4-(trifluoromethyl)benzylamine (200 μl, 1.4 mmol) in dichloromethane (10 ml). The solution was stirred at room temperature for 16 hours. 5-Aminoisoquinoline (245 mg, 0.0017 mol) was added to the reaction mixture, which was then heated at reflux for 2 days and evaporated Preparative TLC (eluant 5% methanol/95% dichloromethane) gave a product band also containing 5-aminoisoquinoline. The mixed product (230 mg) was dissolved in acetonitrile (40 ml) and tetrafluorophthalic anhydride (700 mg, 3.2 mmol) was added. The reaction was stirred at room temperature for 16 hours. Ethyl acetate (60 ml) was added to the reaction mix which was then washed with saturated aqueous sodium bicarbonate (3×20 ml). The organic extract was evaporated and the residue purified by preparative TLC (eluant system 5% methanol/95% dichloromethane) to give the title compound (77 mg, 23%). m/z (ES$^+$) 362 (M+1)$^+$.

EXAMPLE 66

N-Isoquinolin-6-yl-N'-[4-(trifluoromethyl)benzyl]urea

Prepared from 6-aminoisoquinoline (Description 51) and [4-(trifluoromethyl)benzyl]isocyanate (Description 58) according to the procedure of Description 61. m/z (ES$^+$) 346 (M+H)$^+$.

EXAMPLE 67

N-Isoquinolin-6-yl-N'-[4-(trifluoromethoxy)benzyl]urea

Prepared from 6-aminoisoquinoline (Description 51) and [4-(trifluoromethoxy)benzyl]isocyanate (Description 59) according to the procedure of Description 61. m/z (ES$^+$) 362 (M+H)$^+$.

EXAMPLE 68

N-(3-Methylisoquinolin-5-yl)-N'-[4-(trifluoromethyl)benzyl]urea

Prepared from 3-methylisoquinolin-5-amine (Description 45) and [4-(trifluoromethyl)benzyl]isocyanate (Description 58) according to the procedure of Description 61. m/z (ES$^+$) 360 (M+H)$^+$.

EXAMPLE 69

N-(1-Chloroisoquinolin-5-yl)-N'-[4-(trifluoromethyl)benzyl]urea

Prepared from 1-chloroisoquinolin-5-amine (1Description 48) and [4-(trifluoromethyl)benzyl]isocyanate (Description 58) according to the procedure of Description 61. m/z (ES$^+$) 380, 382 (M+H)$^+$.

EXAMPLE 70

N-[1-(Dimethylamino)isoquinolin-5-yl]-N'-[4-(trifluoromethyl)benzyl]urea

N-(1-Chloroisoquinolin-5-yl)-N'-(4-trifluoromethylbenzyl)urea (Example 69; 60 mg) was suspended in ethanol (5 ml). Ethanolic dimethylamine (33%, 2 ml) was added and the mixture heated to 100° C. in a sealed tube for 16 hours after which time TLC indicated complete reaction. The reaction mixture was evaporated and the residue purified by preparative thin layer chromatography (5% methanol-dichloromethane eluant) to give the title compound (20 mg). m/z (ES$^+$) 389 (M+H)$^+$.

EXAMPLE 71

N-(3-Methylisoquinolin-5-yl)-N'-[4-(trifluoromethoxy)benzyl]urea

Prepared from 3-methylisoquinolin-5-amine (Description 45) and [4-(trifluoromethoxy)benzyl]isocyanate (Description 59) according to the procedure of Description 61. m/z (ES$^+$) 376 (M+H)$^+$.

EXAMPLE 72

N-(3-Methylisoquinolin-8-yl)-N'-[4-(trifluoromethyl)benzyl]urea

A sample of 3-methyl-5-nitroisoquinoline (Description 44) enriched in the nitration byproduct 3-methyl-8-nitroisoquinoline was reduced according to Description 45 and the mixture of amines reacted with [4-(trifluoromethyl)benzyl] isocyanate (Description 58) according to the procedure of Description 61. Isomer separation of the products gave the title compound. m/z (ES$^+$) 360 (M+H)$^+$.

EXAMPLE 73

N-(3-Chloroisoquiolin-5-yl)-N'-[4-(trifluoromethyl)benzyl]urea

Prepared from 3-chloroisoquinolin-5-amine (Description 50) and [4-(trifluoromethyl)benzyl]isocyanate (Description 58) according to the procedure of Description 61. m/z (ES$^+$) 380, 382 (M+H)$^+$.

EXAMPLE 74

N-(3-Methylcinnolin-5-yl)-N'-[4-(trifluoromethyl)benzyl]urea

Prepared from 3-methylcinnolin-5-amine and [4-(trifluoromethyl)benzyl]isocyanate (Description 58) according to the procedure of Description 61. m/z (ES$^+$) 361 (M+H)$^+$.

EXAMPLE 75

N-Cinnolin-5-yl-N'-[4-(trifluoromethoxy)benzyl]urea

Prepared from cinnolin-5-amine [*Sci Pharm.* 1982, 50, 246] and [4-(trifluoromethoxy)benzyl]isocyanate (Description 59) according to the procedure of Description 61. m/z (ES$^+$) 363 (M+H)$^+$.

EXAMPLE 76

N-(1-hydroxyisoquinolin-5-yl)-N'-[4-(trifluoromethyl)benzyl]urea

N-(1-chloroisoquinolin-5-yl)-N'-[4-(trifluoromethyl)benzyl]urea (Example 69; 47 mg, 0.12 mmol) was added to a mixture of 3N HCl (aq. 5 ml) and THF (1 ml). The mixture was heated at 90° C. for 20 hours, then 5N HCl (aq. 2 ml) was added and the reaction heated at 90° C. for a further 20 hours. After cooling to room temperature, ethyl acetate (20 ml) was added and the layers separated (some solid was suspended in the organic layer). The organic phase was washed with saturated aqueous NaHCO$_3$ (20 ml), then evaporated. The residue was triturated in refluxing isopropyl alcohol (5 ml), then cooled to room temperature. The white solid was collected by filtration and washed with isopropyl alcohol (2×1 ml) to give the title compound (22 mg). m/z (ES$^+$) 362 (M+H)$^+$.

EXAMPLE 77

N-[4-(trifluoromethyl)benzyl]-N'-[3-(trifluoromethyl)isoquinolin-5-yl]urea

Prepared from 3-(trifluoromethyl)isoquinolin-5-amine (Description 64) and [4-(trifluoromethyl)benzyl]isocyanate (Description 58) according to the procedure of Description 61. m/z (ES$^+$) 414 (M+H)$^+$.

EXAMPLE 78

N-(1-chloro-3-ethylisoquinolin-5-yl)-N'-[4-(trifluoromethyl)benzyl]urea

Prepared from 1-chloro-3-ethylisoquinolin-5-amine (Description 66) and [4-(trifluoromethyl)benzyl]isocyanate (Description 58) according to the procedure of Description 61. m/z (ES$^+$) 408, 410 (M+H)$^+$.

The following quinolin-6-yl derivatives were also prepared by similar methodology:

EXAMPLE 79

N-phenyl-N'-[quinolin-6-yl]urea

Prepared from 6-aminoquinoline and phenyl isocyanate. m/z (ES$^+$) 264 (M+H)$^+$.

EXAMPLE 80

N-(2-naphthyl)-N'-[quinolin-6-yl]urea

Prepared from 6-aminoquinoline and 2-naphthyl isocyanate. m/z (ES$^+$) 314 (M+H)$^+$.

EXAMPLE 81

N-(4-nitrophenyl)-N'-[quinolin-6-yl]urea

Prepared from 6-aminoquinoline and 4-nitrophenyl isocyanate. m/z (ES$^+$) 309 (M+H)$^+$.

EXAMPLE 82

N-[3,5-bis(trifluoromethyl)phenyl]-N'-[quinolin-6-yl]urea

Prepared from 6-aminoquinoline and 3,5-bis(trifluoromethyl)phenyl isocyanate. m/z (ES$^+$) 400 (M+H)$^+$.

EXAMPLE 83

N-(4-phenoxyphenyl)-N'-[quinolin-6-yl]urea

Prepared from 6-aminoquinoline and 4-phenoxyphenyl isocyanate. m/z (ES$^+$) 356 (M+H)$^+$.

EXAMPLE 84

N-(4-acetylphenyl)-N'-[quinolin-6-yl]urea

Prepared from 6-aminoquinoline and 4-acetylphenyl isocyanate. m/z (ES$^+$) 306 (M+H)$^+$.

EXAMPLE 85

N-benzyl-N'-[quinolin-6-yl]urea

Prepared from 6-aminoquinoline and benzyl isocyanate. m/z (ES$^+$) 278 (M+H)$^+$.

EXAMPLE 86

N-[quinolin-6-yl]-N'-[4-(trifluoromethoxy)phenyl]urea

Prepared from 6-aminoquinoline and 4-(trifluoromethoxy)phenyl isocyanate. m/z (ES$^+$) 348 (M+H)$^+$.

EXAMPLE 87

N-(4-cyanophenyl)-N'-[quinolin-6-yl]urea

Prepared from 6-aminoquinoline and 4-cyanophenyl isocyanate. m/z (ES$^+$) 289 (M+H)$^+$.

EXAMPLE 88

N-(1,1'-biphenyl-4-yl)-N'-[quinolin-6-yl]urea

Prepared from 6-aminoquinoline and 4-biphenyl isocyanate. m/z (ES$^+$) 340 (M+H)$^+$.

EXAMPLE 89

N-[4-(dimethylamino)phenyl]-N'-[quinolin-6-yl]urea

Prepared from 6-aminoquinoline and 4-(dimethylamino)phenyl isocyanate. m/z (ES$^+$) 307 (M+H)$^+$.

EXAMPLE 90

N-(1,3-benzodioxol-5-yl)-N'-[quinolin-6-yl]urea

Prepared from 6-aminoquinoline and 3,4-(methylenedioxy)phenyl isocyanate. m/z (ES$^+$) 308 (M+H)$^+$.

EXAMPLE 91

N-cyclohexyl-N'-[quinolin-6-yl]urea

Prepared from 6-aminoquinoline and cyclohexyl isocyanate. m/z (ES$^+$) 270 (M+H)$^+$.

EXAMPLE 92

N-[(+/−)-1-phenylethyl]-N'-[quinolin-6-yl]urea

Prepared from 6-aminoquinoline and (+/−)-1-phenylethyl isocyanate. m/z (ES$^+$) 292 (M+H)$^+$.

The above exemplified compounds of the present invention have been tested in the following assay and generally possess an IC$_{50}$<1 µM and, in the majority of cases, <200 nM.

BIOLOGICAL METHODOLOGY

Determination of in vitro Activity

CHO cells, stably expressing recombinant human VR1 receptors and plated into black-sided 384-well plates, were washed twice with assay buffer (Hepes-buffered saline) and then incubated with 1 uM Fluo-3-AM for 60 minutes in darkness. Cells were washed twice more to remove excess dye, before being placed, along with plates containing capsaicin and test compounds in a Molecular Devices FLIPR. The FLIPR simultaneously performed automated pharmacological additions and recorded fluorescence emmission from Fluo-3. In all experiments, basal fluorescence was recorded, before addition of test compounds and subsequent addition of a previously determined concentration of capsaicin that evoked 80% of the maximum respsonse. Inhibition of capsaicin evoked increases in intracellular [Ca$^{2+}$] were expressed relative to wells on the same plate to which capcaicin was added in the absence of test compounds. Increases in intracellular [Ca$^{2+}$] occuring after addition of test compound alone, prior to addition of capsaicin, allow determination of intrinsic agonist or partial agonist activity, if present.

Determination of in vivo Efficacy in a Capsaicin Paw Flinch Model (Method adapted from Taniguchi et al, 1997, *Br J Pharinacol.* 122(5):809-12) To determine in vivo functional occupancy of VR1 receptors, compounds are administered orally to male Sprague Dawley rats typically 1 hour prior to receiving an intraplantar injection of capsaicin (2 µg dissolved in ethanol) and the number of flinches of the injected paw is recorded for 5 minutes immediately thereafter. Statistical analysis is performed using one-way ANOVA followed by Dunnett's test; p values <0.05 compared to capsaicin/vehicle-treated rats are considered significant.

Determination of in vivo Efficacy in a Model of Inflammatory Pain (Method adapted from Hargreaves et al, 1988 *Pain,* 32(1):77-88). Antinociceptive activity is determined using a rat carrageenan-induced thermal hyperalgesia assay. Inflammatory hyperalgesia is induced by intraplantar injection of carrageenan (lambda-carrageenan 0.1 ml of 1% solution made up in saline) into one hind paw. Compounds are given orally typically 2 hours after carrageenan and paw withdrawal latencies determined 1 hour later. Paw withdrawal latencies to application of noxious thermal stimuli to plantar surface of the hind paw are measured using the Hargreaves apparatus. Thermal hyperalgesia is defined as the difference in paw withdrawal latencies for saline/vehicle- and carrageenan/vehicle-treated rats. Paw wthdrawal latencies for drug treated rats are expressed as a percentage of this response. Statistical analysis is performed using one-way ANOVA followed by Dunnett's test; p values <0.05 compared to carrageenan/vehicle-treated rats are considered significant.

EXAMPLE 93

N-(1-Methylisoquinolin-5-yl)-N'-[4-(trifluoromethyl)benzyl]urea

Prepared from 1-methylisoquinolin-5-amine (Description 68) and [4-(trifluoromethyl)benzyl]isocyanate (Description 58) according to the procedure of Description 61. m/z (ES$^+$) 360 (M+H)$^+$.

EXAMPLE 94

N-(1-Methylisoquinolin-5-yl)-N'-[4-(trifluoromethoxy)benzyl]urea

Prepared from 1-methylisoquinolin-5-amine (Description 68) and [4-(trifluoromethoxy)benzyl]isocyanate (Description 59) according to the procedure of Description 61. m/z (ES$^+$) 376 (M+H)$^+$.

EXAMPLE 95

N-(6,8-Difluoro-3-methylisoquinolin-5-yl)-N'-[4-(trifluoromethyl)benzyl]urea

Prepared from 6,8-difluoro-3-methylisoquinolin-5-amine (Description 73) and [4-(trifluoromethyl)benzyl]isocyanate (Description 58) according to Description 61. m/z (ES$^+$) 396 (M+H)$^+$.

EXAMPLE 96

N-[3-Methyl-7-(trifluoromethyl)isoquinolin-5-yl]-N'-[4-(trifluoromethyl)benzyl]urea Prepared from 3-methyl-7-(trifluoromethyl)isoquinolin-5-amine (Description 74) and [4-(trifluoromethyl)benzyl]isocyanate (Description 58) according to Description 61. m/z (ES$^+$) 428 (M+H)$^+$.

EXAMPLE 97

N-(8-Fluoro-3-methylisoquinolin-5-yl)-N'-[4-(trifluoromethyl)benzyl]urea

Prepared from 8-fluoro-3-methylisoquinolin-5-amine (Description 76) and [4-(trifluoromethyl)benzyl]isocyanate (Description 58) according to Description 61. m/z (ES$^+$) 378 (M+H)$^+$.

EXAMPLE 98

N-(6-Fluoro-3-methylisoquinolin-5-yl)-N'-[4-(trifluoromethyl)benzyl]urea

Prepared from 6-fluoro-3-methylisoquinolin-5-amine (Description 79) and [4-(trifluoromethyl)benzyl]isocyanate (Description 58) according to Description 61. m/z (ES$^+$) 378 (M+H)$^+$.

EXAMPLE 99

N-(6-Fluoro-3-methylisoquinolin-5-yl)-N'-[4-(trifluoromethoxy)benzyl]urea

Prepared from 6-fluoro-3-methylisoquinohn-5-amine (Description 79) and [4-(trifluoromethoxy)benzyl]isocyanate (Description 59) according to Description 61. m/z (ES$^+$) 394 (M+H)$^+$.

EXAMPLE 100

N-(3-Methylcinnolin-5-yl)-N'-[4-(trifluoromethoxy)benzyl]urea

Prepared from 3-methylcinnolin-5-amine and [4-(trifluoromethoxy)benzyl]isocyanate (Description 59) according to the procedure of Description 61. m/z (ES$^+$) 377 (M+H)$^+$.

EXAMPLE 101

N-(7-Methoxyisoquinolin-5-yl)-N-'-[4-(trifluoromethyl)benzyl]urea

Prepared from 7-methoxyisoquinolin-5-amine (Description 82) and [4-(trifluoromethyl)benzyl]isocyanate (Description 58) according to Description 61. m/z (ES$^+$) 376 (M+H)$^+$.

EXAMPLE 102

N-(1,3-Dimethylisoquinolin-5-yl)-N'-[4-(trifluoromethyl)benzyl]urea

Prepared from 1,3-dimethylisoquinolin-5-amine (Description 83) and [4-(trifluoromethyl)benzyl]isocyanate (Description 58) according to Description 61. m/z (ES$^+$) 374 (M+H)$^+$.

EXAMPLE 103

N-(7-Chloro-3-methylisoquiolin-5-yl)-N'-[4-(trifluoromethyl)benzyl]urea

Prepared from 7-chloro-3-methylisoquinolin-5-amine (Description 86) and [4-(trifluoromethyl)benzyl]isocyanate (Description 58) according to Description 61. m/z (ES$^+$) 394 (M+H)$^+$.

EXAMPLE 104

N-(7-Chloroisoquinolin-5-yl)-N'-[4-(trifluoromethyl)benzyl]urea

Prepared from 7-chloroisoquinolin-5-amine (Description 87) and [4-(trifluoromethyl)benzyl]isocyanate (Description 58) according to Description 61. m/z (ES$^+$) 380 (M+H)$^+$.

EXAMPLE 105

N-(8-Fluoro-3-methoxyisoquinolin-5-yl)-N'-[4-(trifluoromethyl)benzyl]urea

Prepared from 8-fluoro-3-methoxyisoquinoline-5-carboxylic acid (Description 88) and 4-(trifluoromethyl)benzylamine according to Description 60. m/z (ES$^+$) 394 (M+H)$^+$.

EXAMPLE 106

N-(6-Fluoroisoquinolin-5-yl)-N'-[4-(trifluoromethyl)benzyl]urea

Prepared from 6-fluoroisoquinolin-5-amine (Description 89) and [4-(trifluoromethyl)benzyl]isocyanate (Description 58) according to Description 61. m/z (ES$^+$) 364 (M+H)$^+$.

EXAMPLE 107

N-(6-Fluoroisoquinolin-5-yl)-N'-[4-(trifluoromethoxy)benzyl]urea

Prepared from 6-fluoroisoquinolin-5-amine (Description 89) and [4-(trifluoromethoxy)benzyl]isocyanate (Description 59) according to Description 61. m/z (ES$^+$) 394 (M+H)$^+$.

EXAMPLE 108

N-(7-Fluoroisoquinolin-5-yl)-N'-[4-(trifluoromethyl)benzyl]urea

Prepared from 7-fluoroisoquinolin-5-amine (Description 90) and [4-(trifluoromethyl)benzyl]isocyanate (Description 58) according to Description 61. m/z (ES$^+$) 364 (M+H)$^+$.

EXAMPLE 109

N-(4-Methylisoquinolin-5-yl)-N'-[4-(trifluoromethyl)benzyl]urea

Prepared from 4-methylisoquinolin-5-amine (Description 91) and [4-(trifluoromethyl)benzyl]isocyanate (Description 58) according to Description 61. m/z (ES$^+$) 360 (M+H)$^+$.

EXAMPLE 110

N-[8-(trifluoromethyl)isoquinolin-5-yl]-N'-[4-(trifluoromethyl)benzyl]urea

To a solution of 8-(trifluoromethyl)isoquinolin-5-amine (Description 93; 150 mg, 0.708 mmol) in CDCl$_3$ (10 ml) was added [4-(trifluoromethyl)benzyl]isocyanate (Description 58) [0.506M soln in DCM; 1.403 ml, 0.71 mmol) and the resulting mixture heated at reflux overnight. NMR analysis showed a deficit of the [4-(trifluoromethyl)benzyl]isocyanate in comparison to remaining 8-(trifluoromethyl)isoquinolin-5-amine so a further portion of [4-(trifluoromethyl)benzyl]isocyanate [0.506M solution in DCM] (1.403 ml; 0.71 mmol) was added and refluxing continued for 2 days. The cooled reaction mixture was evaporated to dryness and purified by column chromatography on silica elution with 1% MeOH in DCM+0.5% NH$_4$OH. NMR showed the product was the bis acylated urea. This material was dissolved in methanol (5 ml) and K$_2$CO$_3$ (500 mg, 3.6 mmol) added and the mixture stirred at room temperature for 2.5 hours. The mixture was filtered and the residue purified by preparative TLC eluting with 10% MeOH in DCM+0.5% NH$_4$OH to give the title compound (100 mg, 34%) as a white solid. m/z (ES$^+$) 414 (M+H)$^+$.

EXAMPLE 111

N-[6-(trifluoromethyl)isoquinolin-5-yl]-N'-[4-(trifluoromethyl)benzyl]urea

To a solution of 6-(trifluoromethyl)isoquinolin-5-amine (Description 98; 100 mg, 0.47 mmol) in anhydrous toluene (5 ml) was added [4-(trifluoromethyl)benzyl]isocyanate (Description 58) [0.506M soln in DCM] (1.88 ml; 0.94 mmol) and the mixture heated at reflux overnight. Further [4-(trifluoromethyl)benzyl]isocyanate [0.506M soln in DCM] (1.88 ml; 0.94 mmol) was added and heating continued for 4 days. The toluene was removed, the residue dissolved in methanol (10 ml) and a spatula end of potassium carbonate added. The mixture was then heated at reflux for 15 mins. The mixture was cooled and filtered and the filtrate evaporated. The residue was purified by mass directed HPLC to give the title compound (8 mg, 4%) as a white solid. m/z (ES$^+$) 414 (M+H)$^+$.

EXAMPLE 112

N-[7-(trifluoromethyl)isoquinolin-5-yl]-N'-[4-(trifluoromethyl)benzyl]urea

Prepared from 7-(trifluoromethyl)isoquinolin-5-amine (Description 99) and [4-(trifluoromethyl)benzyl]isocyanate (Description 58) according to Description 61. m/z (ES$^+$) 414 (M+H)$^+$.

EXAMPLE 113

N-[7-(trifluoromethyl)isoquinolin-5-yl]-N'-[4-(trifluoromethoxy)benzyl]urea

Prepared from 7-(trifluoromethyl)isoquinolin-5-amine (Description 99) and [4-(trifluoromethoxy)benzyl]isocyanate (Description 59) according to Description 61. m/z (ES$^+$) 414 (M+H)$^+$.

EXAMPLE 114

N-(6-Fluoro-1-methylisoquinolin-5-yl)-N'-[4-(trifluoromethyl)benzyl]urea

Prepared from 6-fluoro-1-methylisoquinolin-5-amine (Description 103) and [4-(trifluoromethyl)benzyl]isocyanate (description 58) according to the procedure of description 61. m/z (ES$^+$) 378 (M+H)$^+$.

EXAMPLE 115

N-(1-Cyanoisoquinolin-5-yl)-N'-[4(trifluoromethyl)benzyl]urea

To a solution of N-(1-chloroisoquinolin-5-yl)-N'-[4-(trifluoromethyl)benzyl]urea (Example 69) (250 mg, 0.7 mmol) in DMF (5 ml) was added zinc cyanide (43 mg, 0.37 mmol) and tetrakis(triphenylphosphine)palladium (76 mg, 0.07 mmol). The reaction was heated at 80° C., under an atmosphere of nitrogen, for 72 hr, with the addition of extra tetrakis(triphenylphosphine)palladium (76 mg, 0.07 mmol) after 16 hr. Reaction mixture was quenched with water and extracted with ethyl acetate (3×5 ml), dried over MgSO$_4$ and evaporated. The residue was purified by flash column chromatography using an eluant system of 3% methanol/97% DCM increasing to 5% MeOH/95% DCM. Recrystallisation in ethanol of a small portion of product gave a pure sample of the title compound (50 mg, 65.6%). m/z (ES$^+$) 371, 373 (M+H)$^+$.

EXAMPLE 116

N-[1-(Methoxycarbonyl)isoquinolin-5-yl]-N'-[4-(trifluoromethyl)benzyl]urea

Prepared from methyl 5-aminoisoquinoline-1-carboxylate (Description 106) and [4-(trifluoromethyl)benzyl]isocyanate (description 58) according to the procedure of description 61. m/z (ES$^+$) 404 (M+H)$^+$.

EXAMPLE 117

N-(1-Carboxyisoquinolin-5-yl)-N'-[4-(trifuoromethyl)benzyl]urea

N-[1-(Methoxycarbonyl)isoquinolin-5-yl]-N'-[4-(trifluoromethyl)benzyl]urea (Example 116, 55 mg, 0.136 mmol) was dissolved in a mixture of THF (3 ml), methanol (1 ml) and water (1 ml), then lithium hydroxide monohydrate (6 mg, 0.14 mmol) was added. The reaction was stirred at room temperature until all the ester had been consumed, then the solvents were evaporated and 5% aqueous $NaH_2PO_4$ solution (pH 4, 5 ml) was added to the residue. After stirring for 15 min. the pale yellow solid was collected by filtration, washed with water (2 ml) and dried under vacuum to give the title compound (39 mg, 73%). m/z (ES$^+$) 390 (M+H)$^+$.

EXAMPLE 118

N-(1-Aminoisoquinolin-5-yl)-N'-[4-(trifluoromethyl)benzyl]urea

A mixture of N-(1-carboxyisoquinolin-5-yl)-N'-[4-(trifluoromethyl)benzyl]urea (Example 117, 309 mg, 0.794 mmol), diphenylphosphoryl azide (210 μl, 0.975 mmol) and triethylamine (210 μl, 1.50 mmol) in 1,4-dioxane (25 ml) was heated at 100° C., under a nitrogen atmosphere for 1.5 h. Water (0.25 ml) was then added and the reaction mixture heated for a further 1 hour. The reaction mixture was then cooled to room temperature, filtered and the filtrate evaporated. The residue was purified using a Bond-Elut SCX ion-exchange cartridge, first eluting non-basic materials with methanol, then eluting the product with 2M methanolic ammonia. The basic fractions were evaporated and further purified by flash column chromatography (eluant 5% MeOH-95% dichloromethane increasing to 10% MeOH-90% dichloromethane). The product was then passed through a second SCX purification to give the title compound (77 mg, 27%). m/z (ES$^+$) 361 (M+H)$^+$.

EXAMPLE 119

N-[1-(Hydroxymethyl)isoquinolin-5-yl]-N'-[4-(trifluoromethyl)benzyl]urea

N-[1-(Methoxycarbonyl)isoquinolin-5-yl]-N'-[4-(trifiluoromethyl)benzyl]urea (Example 116, 70 mg, 0.174 mmol) was suspended in a mixture of THF (5 ml) and toluene (5 ml). Lithium borohydride (50 mg, 2.27 mmol) was added and the reaction mixture heated at 60° C. for 1 hour. The reaction was cooled to room temperature and allowed to stand for 1 week. The crystalline product was collected by filtration, washed with toluene (2 ml), then triturated with 1:1 TBF-dichloromethane (2 ml), triturated again with THF (2 ml) and dried under vacuum to give the title compound (8 mg, 12%). m/z (ES$^+$) 376 (M+H)$^+$.

EXAMPLE 120

N-[3-(Methoxycarbonyl)isoquinolin-5-yl]-N'-[4-(trifluoromethyl)benzyl]urea

Prepared from methyl 5-aminoisoquinoline-3-carboxylate (Description 107) and [4-(trifluoromethyl)benzyl]isocyanate (Description 58) according to Description 61. m/z (ES$^+$) 404 (M+H)$^+$.

EXAMPLE 121

N-(3-Carboxyisoquinolin-5-yl)-N'-[4-(trifluoromethyl)benzyl]urea

Prepared from N-[3-(methoxycarbonyl)isoquinolin-5-yl]-N'-[4-(trifluoromethyl)benzyl]urea (Example 120) according to the procedure of Example 117. m/z (ES$^+$) 390 (M+H)$^+$.

EXAMPLE 122

N-[3-(Dimethylamino)isoquinolin-5-yl]-N'-4-(trifluoromethyl)benzyl]urea

Prepared from 3-(dimethylamino)isoquinolin-5-amine (Description 109) and [4-(trifluoromethyl)benzyl]isocyanate (Description 58) according to the procedure of description 61. m/z (ES$^+$) 389 (M+H)$^+$.

EXAMPLE 123

N-[3-(2-Aminoethyl)isoquinolin-5-yl]-N'-[4-(trifluoromethyl)benzyl]urea

To a solution of tert-butyl 2-(5-aminoisoquinolin-3-yl) ethylcarbamate (Description 116; 200 mg, 0.7 mmol) in deuterated chloroform (5 ml) was added [4-(trifluoromethyl)benzyl]isocyanate (0.506M solution in DCM) (Description 58; 1.38 ml, 0.7 mmol), and the resulting mixture heated at reflux overnight. The reaction mixture was cooled and the precipitate removed by filtration, washed with DCM and dried. The solid was dissolved in methanol (10 ml) and hydrogen chloride gas passed through the mixture for 5 mins, after which time the mixture was left standing for 1 hour. The mixture was evaporated and purified using an SCX cartridge—appropriate fractions were evaporated to give the title compound (25 mg, 9%) as a white solid. m/z (ES$^+$) 389 (M+H)$^+$.

EXAMPLE 124

N-(8-Methoxyisoquinolin-5-yl)-N'-[4-(trifluoromethyl)benzyl]urea

Prepared from 8-methoxyisoquinolin-5-amine which was prepared from 8-methoxy-5-nitroisoquinoline (J. Het. Chem. 37(5), 1293) according to Description 43 and immediately used in reaction with [4-(trifluoromethyl)benzyl] isocyanate (Description 58) according to Description 61. m/z (ES$^+$) 376 (M+H)$^+$.

EXAMPLE 125

N-Isoquinolin-7-yl-N'-[4-(trifluoromethyl)benzyl] urea

A mixture of isoquinolin-7-yl trifluoromethanesulfonate (Description 117, 1.04 g, 3.75 mmol), cesium carbonate (1.6 g, 4.88 mmol), benzophenone imine (747 mg, 4.13 mmol), BINAP (100 mg, 0.16 mmol) and palladium acetate (18 mg, 0.08 mmol) in tetrahydrofuran (15 ml) was degassed ($N_2 \times 3$) then heated at reflux for 18 h. More BINAP (100 mg, 0.16 mmol) and palladium acetate (18 mg, 0.08 mmol) were added and the reaction heated for a further 24 h. The reaction was then cooled to room temperature and partitioned between ethyl acetate (100 ml) and water (100 ml). The aqueous layer was extracted with more ethyl acetate (50 ml) and the combined organic layers were evaporated. The residue was taken up in tetrahydrofuran (40 ml) and 2N hydrochloric acid (aq. 10 ml) was added. After 2 h, the THF was evaporated, 3N hydrochloric acid (aq. 100 ml) was added and the mixture washed with ethyl acetate (2×75 ml). The aqueous layer was then basified by addition of 47% aqueous sodium hydroxide solution and extracted with dichloromethane (3×50 ml). The combined organic layers were dried ($Na_2SO_4$) and evaporated to give crude isoquinolin-7-amine (198 mg) which was reacted directly with [4-(trifluoromethyl)benzyl]isocyanate (Description 58) according to Description 61 to give the title compound (100 mg, 8%). m/z (ES$^+$) 346 (M+H)$^+$.

EXAMPLE 126

N-N'-Diisoquinolin-5-ylurea

Prepared from isoquinoline-5-carboxylic acid and isoquinolin-5-amine according to Description 60. m/z (ES$^+$) 315 (M+H)$^+$.

EXAMPLE 127

N-Isoquinolin-5-yl-N'-[4-(trifluoromethyl)phenyl]urea

Prepared from isoquinolin-5-amine and 4-(trifluoromethyl)phenyl isocyanate according to Description 61. m/z (ES$^+$) 332 (M+H)$^+$.

EXAMPLE 128

N-Isoquinolin-5-yl-N'-{[2-(trifluoromethyl)pyrimidin-5-yl]methyl}urea

Prepared from isoquinoline-5-carboxylic acid and 5-(aminomethyl)-2-(trifluoromethyl)pyrimidine (Description 121) according to the procedure of Description 60. m/z (ES$^+$) 348 (M+H)$^+$.

EXAMPLE 129

Ethyl 3-{[(isoquinolin-5-ylamino)carbonyl]amino}-2-[4-(trifluoromethyl)benzyl]propanoate Ethyl 2-cyano-3-[4-(trifluoromethyl)phenyl]prop-2-enoate (135 mg,0.5 mmol), palladium hydroxide (20 wt % Pd (dry basis on carbon), 20 mg) in ethanol (20 ml) containing 2N hydrochloric acid (1 ml) was placed on a Parr apparatus at 35 psi hydrogen pressure and shaken for 1.5 hours. The reaction mixture was filtered and evaporated to give the corresponding amine which was taken up in THF (5 ml). In a separate flask isoquinolin-5-amine (72 mg, 0.5 mmol) in THF (5 ml) at 0° C. was treated with triphosgene (48 mg, 0.166 mmol) followed by triethylamine (140 μL). After 30 minutes, the amine solution was added and the reaction mixture was stirred at room temperature overnight. The reaction mixture was then filtered and evaporated. Purification by column chromatography using 2.5% methanol in dichloromethane gave the desired product (49 mg). m/z (ES$^+$) 446 (M+H)$^+$.

EXAMPLE 130

3-{[(isoquinolin-5-ylamino)carbonyl]amino}-2-[4-(trifluoromethyl)benzyl]propanoic acid Ethyl 3-{[(isoquinolin-5-ylamino)carbonyl]amino}-2-[4-(trifluoromethyl)benzyl]propanoate (Example 129, 23 mg, 0.05 mmol) in aqueous THF (1:1, 2 ml) was treated with lithium hydroxide (5 mg, 0.1 mmol) and stirred at room temperature for 20 h. The mixture was evaporated then partitioned between 7% aqueous citric acid and dichloromethane (2:1, 6 ml). A precipitate formed which was collected by filtration and dried azeotropically by adding toluene and evaporating to give the desired compound (8.4 mg). m/z (ES$^+$) 418 (M+H)$^+$.

EXAMPLE 131

N-Isoquinolin-5-yl-N'-[4-(morpholin-4-ylmethyl)benzyl]urea

A solution of isoquinoline-5-carbonyl azide (Description 126, 50 mg, 0.25 mmol) in toluene (5 mL) was heated at 75° C. for 1 h. The reaction was cooled to 50° C. and 4-(morpholin-4-ylmethyl)benzylamine (Description 123, 0.31 mmol) was added as a solution in $CH_2Cl_2$ (1 ml). The precipitated product was collected by filtration and washed with hexane, then further purified using mass-directed HPLC to give the title compound (2.5 mg, 3%). m/z (ES$^+$) 376 (M+H)$^+$.

EXAMPLE 132

N-Isoquinolin-5-yl-N'-[2-(2-morpholin-4-ylethoxy)-4-(trifluoromethyl)benzyl]urea A solution of isoquinoline-5-carbonyl azide (Description 126, 43 mg, 0.22 mmol) in toluene (4 mL) was heated at 80° C. for 50 min. The reaction was cooled to 50° C. and 2-(2-morpholin-4-ylethoxy)-4-(trifluoromethyl)benzylamine (Description 125, 66 mg, 0.22 mmol) was added as a solution in toluene (1 ml). The precipitated product was collected by filtration and washed with dichloromethane to give the title compound (83 mg, 80%). m/z (ES$^+$) 475 (M+H)$^+$.

The invention claimed is:

1. A compound of formula (I):

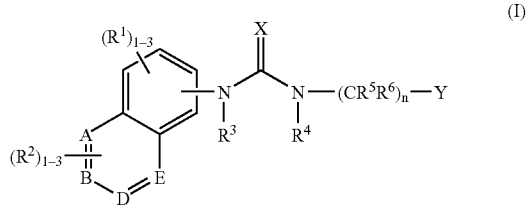

wherein

A and E are each carbon;

one of B and D is carbon, and one of B and D is nitrogen;

$R^1$ and $R^2$ are each independently hydrogen, halogen, hydroxy, $C_{1-6}$alkyl, $C_{2-6}$alkenyl, $C_{2-6}$alkynyl, halo$C_{1-6}$alkyl, hydroxy$C_{1-6}$alkyl, $C_{1-6}$alkoxy, halo$C_{1-6}$alkoxy, hydroxy$C_{1-6}$alkoxy, $C_{3-7}$cycloalkyl, $C_{3-5}$cycloalkyl$C_{1-4}$alkyl, $NR^7R^8$, carboxy, esterified carboxy, $C_{1-6}$alkyl substituted with a group selected from $NR^7R^8$, carboxy and esterified carboxy, or $C_{1-6}$alkoxy substituted with a group selected from $NR^7R^8$, carboxy and esterified carboxy;

$R^3$ and $R^4$ are each independently hydrogen, $C_{1-6}$alkyl, $C_{2-6}$alkenyl or $C_{2-6}$alkynyl;

$R^5$ and $R^6$ are, at each occurrence, independently hydrogen, $C_{1-6}$alkyl, $C_{2-6}$alkenyl, $C_{2-6}$alkynyl, $C_{1-6}$alkoxy, $C_{1-6}$acyloxy, carboxy, esterified carboxy, $CONR^7R^8$, $SO_2R^7$, $SO_2NR^7R^8$, aryl, heteroaryl, heterocyclyl, or $C_{1-6}$alkyl substituted with a group selected from hydroxy, $C_{1-6}$alkoxy, $C_{1-6}$acyloxy, carboxy, esterified carboxy, $NR^7R^8$, $CONR^7R^8$, $SR^7$, $SO_2R^7$, $SO_2NR^7R^8$, aryl, heteroaryl and heterocyclyl; or $R^5$ and $R^6$ and the carbon atom to which they are attached together form a carbocyclic ring of 3 to 6 carbon atoms;

$R^7$ and $R^8$ are, at each occurrence, independently hydrogen, $C_{1-6}$alkyl, $C_{2-6}$alkenyl, $C_{2-6}$alkynyl, $C_{3-7}$cycloalkyl or fluoro$C_{1-6}$alkyl;

or $R^7$ and $R^8$ and the nitrogen atom to which they are attached together form a heteroaliphatic ring of 4 to 7 ring atoms, optionally substituted by one or two groups selected from hydroxy or $C_{1-4}$alkoxy, which ring may optionally contain as one of the said ring atoms an oxygen or a sulfur atom, a group $S(O)$ or $S(O)_2$, or a second nitrogen atom which will be part of a NH or $NR^a$ moiety where $R^a$ is $C_{1-4}$alkyl optionally substituted by hydroxy or $C_{1-4}$alkoxy;

X is an oxygen;

Y is an aryl group selected from unsubstituted naphthyl and phenyl or naphthyl substituted by one or two substituents selected from halogen, $C_{1-4}$alkyl, $C_{1-4}$alkoxy, halo$C_{1-4}$alkyl, halo$C_{1-4}$alkoxy, phenyl, cyano, nitro, pyrazolyl, di($C_{1-6}$alkyl)amino, phenoxy, —OCH$_2$O— and $C_{1-6}$alkylcarbonyl; or Y is a heteroaryl group selected from pyridyl, thiazolyl, isoxazolyl, oxadiazolyl and pyrazolyl wherein each heteroaryl group is optionally substituted with one or two substituents selected from $C_{1-4}$alkyl, $C_{1-4}$alkoxy, halo$C_{1-4}$alkyl, halo$C_{1-4}$alkoxy, unsubstituted heteroaryl or phenyl which may be substituted by $C_{1-6}$alkyl or halogen; or Y is a fused-carbocyclyl group which is a $C_{5-7}$cycloalkyl radical that is fused to a phenyl ring;

n is zero;

or a pharmaceutically acceptable salt, N-oxide or a prodrug thereof.

2. A compound according to claim 1 in which X is O.

3. A compound according to claim 1 in which $R^3$ and $R^4$ are hydrogen.

4. A compound according to claim 1 in which B is nitrogen and A, D and E are carbon.

5. A compound according to claim 1 wherein $R^5$ and $R^6$ each independently represent a hydrogen atom or a $C_{1-4}$alkyl or phenyl group.

6. A compound according to claim 1 or a pharmaceutically acceptable salt or N-oxide thereof for use in a method of treatment of the human or animal body by therapy.

7. The compound N-Isoquinolin-5-yl-N'-[4-(trifluoromethyl)phenyl]urea, or a pharmaceutically acceptable salt, N-oxide or a prodrug thereof.

8. The compound of claim 1, wherein Y is an aryl group selected from unsubstituted naphthyl and phenyl or naphthyl substituted by one or two substituents selected from halogen, $C_{1-4}$alkyl, $C_{1-4}$alkoxy, halo$C_{1-4}$alkyl, halo$C_{1-4}$alkoxy, phenyl, cyano, nitro, pyrazolyl, di($C_{1-6}$alkyl)amino, phenoxy, —OCH$_2$O— and $C_{1-6}$alkylcarbonyl.

9. The compound of claim 1, wherein Y is a heteroaryl group selected from pyridyl, thiazolyl, isoxazolyl, oxadiazolyl and pyrazolyl wherein each heteroaryl group is optionally substituted with one or two substituents selected from $C_{1-4}$alkyl, $C_{1-4}$alkoxy, halo$C_{1-4}$alkyl, halo$C_{1-4}$alkoxy, unsubstituted heteroaryl or phenyl which may be substituted by $C_{1-6}$alkyl or halogen.

10. The compound of claim 1, wherein Y is a fused-carbocyclyl group which is a $C_{5-7}$cycloalkyl radical that is fused to a phenyl ring.

11. A pharmaceutical composition comprising a compound according to claim 1 or a pharmaceutically acceptable salt or N-oxide thereof.

12. A method for treating pain, which method comprises administering to a mammalian patient in need thereof a therapeutically effective amount of the compound of claim 1.

* * * * *